US007754216B2

(12) United States Patent
Scarisbrick et al.

(10) Patent No.: US 7,754,216 B2
(45) Date of Patent: Jul. 13, 2010

(54) METHOD OF TREATING MULTIPLE SCLEROSIS WITH ANTI-K6 ANTIBODY

(75) Inventors: Isobel A. Scarisbrick, Rochester, MN (US); Sachiko I. Blaber, Tallahassee, FL (US); Michael Blaber, Tallahassee, FL (US); Moses Rodriguez, Rochester, MN (US)

(73) Assignees: Mayo Foundation for Medical Education and Research, Rochester, MN (US); Florida State University Research Foundation, Inc., Tallahassee, FL (US)

( * ) Notice: Subject to any disclaimer, the term of this patent is extended or adjusted under 35 U.S.C. 154(b) by 1300 days.

(21) Appl. No.: 10/514,687

(22) PCT Filed: May 21, 2003

(86) PCT No.: PCT/US03/16106

§ 371 (c)(1),
(2), (4) Date: Oct. 21, 2005

(87) PCT Pub. No.: WO03/099328

PCT Pub. Date: Dec. 4, 2003

(65) Prior Publication Data

US 2006/0127391 A1 Jun. 15, 2006

Related U.S. Application Data

(60) Provisional application No. 60/382,471, filed on May 21, 2002.

(51) Int. Cl.
*A61K 39/395* (2006.01)
(52) U.S. Cl. .................. 424/146.1; 424/130.1
(58) Field of Classification Search ............ None
See application file for complete search history.

(56) References Cited

U.S. PATENT DOCUMENTS

| | | | |
|---|---|---|---|
| 3,687,808 | A | 8/1972 | Merigan, Jr. et al. |
| 4,034,074 | A | 7/1977 | Miles |
| 4,098,876 | A | 7/1978 | Piasio et al. |
| 4,233,402 | A | 11/1980 | Maggio et al. |
| 4,469,863 | A | 9/1984 | Ts'o et al. |
| 5,214,136 | A | 5/1993 | Lin et al. |
| 5,218,105 | A | 6/1993 | Cook et al. |
| 5,235,033 | A | 8/1993 | Summerton et al. |
| 5,296,347 | A | 3/1994 | LaMotte, III |
| 5,444,156 | A * | 8/1995 | Veloso et al. ........... 435/337 |
| 5,596,086 | A | 1/1997 | Matteucci et al. |
| 5,750,666 | A | 5/1998 | Caruthers et al. |
| 2001/0016331 | A1 | 8/2001 | Kominami et al. |

FOREIGN PATENT DOCUMENTS

| | | |
|---|---|---|
| CA | 2 360 219 | 4/2002 |
| WO | WO 94/29336 | 12/1994 |
| WO | WO 98/11238 | 3/1998 |
| WO | WO 00/74687 | 12/2000 |

OTHER PUBLICATIONS

Schonfeld, Consultant [online]. Sep. 1, 2008, vol. 48 No. 10. [Retrieved on Jul. 13, 2009]. Retrieved from the Internet:<http://www.consultantlive.com/print/article/10162/1318370?pageNumber=2&printable=true>. Anaphylaxis: Commonsense Ways to Reduce Risk. See pp. 1-7.*
Falkenberg et al. J. Clin. Chem. Clin. Biochem. 1984, 22:867-882.*
GenBank Accession No. AF013988 dated Aug. 12, 1997, 2 pages.
GenBank Accession No. AF016269 dated Feb. 11, 1998, 2 pages.
GenBank Accession No. AF149289 dated Jun. 26, 2000, 5 pages.
GenBank Accession No. D78203 dated Feb. 5, 1999, 2 pages.
"Disease Management Consensus Statement," 2002, National Multiple Sclerosis Society, Expert Opinion Paper downloaded from http://www.nationalmssociety.org/pdf/forpros/Exp_Consensus.pdf, 7 pages.
"Major Diagnostic Tools" [online]. The Multiple Sclerosis Foundation, [retrieved on May 19, 2003]. Retrieved from the Internet: <URL: www.msfacts.org/tools.htm>, 2 pages.
"Treatment of MS" [online]. The Multiple Sclerosis Foundation, [retrieved on May 19, 2003]. Retrieved from the Internet: <URL: www.msfacts.org/treatment.htm>, 3 pages.
"What is Multiple Sclerosis?" [online]. National Multiple Sclerosis Society, 2003, [retrieved on May 19, 2003]. Retrieved from the Internet: <URL: www.nationalmssociety.org/What%20is%20MSX.asp>, 2 pages.
Ausubel et al. (eds.), "Immunology," *Short Protocols in Molecular Biology*, 1992, Chapter 11, Green Publishing Associates and John Wiley & Sons, pp. 11-1 through 11-54.
Bernett et al., "Crystal Structure and Biochemical Characterization of Human Kallikrein 6 Reveals That a Trypsin-like Kallikrein Is Expressed in the Central Nervous System," *J. Biol. Chem.*, 2002, 277(27):24562-24570.
Blaber et al., "Enzymatic Properties of Rat Myelencephalon-Specific Protease," *Biochem.*, 2002, 41:1165-1173.
Chaurand et al., "Peptide and Protein Identification by Matrix-Assisted Laser Desorption Ionization (MALDI) and MALDI-Post-Source Decay Time-of-Flight Mass Spectrometry," *J. Am. Soc. Mass Spectrom.*, 1999, 10(2):91-103.
Cote et al., "Generation of human monoclonal antibodies reactive with cellular antigens," *Proc. Natl. Acad. Sci. USA*, 1983, 80:2026-2030.

(Continued)

*Primary Examiner*—Phillip Gambel
*Assistant Examiner*—Sharon Wen
(74) *Attorney, Agent, or Firm*—Fish & Richardson P.C.

(57) ABSTRACT

Methods and kits for treating inflammatory conditions are described that include modulating kallikrein 6 protease activity.

4 Claims, 25 Drawing Sheets

OTHER PUBLICATIONS

Cole et al., "The EBV-Hybridoma Technique and Its Application to Human Lung Cancer," *Monoclonal Antibodies and Cancer Therapy*, 1983, Alan R. Liss, Inc., pp. 77-96.

Diamandis et al., "Immunofluorometric Assay of Human Kallikrein 6 (Zyme/Protease M/Neurosin) and Preliminary Clinical Applications," *Clin. Biochem.*, 2000, 33(5):369-375.

Gevaert et al., "Protein identification based on matrix assisted laser desorption/ionization-post source decay-mass spectrometry," *Electrophoresis*, 2001, 22(9):1645-1651.

Guatelli et al., "Isothermal, in vitro amplification of nucleic acids by a multienzyme reaction modeled after retroviral replication," *Proc. Natl. Acad. Sci. USA*, 1990, 87:1874-1878.

Holland, "Basic MS Facts," 2002, National Multiple Sclerosis Society, Clinical Bulletin downloaded from http://www.nationalmssociety.org/pdf/forpros/BasicFacts.pdf, 3 pages.

Huse et al., "Generation of a Large Combinatorial Library of the Immunoglobulin Repertoire in Phage Lambda," *Science*, 1989, 246:1275-1281.

Hyrup and Nielsen, "Peptide Nucleic Acids (PNA): Synthesis, Properties and Potential Applications," *Bioorgan. Med. Chem.*, 1996, 4:5-23.

Jackson, "Contributions of Protein Structure-Based Drug Design to Cancer Chemotherapy," *Semin. Oncol.*, 1997, 24:164-172.

Jones et al., "Structure-Based Design of Lipophilic Quinazoline Inhibitors of Thymidylate Synthase," *J. Med. Chem.*, 1996, 39:904-917.

Köhler and Milstein, "Continuous cultures of fused cells secreting antibody of predefined specificity," *Nature*, 1975, 256:495-497.

Kozbor and Roder, "The production of monoclonal antibodies from human lymphocytes," *Immunology Today*, 1983, 4:72-79.

Lassmann et al., "Immunopathology of multiple sclerosis: Report on an international meeting held at the Institute of Neurology of the University of Vienna," *J. Neuroimmunol.*, 1998, 86:213-217.

Lewis, "PCR's Competitors Are Alive and Well and Moving Rapidly Towards Commercialization," *Genetic Engineering News*, 1992, 12(9):1-3.

Louis et al., "Autocrine Inhibition of Mitotic Activity in Cultured Oligodendrocyte-Type-2-Astrocyte (O-2A) Precursor Cells," *Glia*, 1992, 6:30-38.

Magklara et al., "Characterization of the enzymatic activity of human kallikrein 6: autoactivation, substrate specificity, and regulation by inhibitors," *Biochem. Biophys. Res. Comm.*, 2003, 307:948-955.

McCarthy and De Vellis, "Preparation of Separate Astroglial and Oligodendroglial Cell Cultures from Rat Cerebral Tissue," *J. Cell Biol.*, 1980, 85:890-902.

Paty et al., "Interferon beta-1b is effective in relapsing-remitting multiple sclerosis," *Neurology*, 1993, 43:662-667.

Scarisbrick et al., "Nervous System-Specific Expression of a Novel Serine Protease: Regulation in the Adult Rat Spinal Cord by Excitotoxic Injury," *J. Neurosci.*, 1997, 17(21):8156-8168.

Scarisbrick et al., "Activity of a newly identified serine protease in CNS demyelination," *Brain*, 2002, 125:1283-1296.

Scarisbrick et al., "Preferential Expression of Myelencephalon-Specific Protease by Oligodendrocytes of the Adult Rat Spinal Cord White Matter," *Glia*, 2000, 30:219-230.

Scarisbrick et al., "Differential Expression of Brain-Derived Neurotrophic Factor, Neurotropin-3, and Neurotrophin-4/5 in the Adult Rat Spinal Cord: Regulation by the Glutamate Receptor Agonist Kainic Acid," *J. Neurosci.*, 1999, 18(19):7757-7769.

Summerton and Weller, "Morpholino Antisense Oligomers: Design, Preparation, and Properties," *Antisense Nucleic Acid Drug Dev.*, 1997, 7:187-195.

Weiss, "Hot Prospect for New Gene Amplifier," *Science*, 1991, 254:1292-1293.

Yousef and Diamandis, "The New Human Tissue Kallikrein Gene Family: Structure, Function, and Association to Disease," *Endocrine Reviews*, 2001, 22(2):184-204.

Extended European Search Report in EP Application No. 08 01 9970 mailed Apr. 23, 2010, 11 pages.

\* cited by examiner

```
   1 gtcgacccac gcgtccggct ggctggctcg ctctctcctg gggacacaga ggtcggcagg
  61 cagcacacag agggacctac gggcagctgt tccttccccc gactcaagaa tccccggagg
 121 cccggaggcc tgcagcagga gcggccatga agaagctgat ggtggtgctg agtctgattg
 181 ctgcagcctg ggcagaggag cagaataagt tggtgcatgg cgaccctgc gacaagacat
 241 ctcacccta ccaagctgcc ctctacacct cgggccactt gctctgtggt gggtcctta
 301 tccatccact gtgggtcctc acagctgccc actgcaaaaa accgaatctt caggtcttcc
 361 tggggaagca taacctttcgg caaagggaga gttcccagga gcagagttct gttgtccggg
 421 ctgtgatcca cctgactat gatgccgcca gccatcatg ggacatcatg ctgttgcgcc
 481 tggcacgccc agccaaactc tctgaactca tccagcccct tcccctggag agggactgct
 541 cagccaacac caccagctgc cacatcctgg gctggggcaa gacagcagat gggactgatt
 601 ctgacaccat ccagtgtgca tacatccacc tggtgtcccg tgaggagtgt gagcatgcct
 661 accctggcca gatcacccag aacatgttgt gtgctggga tgagaagtac gggaaggatt
 721 cctgccaggg tgattctggg ggtcgctgg tatgtggaga ccacctccga ggcctttgtgt
 781 catgggtaa catcccctgt ggatcaaagg agaagccagg agtctacacc aacgtctgca
 841 gatacagaa ctggatccaa aaaccattcc aggccaagtg accctgacat gtgacatcta
 901 cctcccgacc taccacccca ctggctggtt ccagaacgtc tctcacctag accttgcctc
 961 ccctcctctc ctgcccagct ctgaccctga tgcttaataa acgcagcgac gtgagggtcc
1021 tgattctccc tggttttacc ccagctccat ccttgcatca ctggggagga cgtgatgagt
1081 gaggacttgg gtcctcggtc ttaccccac cactaagaga atacaggaaa atcccttcta
1141 ggcatctcct ctcccaacc cttccacacg tttgatttct tcctgcagag gcccagccac
1201 gtgtctggaa tcccagctcc gctgcttact gtcggtgtcc ccttgggatg taccttttctt
1261 cactgcagat ttctcacctg taagatgaag ataaggatga tacagtctcc ataaggcagt
1321 ggctgttgga aagatttaag gtttcacacc tatgacatac atgaatagc acctgggcca
1381 ccatgcactc aataaagaat gaattttatt atg
```

METHOD OF TREATING MULTIPLE SCLEROSIS WITH ANTI-K6 ANTIBODY

This application is a National Stage application under 35 U.S.C. §371 that claims the benefit of PCT/US03/16106, filed 21 May 2003, which claims the benefit of U.S. Provisional Application Ser. No. 60/382,471, filed 21 May 2002.

TECHNICAL FIELD

The invention relates to methods and materials for treating inflammatory conditions. More specifically, the invention relates to using modulators of kallikrein 6 protease activity to treat inflammatory conditions such as multiple sclerosis.

BACKGROUND

Multiple Sclerosis (MS) is a demyelinating disorder that affects over 350,000 persons in the United States today, with 8,000 new cases reported each year. MS is the most common chronic inflammatory disease involving the nervous system. The majority of people with MS are diagnosed between the ages of 20 and 50, although in rare cases, symptoms may appear in childhood or after age 50. MS is twice as common in women than in men and more frequently diagnosed in Caucasians than other racial groups. The cause of MS is unknown, although there is considerable evidence that it is an autoimmune disease. Although the disease does not result in early death or impairment of cognitive functions, it can cripple the patient by disturbing visual acuity; stimulating double vision; disturbing motor functions affecting walking and use of the hands; producing bowel and bladder incontinence; spasticity; and sensory deficits, such as touch, pain, and temperature sensitivity.

Patients typically are diagnosed based on a combination of patient history and neurologic examination, including magnetic resonance imaging (MRI) of the brain and spinal cord, electrodiagnostic procedures (e.g., evoked potential tests such as visual evoked potentials, brain stem auditory evoked potentials, or somatosensory evoked potentials), and lumbar puncture to look for evidence of immunoglobulin synthesis in the cerebrospinal fluid.

Currently, there is no cure available for MS, so treatment typically involves management of symptoms and treatment of the frequency and severity of relapses. Therapeutics that have been approved since 1993 include interferon-β for use in ambulatory patients with relapsing-remitting MS (Paty et al., *Neurology* 43:662-667, 1993) (e.g., Betaseron® (recombinant interferon β-1β) and Avonex® (recombinant interferon β1α); glatiramer acetate (Copaxone®) for relapsing-remitting MS; and Novantrone® for secondary progressive and relapsing-remitting disease.

SUMMARY

The invention is based on the discovery that modulators of kallikrein 6 (K6) can alter pathogenesis of inflammatory cell mediated diseases both within the central nervous system (CNS) and in the periphery, and as a result, can aid in the treatment and prevention of inflammatory conditions such as MS, rheumatoid arthritis, lupus, and asthma. As described herein, an antibody having specific binding affinity for K6 reduced the degree of demyelination and reduced behavioral deficits in animal models of multiple sclerosis.

The invention features a method for treating an inflammatory condition in a mammal. The method includes administering to the mammal an amount of a K6 modulator effective to treat the inflammatory condition, and can further include monitoring the inflammatory condition in the mammal. The inflammatory condition can be selected from the group consisting of multiple sclerosis, rheumatoid arthritis, lupus, and asthma. The method is particularly useful for multiple sclerosis. The K6 modulator can be an antibody having specific binding affinity for K6. The antibody can be polyclonal or monoclonal, and can inhibit the enzyme activity of K6. The K6 modulator can be an antisense nucleic acid that inhibits the expression of K6. In some embodiments, the K6 modulator is a peptide nucleic acid that inhibits the expression of K6. The K6 modulator also can be a serine protease inhibitor.

In another aspect, the invention features an antibody that specifically binds to human K6 and inhibits the enzymatic activity of K6 and kits containing such an antibody. The antibody can be polyclonal or monoclonal. A kit further can include a label or package insert indicating that the antibody is useful for treating an inflammatory condition.

The invention also features a method for screening a subject for an inflammatory condition. The method includes detecting the level of K6 protein or RNA present in a biological sample from the subject; and comparing the level of K6 protein or RNA in the sample to the corresponding level in a control population, wherein an increase in the level of K6 protein or RNA in the subject relative to that of the control population is indicative of the inflammatory condition in the subject.

A method for monitoring therapy for an inflammatory condition also is featured. The method includes detecting the level of K6 protein or RNA present in a biological sample from a subject undergoing treatment for the inflammatory condition; and comparing the level of K6 protein or RNA in the sample to a baseline level of K6 present in the subject, wherein a decrease in the level of K6 protein or RNA in the subject relative to that of the control population is indicative of a positive response to the therapy in the subject. The inflammatory condition can be selected from the group consisting of multiple sclerosis, rheumatoid arthritis, lupus, and asthma. The biological sample can be selected from the group consisting of serum and cerebrospinal fluid.

The level of K6 protein can be detected immunologically. For example, the level of K6 protein can be detected using a monoclonal antibody. The level of K6 also can be detected using a capture antibody and a detection antibody, wherein the detection antibody includes a label (e.g., a fluorophore such as fluorescein, fluorescein isothiocyanate (FITC), phycoerythrin (PE), allophycocyanin (APC), or peridinin chlorophyll protein (PerCP); biotin; an enzyme; or a radioisotope. The capture antibody can be attached to a solid substrate (e.g., a bead or a microtiter plate). The capture antibody can be a polyclonal antibody.

In another aspect, the invention features an antisense oligonucleotide that inhibits the expression of K6, wherein the oligonucleotide is at least 8 nucleotides in length. The oligonucleotide can be at least 15 nucleotides in length.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DESCRIPTION OF DRAWINGS

In FIG. 5A, lanes 1-6 are molecular mass standards kDa), gelatin+K6 0 min; 5 min; 30 min; 60 min; gelatin alone 60 min incubation, respectively. In FIG. 5B, lanes 1-5 are molecular mass standards; fibronectin+K6 0 hr; 1 hr; 24 hr; fibronectin control 24 hr, respectively.

In FIG. 6A, lanes 1-9 are molecular mass markers; no K6; 0 min; 1 min; 2 min; 5 min; 10 min; 30 min; 60 min incubation with K6, respectively. In FIG. 6B, lanes 1-6 are molecular mass markers; 0 min; 1 hr; 4 hr; 12 hrs; and molecular mass markers, respectively.

FIG. 9 is a Western blot showing the endogenous inhibitor of K6 is unique in CNS relative to non-CNS tissues. Mature K6 is marked by an arrow. Lanes 1-4 are 10 ng r-K6; 2.2 mg/ml spinal cord; 6.4 mg/ml brain; 9.6 mg/ml kidney, respectively. The higher molecular weight complexes may represent the formation of K6/inhibitor complexes, with masses of approximately 42 and 91 kDa. The larger 91 kDa complex is found primarily in the kidney (double asterisks), whereas the 42 kDa complex is found predominantly in the brain and spinal cord (single asterisk).

(A) The severity of clinical disease was reduced in mice pre-immunized with K6 compared to control groups immunized with PBS alone, or receiving no prior immunization (*Mann Whitney U, P<0.05), (n=14 per group). (B) The number of quandrants of the spinal cord associated with pathology or meningeal inflammation also were significantly reduced in K6-pre-immunized mice relative to controls when examined at the 12 day time point (unpaired Student's t-test, $P \leq 0.05$). (C) Splenic lymphocytes were harvested from all mice examined in (A), and viable cells ($5 \times 10^5$/well) were cultured with indicated concentrations of PLP139-151 for 4 days. Cultures were pulsed with $^{3H}$TdR 18 hrs prior to harvest. Data shown represent the combined data of two separate experiments. Splenocytes harvested from K6-immunized mice exhibited significantly less proliferation in response to the priming antigen, compared to their immunization controls (*$P \leq 0.005$, unpaired Students t-test). (D) DTH responses to the initiating PLP139-151 peptide were evaluated in all mice at day 9 after priming. Data shown represent the mean 24-hr and 48 hr change in ear thickness±SEM, in response to challenge with 10 µg of PLP139-151 peptide. DTH responses were significantly reduced in the K6-immunized mice at the 48 hr time point (*P<0.05, unpaired Students t-test).

Figure 19:
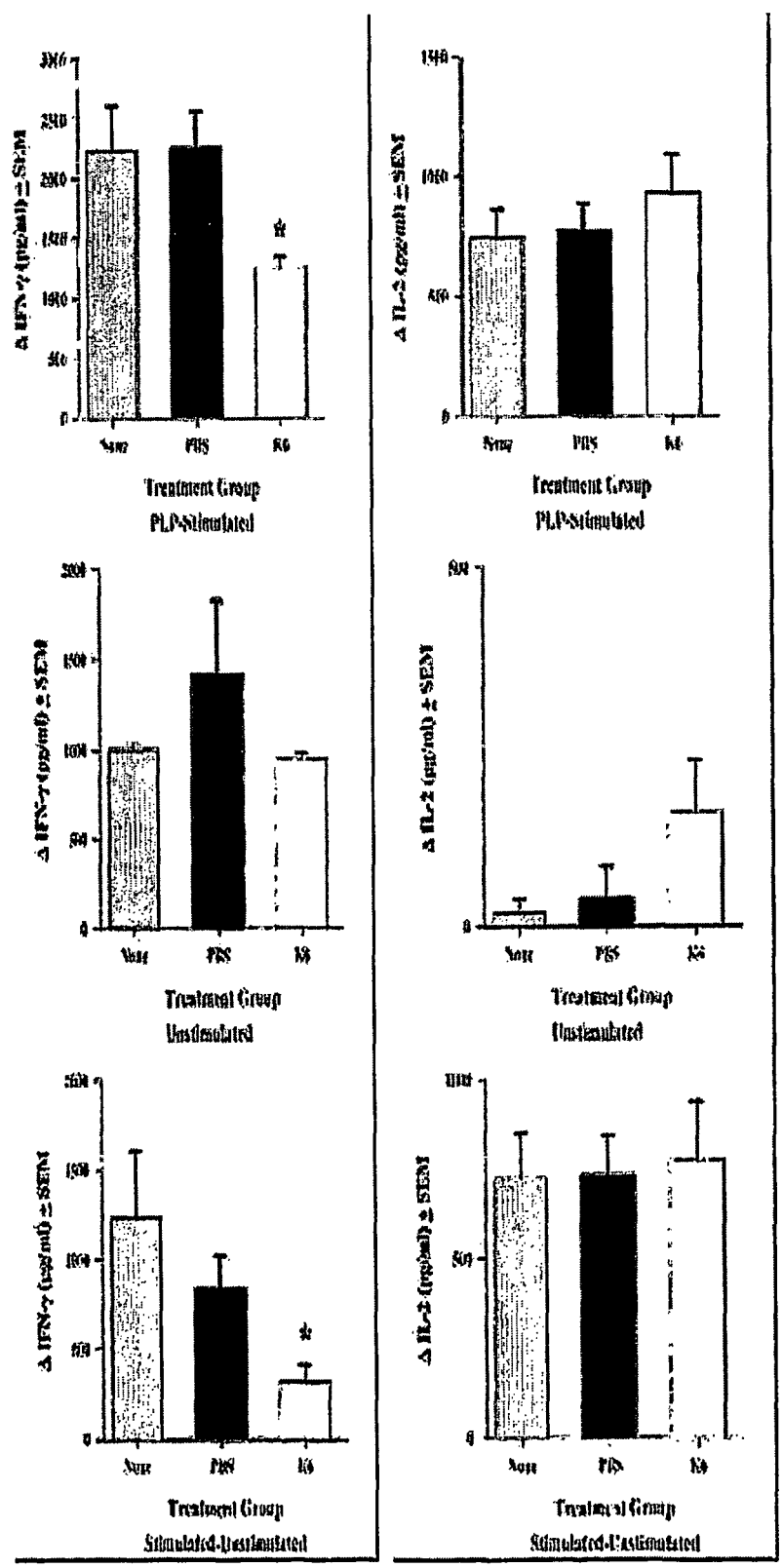

FIG. 19 contains graphs depicting a decrease in antigen specific Th1 cytokine production in response to K6 immunization. Splenocytes were cultured from the animals described in FIGS. 18A to 18D on day 12 post EAE-induction and stimulated with the priming antigen, PLP-139-151, for a period of 72 hr. Cell culture supernatants were harvested and analyzed for IFN-γ and IL-2 secretion by capture ELISA techniques. IFN-γ production, a Th1 cytokine, was significantly reduced in K6-immunized mice (*unpaired Student's t-test, P<0.05). By contrast, IL-2, a Th0 cytokine, was comparable between the different experimental groups.

FIG. 20A is a photograph of a 20% Tricine SDS-PAGE (run under reducing conditions) gel showing hydrolysis of rat MBP in the presence or absence of IgG isolated from K6-immunized mice or controls. Lanes: 1, molecular mass markers; 2 anti-K6 IgG+K6+MBP; 3 anti-CFA IgG+K6+MBP; 4 K6+MBP; 5 anti-K6 IgG+MBP; 6 anti-CFA IgG+MBP; 7 MBP alone.

FIG. 20B is a graph depicting the rate of AcATRpNA-substrate hydrolysis over time by K6 in the presence of IgG isolated from K6 immunized mice or controls.

Figure 21:
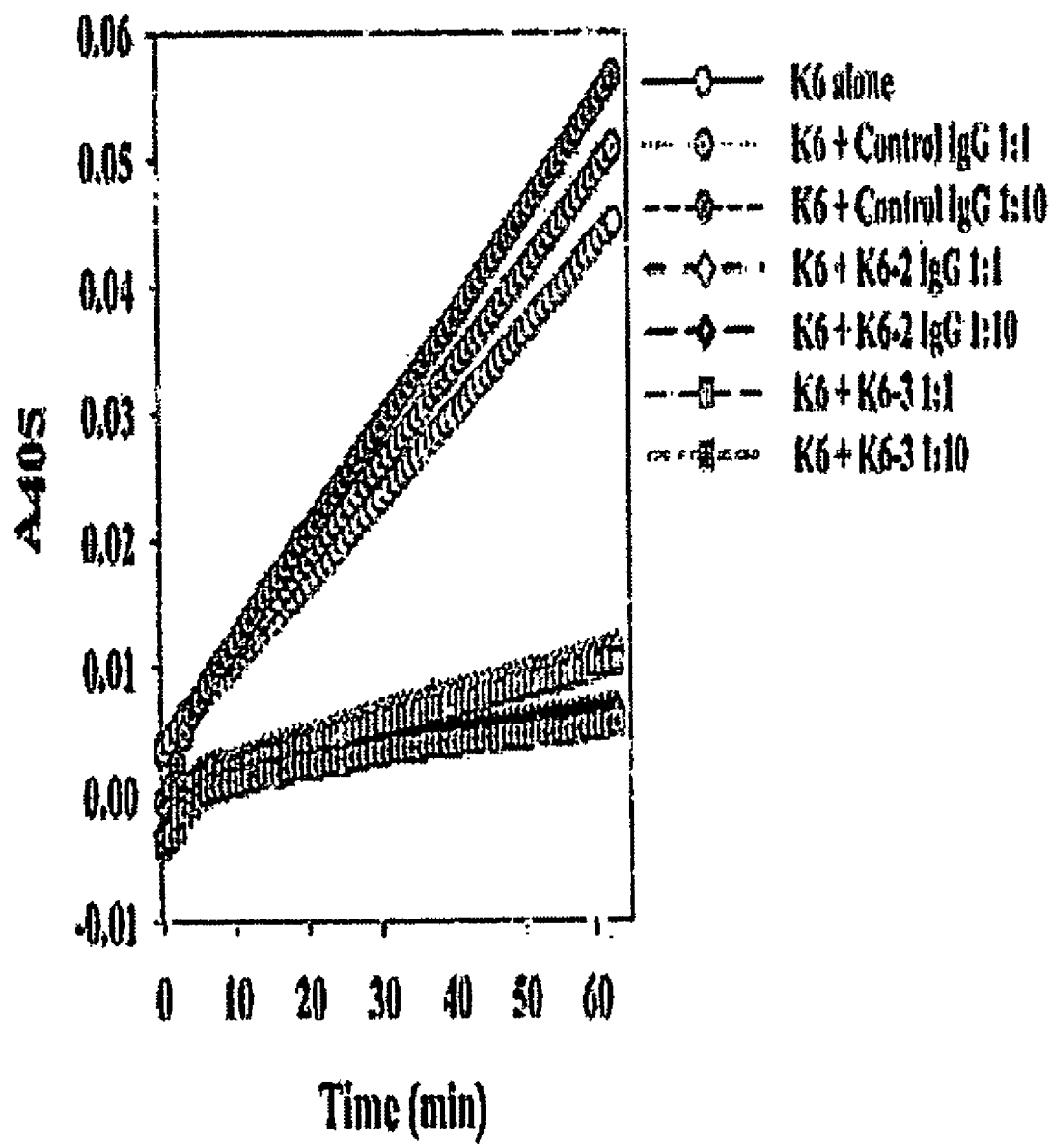

FIG. 21 is a graph depicting ability of monoclonal antibodies specific for K6 to block K6 enzymatic activity in vitro.

Figure 22:
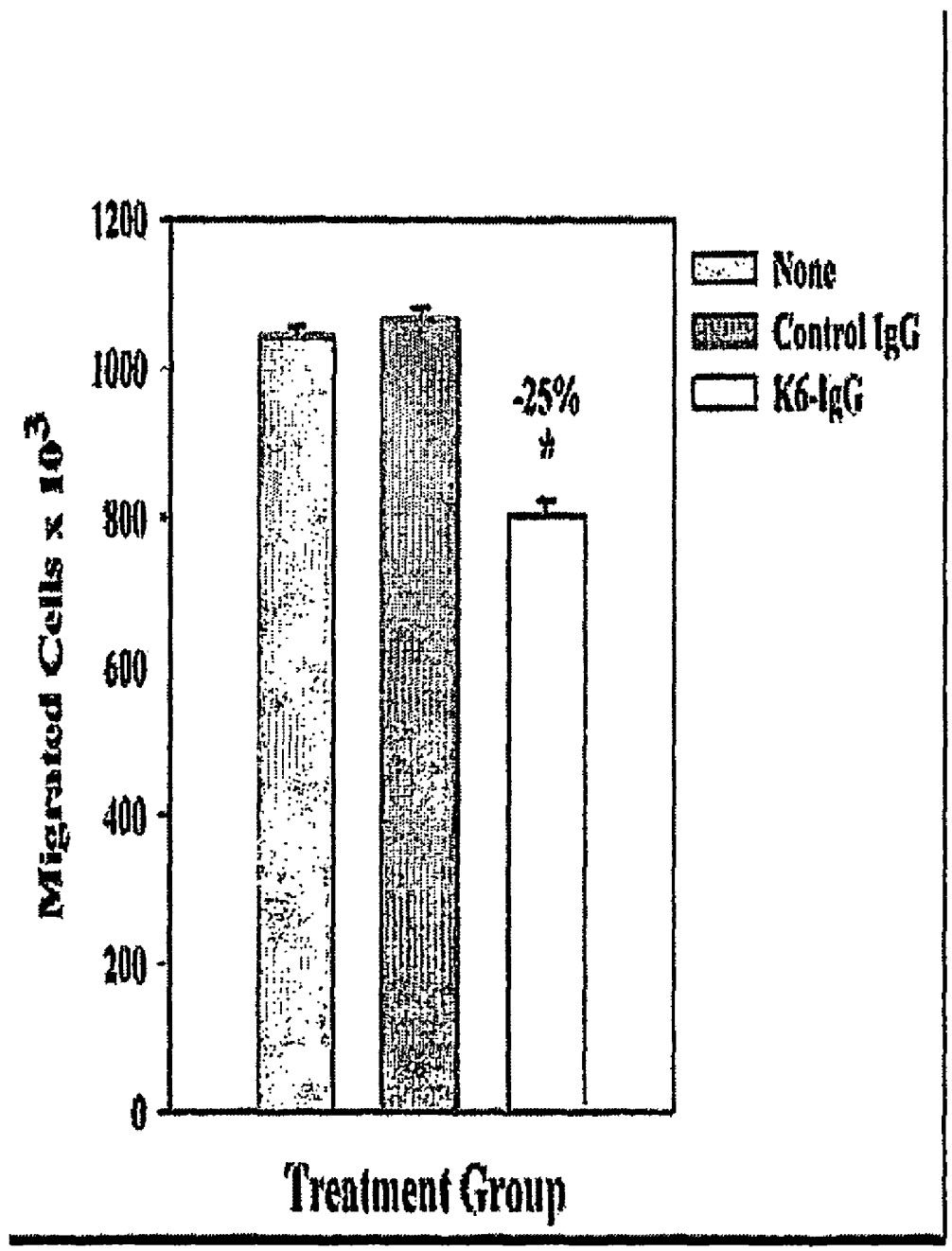

FIG. 22 is a graph depicting that immuoglobulin isolated from K6-immunized mice inhibits the migration of activated splenocytes in vitro. Compared with normal mouse IgG (control) and to the addition of no antibody, the addition of K6-IgG inhibited migration by 25% (*unpaired Student's t-test).

Figure 23:
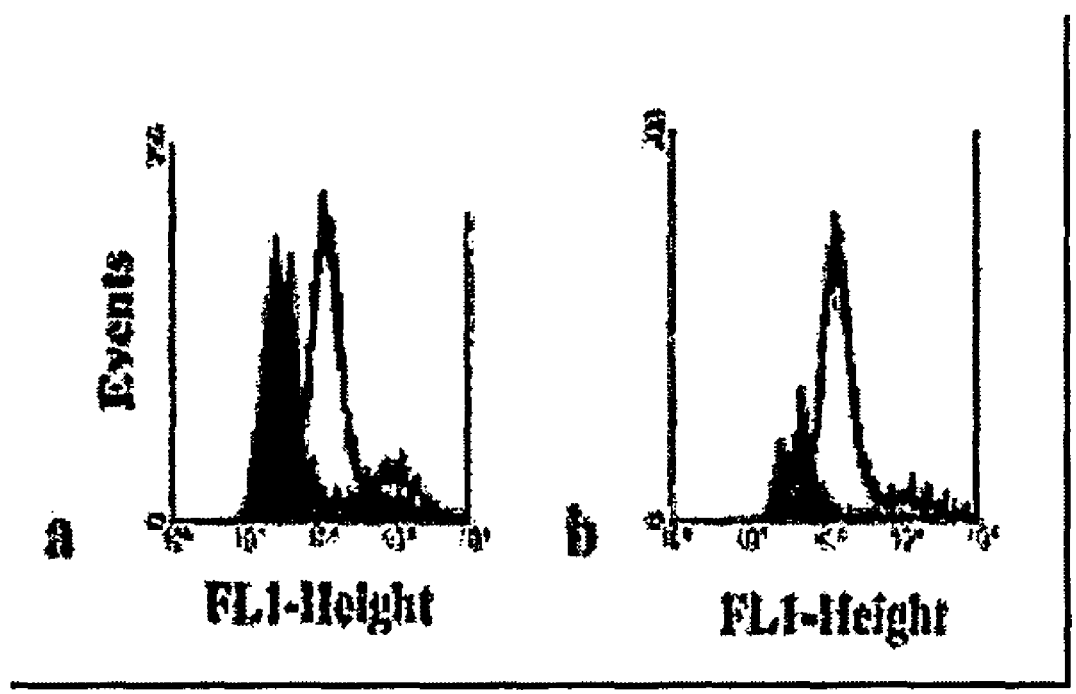

FIGS. 23A and 23B are histograms showing intracellular staining of K6 determined by flow cytometry. The filled areas show constitutive intracellular expression of K6 by CD4+ (A) and CD8+ (B) splenocytes cultured in PBS.

Figure 24:
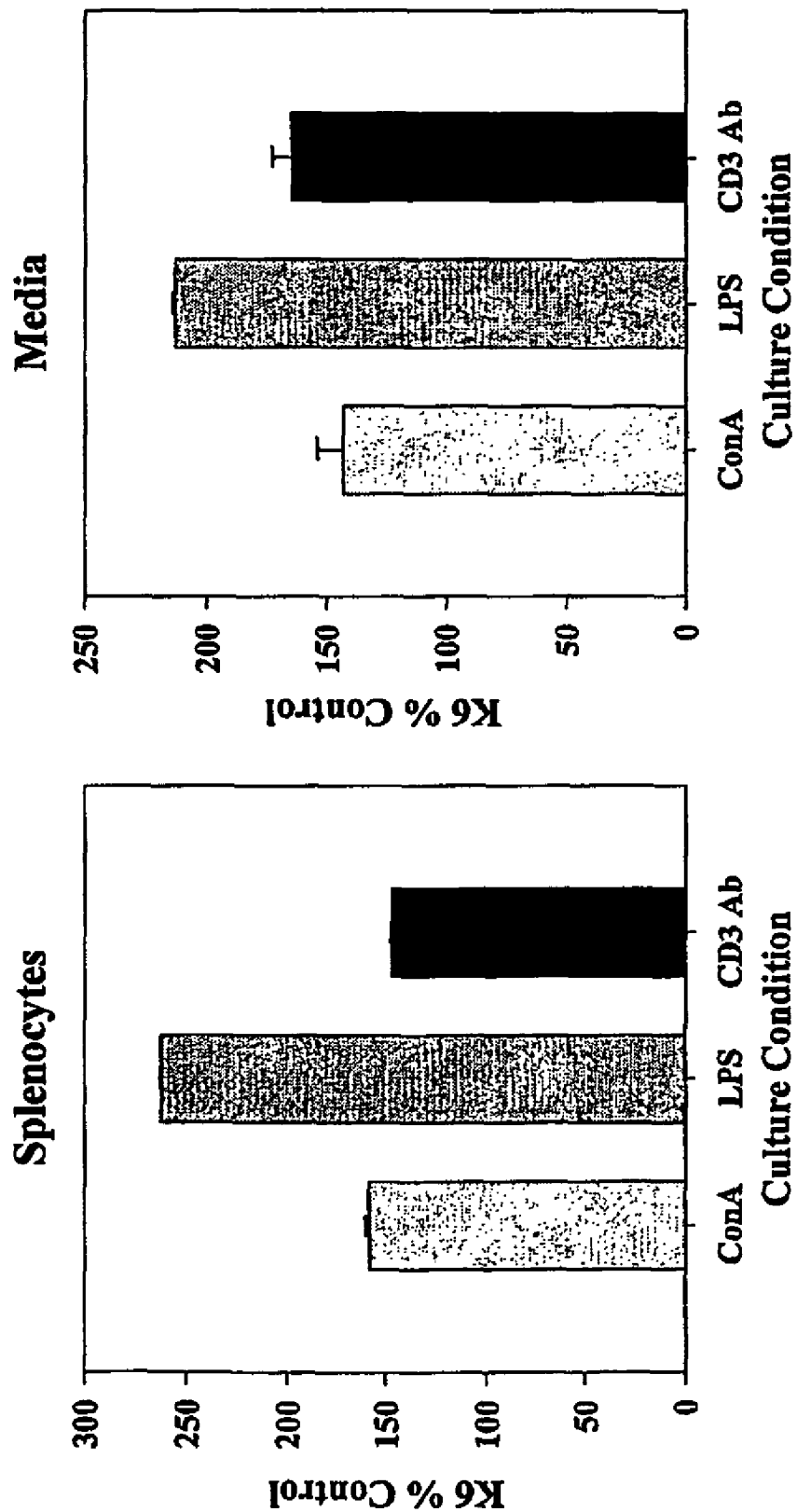

FIG. 24 (left panel) and 24 (right panel) are graphs depicting that splenocyte activation resulted in an increase in K6-production and secretion. Splenocytes were grown in media containing PBS, as a control (left panel) or in media containing 10 µg/ml Con A, 5 mg/ml LPS (right panel). Alternatively, flasks were pre-coated with 10 µg/ml CD3 antibody (Ab) for CD3 receptor cross-linking. Specific activation of T cells (Con A and CD3 Ab), or non-specific activation of all splenocytes, produced a significant increase in K6 production, and secretion into the media, compared to those cells grown in PBS alone.

FIG. 25 is the nucleotide sequence (SEQ ID NO:2) encoding human K6.

DETAILED DESCRIPTION

In general, the invention provides methods for treating inflammatory conditions in mammals using modulators of K6 as well as methods of detecting the presence of an inflammatory condition and monitoring inflammatory disease state by detecting the level of K6 protein or a ribonucleic acid encoding K6 in biological samples from the mammals. The term "K6" as used herein refers to mammalian kallikrein 6 (e.g., from mice, rat, and humans). It should be noted that human K6 also is referred to as protease M, neurosin, zyme, and myelencephalon-specific protease (MSP). In the mouse, K6 also is referred to as brain and skin serine protease (BSSP) or brain serine protease (BSP). The nucleic acid sequence encoding human K6 can be found in GenBank under Accession Nos. AF013988, AF149289, and D78203. K6 is expressed in the CNS and within the CNS, is most abundant in the hippocampus, substantia nigra, basal ganglia, and spinal cord. K6 exhibits a limited distribution in non-neural tissues. Within normal white matter, K6 expression is almost exclusively associated with oligodendroglia. K6 levels are up-regulated in both neural and glial elements following injurious events, such as glutamate-receptor mediated excitotoxic injury.

Without being bound by a particular mechanism, K6 is localized within both macrophages and T cell subsets at sites of CNS inflammation and demyelination and can degrade myelin-specific and extracellular matrix proteins, and when present in excess, negatively effect oligodendrocyte process outgrowth and integrity. K6 may facilitate transendothelial migration of inflammatory cells into, and within, the CNS.

Methods of Treating Inflammatory Conditions

The term "inflammatory condition" as used herein refers to any inflammatory cell mediated disease within the CNS or within the periphery, including infectious (bacterial or viral) and autoimmune diseases. Non-limiting examples of inflammatory conditions affecting the nervous system include MS; all types of encephalitis and meningitis; acute disseminated encephalomyelitis; acute transverse myelitis; neuromyelitis optica; focal demyelinating syndromes (e.g., Balo's concentric sclerosis and Marburg variant of MS); progressive multifocal leukoencephalopathy; subacute sclerosing panencephalitis; acute haemorrhagic leucoencephalitis (Hurst's disease); human T-lymphotropic virus type-1-associated myelopathy/tropical spactic paraparesis; Devic's disease; human immunodeficiency virus encephalopathy; human immunodeficiency virus vacuolar myelopathy; peipheral neuropathies; Guillanin-Barre Syndrome and other immune mediated neuropathies; and myasthenia gravis. Non-limiting examples of non-nervous system inflammatory conditions include rheumatoid arthritis; osteoarthritis; infectious arthritis; psoriatic arthritis; polychondritis; periarticular disorders; colitis; pancreatitis; system lupus erythematosus; conjunctivitis; diabetes type II; dermatitis; asthma; systemic sclerosis (scleroderma); Sjogren's syndrome; Behcet's Syndrome; vasculitis sarcoidosis amyloidosis; allergies; anaphylaxis; systemic mastocytosis; and infectious diseases of the internal organs such as hepatitis or ulcers.

Typically, a K6 modulator is administered to a mammal such as a human patient that has been diagnosed with an inflammatory condition (e.g., MS). Suitable modulators can decrease the expression of a nucleic acid encoding K6, decrease levels of the K6 protein, or inhibit K6 activity. K6 modulators that can be used include, for example, antibodies having specific binding affinity for K6, antisense K6 molecules, selective serine protease inhibitors, and pharmaceutically acceptable salts thereof. K6 modulators also can be administered prophylactically in patients at risk for developing inflammatory conditions to prevent development of symptoms of the disease from occurring, delaying onset of symptoms, or lessening the severity of subsequently developed disease symptoms. As described herein, immunization with K6 in an autoimmune model of MS (experimental allergic encephalomyelitis (EAE) model) inhibited the development of clinical signs of EAE. In either case, an amount of a K6 modulator effective to treat the inflammatory condition is administered to the patient. Treatment of an inflammatory condition can include reducing the severity of the disease or slowing progression of the disease. As used herein, the term "effective amount" refers to an amount of a K6 modulator that reduces the deleterious effects of the inflammatory condition without inducing significant toxicity to the host. Effective amounts of K6 modulators can be determined by a physician, taking into account various factors that can modify the action of drugs such as overall health status, body weight, sex, diet, time and route of administration, other medications, and any other relevant clinical factors.

A K6 modulator can be administered by any route, including, without limitation, oral or parenteral routes of administration such as intravenous, intramuscular, intraperitoneal, subcutaneous, intrathecal, intraarterial, nasal, transdermal (e.g., as a patch), or pulmonary absorption. A K6 modulator can be formulated as, for example, a solution, suspension, or emulsion with pharmaceutically acceptable carriers or excipients suitable for the particular route of administration, including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives, flavorings, sugars, and other additives such as antimicrobials, antioxidants, chelating agents, inert gases, and the like also may be present.

For oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Nasal preparations can be presented in a liquid form or as a dry product. Nebulised aqueous suspensions or solutions can include carriers or excipients to adjust pH and/or tonicity.

In some embodiments, anti-inflammatory agents are administered in combination with a modulator of K6. For example, a non-steroidal anti-inflammatory agent such as acetaminophen, ibuprofen, or nabumetone or a steroid such as prednisolone can be administered to a subject. A modulator of K6 also can be administered with an immunomodulator such as interferon β (e.g., Betaseron® (recombinant interferon β-1β) and Avonex® (recombinant interferon β-1α): glatiramer acetate (Copaxone®) for relapsing-remitting MS; or Novantrone®.

Methods of the invention can include monitoring the inflammatory condition to, for example, determine if the inflammatory condition is improving with treatment. Any method can be used to monitor an inflammatory condition. For example, for multiple sclerosis patients, lower extremity function, upper extremity function, vision, and cognitive function can be monitored. Magnetic resonance imaging (e.g., fluid-attenuated inversion recovery) can be performed to examine lesions and to differentiate old lesions from new or active lesions. Evoked potential tests can be performed to monitor nerve transmission. For example, visual evoked potentials can be used to detect optic neuritis. Brain stem auditory evoked potentials can be used to detect abnormalities in patients with demyelinating lesions in the brainstem that can cause delays in the transmission of sound. Somatosensory evoked potentials can be used to detect disruptions in the pathways from the arms and legs to the brain at very specific positions of the CNS. Cerebrospinal fluid can be examined for myelin breakdown products, oligoclonal bands, or IgG antibodies (e.g., IgG index). In addition, as discussed below, levels of K6 protein or ribonucleic acid (RNA) can be monitored.

Anti-K6 Antibodies

Antibodies having specific binding affinity for K6 can be used to modulate K6 (e.g., decrease activity). As used herein, the terms "antibody" or "antibodies" include intact molecules as well as fragments thereof that are capable of binding to an epitopic determinant of K6 (e.g., human K6). The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of noncontiguous amino acids that define a particular structure (e.g., a conformational epitope). The terms "antibody" and "antibodies" include polyclonal antibodies, monoclonal antibodies, humanized or chimeric antibodies, single chain Fv antibody fragments, Fab fragments, and F(ab)₂ fragments. Polyclonal antibodies are heterogenous populations of antibody molecules that are contained in the sera of the immunized animals. Monoclonal antibodies are homogeneous populations of antibodies to a particular epitope of an antigen.

Antibody fragments that have specific binding affinity for K6 can be generated by known techniques. For example, F(ab')2 fragments can be produced by pepsin digestion of the antibody molecule; Fab fragments can be generated by reducing the disulfide bridges of F(ab')2 fragments. Alternatively, Fab expression libraries can be constructed. See, for example, Huse et al., *Science,* 246:1275 (1989). Once produced, antibodies or fragments thereof are tested for recognition of K6 by standard immunoassay methods including ELISA techniques, radioimmunoassays, and Western blotting. See, *Short Protocols in Molecular Biology*, Chapter 11, Green Publishing Associates and John Wiley & Sons, Edited by Ausubel, F. M et al., 1992.

Antibodies having specific binding affinity for K6 can be produced through standard methods. In general, a K6 polypeptide can be recombinantly produced, or can be purified from a biological sample, and used to immunize animals. As used herein, the term "polypeptide" refers to a polypeptide of at least five amino acids in length. To produce a recombinant K6 polypeptide, a nucleic acid sequence encoding a K6 polypeptide can be ligated into an expression vector and used to transform a bacterial or eukaryotic host cell. Nucleic acid constructs typically include a regulatory sequence operably linked to a K6 nucleic acid sequence. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

Mammalian cell lines that stably express a K6 polypeptide can be produced by using expression vectors with the appropriate control elements and a selectable marker. For example, the eukaryotic expression vector pCDNA.3.1+ (Invitrogen, San Diego, Calif.) is suitable for expression of a K6 polypeptide in, for example, COS cells, Chinese hamster ovary (CHO), or HEK293 cells. Following introduction of the expression vector by electroporation, DEAE dextran, or other suitable method, stable cell lines are selected. Alternatively, K6 can be transcribed and translated in vitro using wheat germ extract or rabbit reticulocyte lysase.

In eukaryotic host cells, a number of viral-based expression systems can be utilized to express a K6 polypeptide. A nucleic acid encoding a K6 polypeptide can be introduced into a SV40, retroviral or vaccinia based viral vector and used to infect host cells. Alternatively, a nucleic acid encoding a K6 polypeptide can be cloned into, for example, a baculoviral vector and then used to transfect insect cells. For example, the cDNA encoding the sequence for the mature form of K6 can be inserted into the pBAC3 transfer vector (Novagen, Madison, Wis.) immediately 3' to the enterokinase (EK) recognition sequence of (Asp)4Lys. This results in a 44 amino acid synthetic prosequence (ending in the EK recognition sequence) leading into the amino-terminal Val-Val-His-Gly (SEQ ID NO:1) sequence of the mature form of K6. Expression of K6 in a pBAC3 transfer vector can use the BacVector transfection system (Novagen, Madison, Wis.). The Sf9 insect cell line, in conjunction with sf-900 II serum-free media (Life Technologies, Rockville, Md.), can be used for preparation of high-titer (i.e., $>10^9$ pfu/mL) viral stock. The TN5 (High5, Invitrogen Corp., Carlsbad, Calif.) insect cell line can be used for production of expressed protein by the viral stock. Recombinant K6 protein can be purified in a single step utilizing the His-tag fusion and nickel affinity resin (Ni-NTA). The eluted K6 fraction can be pooled and extensively dialyzed versus 40 mM Tris-HCl, pH 7.5 (or 40 mM sodium acetate, pH 4.5), using 6-8 kDa molecular mass cutoff dialysis tubing (Spectrum Laboratories, Rancho Dominguez, Calif.).

Various host animals can be immunized by injection of the K6 polypeptide. Host animals include rabbits, chickens, mice, guinea pigs and rats. Various adjuvants that can be used to increase the immunological response depend on the host species and include Freund's adjuvant (complete and incomplete), mineral gels such as aluminum hydroxide, surface-active substances such as lysolecithin, pluronic polyols, polyanions, peptides, oil emulsions, keyhole limpet hemocyanin and dinitrophenol. Monoclonal antibodies can be prepared using a K6 polypeptide and standard hybridoma technology. In particular, monoclonal antibodies can be obtained by any technique that provides for the production of antibody molecules by continuous cell lines in culture such as described by Kohler, G. et al., *Nature*, 256:495 (1975), the human B-cell hybridoma technique (Kosbor et al., *Immunology Today*, 4:72 (1983); Cole et al., *Proc. Natl. Acad. Sci USA*, 80:2026 (1983)), and the EBV-hybridoma technique (Cole et al., "Monoclonal Antibodies and Cancer Therapy", Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies of the invention can be cultivated in vitro and in vivo.

In some embodiments, antibodies of the invention can inhibit the enzymatic activity of K6. In vitro assays can be used to monitor K6 activity after incubation in the presence of an antibody. Typically, K6 can be incubated with an antibody (e.g, polyclonal or monoclonal), then the ability of K6 to cleave a substrate such as myelin basic protein or an arginine-specific fluorogenic substrate can be assessed at 37° C. in a suitable buffer (e.g., Tris buffer). Depending on the substrate, cleavage can be monitored using sodium dodecyl sulfate (SDS)-polyacrylamide gel electrophoresis (PAGE) or a spectrophotometer.

Antisense Oligonucleotides

Antisense oligonucleotides can be used to modulate K6 by decreasing levels of K6 protein. The antisense oligonucleotides in accordance with this invention are at least 8 nucleotides in length. For example, a nucleic acid can be about 8, 9, 10-20 (e.g., 11, 12, 13, 14, 15, 16, 17, 18, 19, or 20 nucleotides in length), 15 to 20, 18-25, or 20-50 nucleotides in length. In other embodiments, antisense molecules can be used that are greater than 50 nucleotides in length, including the full-length sequence of a K6 mRNA. As used herein, the term "oligonucleotide" refers to an oligomer or polymer of ribonucleic acid (RNA) or deoxyribonucleic acid (DNA) or analogs thereof. Nucleic acid analogs can be modified at the base moiety, sugar moiety, or phosphate backbone to improve, for example, stability, hybridization, or solubility of a nucleic acid. Modifications at the base moiety include substitution of deoxyuridine for deoxythymidine, and 5-methyl-2'-deoxycytidine and 5-bromo-2'-deoxycytidine for deoxycytidine. Other examples of nucleobases that can be substituted for a natural base include 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Other useful nucleobases include those disclosed, for example, in U.S. Pat. No. 3,687,808.

Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone (e.g., an aminoethylglycine backbone) and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone. See, for example, U.S. Pat. Nos. 4,469,863, 5,235,033, 5,750,666, and 5,596,086 for methods of preparing oligonucleotides with modified backbones.

Antisense oligonucleotides of the invention also can be modified by chemical linkage to one or more moieties or conjugates that enhance the activity, cellular distribution or cellular uptake of the oligonucleotide. Such moieties include but are not limited to lipid moieties (e.g., a cholesterol moiety); cholic acid; a thioether moiety (e.g., hexyl-S-tritylthiol); a thiocholesterol moiety; an aliphatic chain (e.g., dodecandiol or undecyl residues); a phospholipid moiety (e.g., di-hexadecyl-rac-glycerol or triethyl-ammonium 1,2-di-O-hexadecyl-rac-glycero-3-H-phosphonate); a polyamine or a polyethylene glycol chain; adamantane acetic acid; a palmityl moiety; or an octadecylamine or hexylamino-carbonyl-oxycholesterol moiety. The preparation of such oligonucleotide conjugates is disclosed in, for example, U.S. Pat. Nos. 5,218,105 and 5,214,136.

Methods for synthesizing antisense oligonucleotides are known, including solid phase synthesis techniques. Equipment for such synthesis is commercially available from several vendors including, for example, Applied Biosystems (Foster City, Calif.). Alternatively, expression vectors that contain a regulatory element that directs production of an antisense transcript can be used to produce antisense molecules.

Antisense oligonucleotides can bind to a nucleic acid encoding K6, including DNA encoding K6 RNA (including pre-mRNA and mRNA) transcribed from such DNA, and also cDNA derived from such RNA, under physiological conditions (i.e., physiological pH and ionic strength). The nucleic acid sequence encoding human K6 can be found in GenBank under Accession Nos. AF013988, AF149289, and D78203. The nucleic acid sequence encoding rat K6 can be found in GenBank under Accession No. AF016269. For example, an antisense oligonucleotide can hybridize under physiological conditions to the nucleotide sequence set forth in GenBank Accession Nos. AF013988 (FIG. 25; SEQ ID NO:2), AF149289, D78203, or AF016269.

It is understood in the art that the sequence of an antisense oligonucleotide need not be 100% complementary to that of its target nucleic acid to be hybridizable under physiological conditions. Antisense oligonucleotides hybridize under physiological conditions when binding of the oligonucleotide to the K6 nucleic acid interferes with the normal function of the K6 nucleic acid, and non-specific binding to non-target sequences is minimal.

Target sites for K6 antisense oligonucleotides include the regions encompassing the translation initiation or termination codon of the open reading frame (ORF) of the gene. In addition, the ORF has been targeted effectively in antisense technology, as have the 5' and 3' untranslated regions. Furthermore, antisense oligonucleotides have been successfully directed at intron regions and intron-exon junction regions. Further criteria can be applied to the design of antisense oligonucleotides. Such criteria are well known in the art, and are widely used, for example, in the design of oligonucleotide primers. These criteria include the lack of predicted secondary structure of a potential antisense oligonucleotide, an appropriate G and C nucleotide content (e.g., approximately 50%), and the absence of sequence motifs such as single nucleotide repeats (e.g., GGGG runs). The effectiveness of antisense oligonucleotides at modulating expression of a K6 nucleic acid can be evaluated by measuring levels of the K6 mRNA or protein (e.g., by Northern blotting, RT-PCR, Western blotting, ELISA, or immunohistochemical staining).

Identifying Modulators of K6

The invention provides methods for identifying K6 modulators that are suitable for treating one or more inflammatory conditions in mammals. In vitro or in vivo models of inflammatory conditions can be used to identify suitable modulators of K6. In vitro cell lines, including CG4 OLG cell line, or cultured explants or cultures (e.g., purified cultures of OLG progenitors) from an animal model, can be used to identify suitable K6 modulators. Such cells can be treated with a test compound over a period of time (e.g., days, weeks, or longer) then samples (e.g., cells and cell medium) can be collected and examined, for example, for OLG process stability and outgrowth. As a control, the effect of the test compound can be compared with cultures treated with a serine protease inhibitor (positive control) and to untreated cultures (negative control). Other assays for identifying K6 modulators include contacting immune cell cultures with a test compound and determining transmigration ability of the cells in vitro. See Example 16 for such an assay. In addition, K6 can be incubated with a test compound and ability to cleave a substrate can be monitored. See Example 15 for such an assay.

Once a test compound is determined to be effective in vitro, the test compound can be tested in vivo. For example, a test compound can be administered to an animal model of multiple sclerosis, such as the Theiler's murine encephalomyelitis virus (TMEV) model or the EAE model (autoimmune model). Samples (e.g., cerebrospinal fluid, blood, serum, or tissue) can be collected over a period of time and assayed. For example, cerebrospinal fluid can be assayed for myelin breakdown products. Spinal cord pathology can be examined for the degree of demyelination and inflammation. Animals also can be examined for behavioral deficits.

The invention provides methods for designing, modeling, and identifying compounds that can bind to K6 and inhibit K6 activity. Such compounds also can be referred to as "ligands" or "inhibitors." Compounds designed, modeled, and identified by methods of the invention typically have a binding affinity of at least 1 µM (e.g., at least 500 nM, at least 100 nM, at least 50 nM, or at least 10 nM) for K6.

Compounds identified by methods of the invention can be polypeptides such as, for example, serine protease inhibitors or antibodies. Alternatively, a compound can be any suitable type of molecule that can specifically bind to K6.

By "modeling" is meant quantitative and/or qualitative analysis of K6-inhibitor structure/function based on three-dimensional structural information and K6-inhibitor interaction models. This includes conventional numeric-based molecular dynamic and energy minimization models, interactive computer graphic models, modified molecular mechanics models, distance geometry and other structure-based constraint models. Modeling typically is performed using a computer and may be further optimized using known methods.

Methods of designing ligands that bind specifically (i.e., with high affinity) to K6 typically are computer-based, and involve the use of a computer having a program capable of generating an atomic model. Computer programs that use X-ray crystallography data are particularly useful for designing ligands that can interact with K6. Programs such as RasMol, for example, can be used to generate a three-dimensional model of K6 and/or determine the structures involved in ligand binding. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures.

Methods of the invention can include, for example, providing to a computer the atomic structural coordinates for amino acid residues within K6 or a portion of K6, using the computer to generate an atomic model of K6 or a portion of K6, further providing the atomic structural coordinates of a candidate compound and generating an atomic model of the compound optimally positioned to interact with K6, and identifying the candidate compound as a ligand of interest if the compound interacts with K6. By "optimally positioned" is meant positioned to optimize hydrophobic interactions between the candidate compound and K6.

Alternatively, a method for designing a ligand having specific binding affinity for K6 can utilize a computer with an atomic model stored in its memory. The atomic coordinates of a candidate compound then can be provided to the computer, and an atomic model of the candidate compound optimally positioned can be generated.

Compounds of the invention also may be interactively designed from structural information of the compounds described herein using other structure-based design/modeling techniques (see, e.g., Jackson (1997) Seminars in Oncology 24:L164-172; and Jones et al. (1996) J. Med. Chem. 39:904-917).

Compounds and polypeptides of the invention also can be identified by, for example, identifying candidate compounds by computer modeling as interacting spatially and preferentially (i.e., with high affinity) with K6, and then screening those compounds in vitro or in vivo for the ability to reduce K6 activity or decrease inflammation and/or demyelination. Suitable methods for such in vitro and in vivo screening include those described herein.

Methods of Using K6 as a Marker for Inflammatory Conditions

Levels of K6 protein or RNA can be used to monitor therapy of inflammatory conditions, screen for the presence of an inflammatory condition, or to monitor the disease state (e.g., relapses of MS). In general, methods of the invention include detecting the level of K6 protein or a RNA encoding K6 in a biological sample from a patient (e.g., a human patient) and comparing the level of K6 protein or RNA to that from a control population (e.g., the average level of K6 from a plurality of subjects without an inflammatory condition). Methods for detecting levels of K6 protein and RNA are described below. Suitable biological samples for measuring K6 levels include, for example, blood (including whole blood, plasma, and serum), urine, and cerebrospinal fluid (CSF). Serum and CSF are particularly useful biological samples.

The presence of an inflammatory condition can be determined based on the level of K6 protein or RNA relative to the control population. Thus, it is determined if K6 protein or RNA levels are increased, decreased, or the same as that of the control population. An increase in K6 levels relative to that of the control population is indicative of an inflammatory condition. Additional factors that can be considered when diagnosing an inflammatory condition include, for example, patient history, family history, genetic factors, and/or altered neurologic examination (e.g., for MS or other neurological inflammatory condition).

The levels of K6 protein or RNA in a subject also can be used to monitor treatment. Typically, the subject's baseline level of K6 protein or RNA is obtained (e.g., before treatment) and compared to the level of K6 at various time points after or between treatments (e.g., one or more days, weeks, or months after treatment). A decrease in K6 protein or RNA levels relative to the baseline level is indicative of a positive response to treatment. Similarly, disease state in a subject can be monitored (e.g., for relapse of disease) by comparing levels of K6 protein or RNA in the subject to the subject's baseline level of K6 protein or RNA.

Detecting K6 Protein

K6 can be detected, for example, immunologically using one or more antibodies. In immunological assays, an antibody having specific binding affinity for K6 or a secondary antibody that binds to such an antibody can be labeled, either directly or indirectly. Suitable labels include, without limitation, radionuclides (e.g., $^{125}I$, $^{131}I$, $^{35}S$, $^{3}H$, $^{32}P$, $^{33}P$, or $^{14}C$), fluorescent moieties (e.g., fluorescein, FITC, PerCP, rhodamine, or PE), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting K6 can be performed in a variety of known formats, including sandwich assays, competition assays (competitive RIA), or bridge immunoassays. See, for example, U.S. Pat. Nos. 5,296,347; 4,233,402; 4,098,876; and 4,034,074. Methods of detecting K6 generally include contacting a biological sample with an antibody that binds to K6 and detecting binding of K6 to the antibody. For example, an antibody having specific binding affinity for K6 can be immobilized on a solid substrate by any of a variety of methods known in the art and then exposed to the biological sample. Binding of K6 to the antibody on the solid substrate can be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). Alternatively, the antibody can be labeled and detected as described above. A standard curve using known quantities of K6 can be generated to aid in the quantitation of K6 levels.

In other embodiments, a "sandwich" assay in which a capture antibody is immobilized on a solid substrate is used to detect the level of K6. The solid substrate can be contacted with the biological sample such that any K6 in the sample can bind to the immobilized antibody. The level of K6 bound to the antibody can be determined using a "detection" antibody having specific binding affinity for K6 and the methods described above. It is understood that in these sandwich assays, the capture antibody should not bind to the same epitope (or range of epitopes in the case of a polyclonal antibody) as the detection antibody. Thus, if a monoclonal antibody is used as a capture antibody, the detection antibody can be another monoclonal antibody that binds to an epitope that is either completely physically separated from or only partially overlaps with the epitope to which the capture monoclonal antibody binds, or a polyclonal antibody that binds to epitopes other than or in addition to that to which the capture monoclonal antibody binds. If a polyclonal antibody is used as a capture antibody, the detection antibody can be either a monoclonal antibody that binds to an epitope that is either completely physically separated from or partially overlaps with any of the epitopes to which the capture polyclonal antibody binds, or a polyclonal antibody that binds to epitopes other than or in addition to that to which the capture polyclonal antibody binds. Sandwich assays can be performed as sandwich ELISA assays, sandwich Western blotting assays, or sandwich immunomagnetic detection assays.

Suitable solid substrates to which an antibody (e.g., a capture antibody) can be bound include, without limitation, microtiter plates, tubes, membranes such as nylon or nitrocellulose membranes, and beads or particles (e.g., agarose, cellulose, glass, polystyrene, polyacrylamide, magnetic, or magnetizable beads or particles). Magnetic or magnetizable particles can be particularly useful when an automated immunoassay system is used.

Alternative techniques for detecting K6 include mass-spectrophotometric techniques such as electrospray ionization (ESI), and matrix-assisted laser desorption-ionization (MALDI). See, for example, Gevaert et al., *Electrophoresis* 22(9):1645-51, 2001; Chaurand et al., *J Am Soc Mass Spectrom* 10(2):91-103, 1999. Mass spectrometers useful for such applications are available from Applied Biosystems (Foster City, Calif.); Bruker Daltronics (Billerica, Mass.) and Amersham Pharmacia (Sunnyvale, Calif.).

Detecting K6 Ribonucleic Acid

K6 RNA can be detected, for example, by polymerase chain reaction (PCR) assays or RNA blotting techniques (e.g., Northern blotting). For example, K6 RNA can be detected in peripheral blood mononuclear cells. In general, PCR refers to amplification of a target nucleic acid, using sequence information from the ends of the region of interest or beyond to design oligonucleotide primers that are identical or similar in sequence to opposite strands of the template to be amplified. Primers are typically 14 to 40 nucleotides in length, but can range from 10 nucleotides to hundreds of nucleotides in length. PCR is described, for example in *PCR Primer: A Laboratory Manual*. Ed. by Dieffenbach, C. and Dveksler, G., Cold Spring Harbor Laboratory Press, 1995. Nucleic acids also can be amplified by ligase chain reaction, strand displacement amplification, self-sustained sequence replication or nucleic acid sequence-based amplification. See, for example, Lewis, R., *Genetic Engineering News*, 12(9):1 (1992); Guatelli et al., *Proc. Natl. Acad. Sci. USA*, 87:1874-1878 (1990); and Weiss, R., *Science*, 254:1292 (1991).

For example, the levels of K6 mRNA can be detected using reverse transcription-polymerase chain reaction (RT-PCR). Real-time quantitative PCR can be performed using, for example, the ABI PRISM 7700 Sequence Detection System and Taqman fluorogenic probes, or the LightCycler™ instrument from Roche.

Articles of Manufacture

Antibodies having specific binding affinity for K6 can be combined with packaging material and sold as a kit for detecting K6 from biological samples, treating inflammatory conditions, monitoring therapy of inflammatory conditions, or monitoring disease relapses (e.g., of MS). Antisense oligonucleotides that inhibit expression of K6 also can be combined with packaging material and sold as a kit for treating inflammatory conditions. Components and methods for producing articles of manufactures are well known. The articles of manufacture may combine one or more anti-K6 antibodies or fragments thereof or one or more antisense oligonucleotides as described herein. In addition, the articles of manufacture may further include reagents such as secondary antibodies, buffers, indicator molecules, solid phases (e.g., beads), additional anti-inflammatory agents, and/or other useful reagents for detecting K5 from biological samples, treating inflammatory conditions, monitoring therapy of inflammatory conditions, or monitoring disease relapses. The anti-K6 antibody or antisense oligonucleotide can be in a container, such as a plastic, polyethylene, polypropylene, ethylene, or propylene vessel that is either a capped tube or a bottle. In some embodiments, the anti-K6 antibody can be included on a solid phase such as a handheld device for bedside testing. Instructions describing how the various reagents are effective for treating inflammatory conditions, monitoring therapy of inflammatory conditions, or monitoring disease relapses also may be included in such kits.

The invention will be further described in the following examples, which do not limit the scope of the invention described in the claims.

EXAMPLES

Materials and Methods

Human multiple sclerosis (MS) lesions: This study was performed on paraffin-embedded and formalin-fixed archival material from autopsies with clinically and pathologically confirmed MS. Paraffin-embedded 5-µm sections were stained with routine neuropathological stains, including hematoxylin-eosin, Luxol fast blue/periodic acid Schiff (LFB/PAS), and Bileschowski silver impregnation axonal stain, as well as immunocytochemistry for the following markers: anti-proteolipid protein (MCA839, Serotec, Raleigh, N.C.), anti-myelin oligodendrocyte glycoprotein (Dr. S. Piddlesden, University of Cardiff, UK), and anti-K6 (see below). All cases underwent detailed neuropathological examination and were screened for white matter demyelinating lesions. Demyelinating activity was classified according to recently established criteria (Lassmann et al. (1998) *J. Neuroimmunol.* 86:213-217). Active demyelinating lesions were diffusely infiltrated by macrophages containing myelin proteins as markers of recent and ongoing myelin phagocytosis. Inactive demyelinated lesions were completely demyelinated without signs of remyelination.

Theiler's murine encephalomyelitis virus (TMEV) model of MS: Four- to 8-week-old female SJL/J (H-$2^S$) mice (Jackson Laboratories, Bar Harbor, Me.) were intracerebrally injected with $2\times10^6$ plaque-forming units (p.f.u.) of the Daniel's strain of TMEV, in a 10 µl volume. Care and handling of the mice was in accord with the guidelines of both the NIH and the Mayo Clinic Animal Care and Use Committee. At 30, 45, 90, 120 and 180 days post-infection, mice were anaesthetized with pentobarbital (150 mg/kg) and perfused with 4% paraformaldehyde. Spinal cords were blocked transversely at 1 mm, cryoprotected in 25% sucrose, frozen on dry ice and sectioned transversely at 20 pm. Alternatively, blocks were embedded in paraffin and cut at 5 pm. Unfixed spinal cords were obtained at the same time points, snap frozen and stored at −70° C. until analysis.

MOG-induced EAE: Marmosets were obtained from Clea, Japan, or the New England Regional Primate Research Center, and housed in the primate colony at the University of California, San Francisco, according to all guidelines of the Institutional Animal Care and Use Committee. EAE was induced by immunization with 100 pg of recombinant rat αMOG (extracellular domain, containing amino acids 1-125), emulsified in complete Freund's adjuvant (CFA), followed by intravenous injection of $10^{10}$ killed *Bordetella pertussis* organisms on the day of immunization and 48 h later. Clinical signs of EAE developed between 19 and 23 days after immunization. Animals were euthanized with worsening signs during the acute phase (40-42 days after immunization), under deep barbiturate anesthesia, by intracardiac perfusion with 4% paraformaldehyde. Slabs of spinal cord were processed for paraffin and 5-pm thick sections were stained with hematoxylin and eosin, or processed to localize K6 immunoreactivity.

Immunohistochemistry: Immunostaining of K6 in mouse, marmoset and human tissue sections was accomplished using purified biotin. Rat conjugated or unconjugated mouse monoclonal K6 anti-brain antibodies (Scarisbrick et al. (2000) *Glia* 30:219-230) or rabbit polyclonal antibodies (Blaber et al. (2002) *Biochem.* 41:1165-1173), each of which yielded identical staining patterns in the tissues examined. Cell mixture-specific markers used in double-labelling studies were: anti-glial fibrillary acidic protein (anti-GFAP); Cy3 conjugate (Sigma, St Louis, Mo.); rat anti-mouse F480 IgG (Serotec); biotinylated isolectin B4 (Sigma); rat anti-mouse CD4; or rat biotinylated antiTricine mouse CD8b.2 (PharMingen, San Diego, Calif., USA). Bound antibodies were detected using mouse adsorbed, fluorochrome-conjugated, species appropriate secondary antibodies (Jackson ImmunoResearch, West Grove, Pa.), or with the avidin-biotin immunoperoxidase technique (Vector Laboratories, Burlingame, Calif.). In all cases, control for the specificity of immunostaining included staining as above with the omission of primary antibody.

In situ hybridization: Examination of K6 and proteolipid protein (PLP) mRNA expression in TMEV-infected mouse spinal cord was accomplished using digoxigenin (DIG)-labelled cRNA probes. The K6-specific probe was prepared by transcription from the K6 cDNA construct pM514, containing 435 base pairs (bp) of rat K6 (nucleotides 220-655), and the PLP probe from construct pGPLP-1, containing 250 bp of mouse PLP (nucleotides 34-285). Hybridization was performed as described previously (Scarisbrick et al. (1999) *J. Neurosci.* 19:7757-7769), and in some cases hybridized slides were further processed to localize K6-IR, GFAP-IR or Isolectin $_{B4}$-IR, as detailed above.

Recombinant K6: Recombinant rat K6 (r-K6) was expressed in the baculovirus system, as described in detail elsewhere (Blaber et al. supra). Briefly, the zymogen form of r-K6 with a 44 amino acid synthetic pro-sequence including an enterokinase (EK) recognition sequence and 6× histidine tag, was expressed in baculovirus expression system, purified in a single step utilizing the His tag fusion and nickel affinity resin and shown to be 98% pure by Coomassie Blue-stained SDS-PAGE. The homogeneity of purified K6 was confirmed using N-terminal sequencing, mass spectrometry and size exclusion high-performance liquid chromatography. After activation by EK (Roche Diagnostics Corp., Indianapolis, Ind.), mature r-K6 was further purified by G-50 superfine (Pharmacia Corp., Kalamazoo, Mich.) size exclusion chromatography, to eliminate enterokinase and the cleaved propeptide.

Degradation of myelin basic protein and MOG by K6: Rat myelin basic protein (MBP) was isolated from adult rat and was incubated with r-K6 in 40 mM phosphate, 150 mM NaCl (pH 7.4) at a 100:1 mass ratio. The final concentration of r-K6 in the reaction was 35.3 pM. The reaction mixture was incubated at 37° C., time points were taken at 0, 1, 4, and 16 hours post-monoclonal incubation, snap frozen on dry ice and kept at −80° C. The digestion pattern of rat MBP was analyzed by loading 10 pl of sample (equivalent to 5 pg of rat MBP) per lane on 16.5% SDS-PAGE under reducing conditions.

Recombinant rat myelin oligodendrocyte glycoprotein (αMOG), as described above, was incubated with r-K6 in the same conditions as rat MBP, except that the final concentration of αMOG was 31.5 pM. The digested sample was resolved on 16.5% Tricine SDS-PAGE for analysis in the same manner.

Oligodendrocyte cell culture systems: Two oligodendrocyte culture systems were used: purified oligodendrocyte progenitors and the bipotential CG4 oligodendrocyte cell line. Mixed primary glial cell cultures were prepared from the telencephala of PN-1 Sprague-Dawley rats, and OL progenitors obtained from these by overnight shaking and differential adhesion as described in detail in McCarthy and De Vellis ((1980) *J. Cell. Biol.* 85:890-902). Purified OL progenitors were plated onto poly-L-ornithine coated glass coverslips at a density of $20 \times 10^3/cm^2$ and grown in Dulbecco's minimal essential media (DMEM) containing: 4.5 mg/ml glucose, 2 mM glutamine, N2 supplement (Gibco-BRL, Grand Island, N.Y.), 5 µg/ml insulin, 30 nM T3, 10 ng/ml biotin, 50 U/ml penicillin/streptomycin, 0.1 mg/ml sodium pyruvate (Sigma), and 10 ng/ml each of PDGF-AA and bFGF, (R &D Systems, Minneapolis, Minn.). Undifferentiated CG4 cells were grown in Ham's DMEM F12 containing the same supplements.

To examine the effects of excess exogenous r-K6, telencephalon-derived or CG4 O2A progenitor cells were differentiated toward the oligodendrocyte lineage by replacement of mitogenic factors, PDGF and FGF, with 0.05% bovine serum albumin (BSA). The effect of r-K6 on differentiated oligodendrocytes was examined by exposing cells differentiated for 72 hours to 1 or 10 µg/ml (40 or 400 nM) of r-K6 for an additional 72 hours, with media changes containing fresh r-K6 every 24 hours. To evaluate the effect of r-K6 on oligodendrocyte differentiation, progenitors were plated in differentiation media as above, but media was supplemented with 1 or 10 µg/ml of r-K6 after a 30 minute culture period, allowing for cellular attachment. As above, cells were then allowed to differentiate for a further 72 hours before analysis. To distinguish between cell surface or substrate effects, in a third paradigm, CG4 O2A cells were treated in one of three ways: (i) cells were plated and media changed to differentiation media containing 1 or 10 µg/ml of r-K6 30 minutes after plating; (ii) cells were resuspended in and incubated for 30 minutes with 1 or 10 µg/ml of r-K6, spun down and resuspended in protease-free differentiation media before plating; or (iii) prior to plating, the polyornithine coated coverslip was incubated for 1 hour at 37° C. with 1 or 10 µg/ml of r-K6. Cells were differentiated for a further 24 hours prior to analysis. Control wells were supplemented with an equal volume of vehicle (40 mM NaOAc, 100 mM NaCl, pH 4.5) alone. To visualize oligodendrocyte processes, coverslips were briefly rinsed in HEPES-buffered saline solution (HBSS), and stained live in HBSS containing 1% BSA for the presence of cell surface sulphatide, using the monoclonal antibody, and fluorescein (FITC)-conjugated secondary antibodies (Jackson ImmunoResearch). Labelled cells were fixed in 2% paraformaldehyde and coverslipped with 90% glycerol (pH 8.0) containing 10 µg/ml of the nuclear stain bisbenzamide (Sigma).

In each cell culture paradigm, process outgrowth and cell number were evaluated from six ($165 mm^2$) fields per coverslip, which were imaged digitally (40× objective) using an Olympus AX70 microscope fitted with a SPOT color digital camera (Diagnostic Instruments, Inc., Sterling Heights, Mich.). The number of oligodendrocyte O4-immunoreactive processes that crossed horizontal lines of a 0.25 inch grid superimposed on each image were counted for each field.

Additionally, in each field counts were also made of the total number of O4-positive cells and all cells stained with bisbenzamide. On average, 120 cells were counted per culture condition in each experiment. The mean and standard error of counts from triplicate wells were calculated and analyzed by one-way analysis of variance and the Student Newman Keuls (SNK) post hoc test. All experiments were performed in triplicate and repeated at least twice using independent cell culture preparations.

Overexpression of K6 in CG4 cells: To prepare the green fluorescent protein (GFP)-rat K6 construct, the full-length K6 clone, without a stop codon, was amplified by polymerase chain reaction from vector SB12-42B, and subcloned in-frame with the cycle 3 GFP protein of pcDNA3.1/CT-GFP-TOP0 (Invitrogen, Carlsbad, Calif.). For cellular transfection, vectors containing the K6-GFP construct, or GFP alone, were digested with BglII, ethanol precipitated and resuspended in sterile water. Proliferating CG4 cells grown on polyornithine-coated 60 mm dishes at a density of $2 \times 10^5$ per 35 mm well were transfected with 2 μg of DNA, using FuGENE 6 reagent (Roche Diagnostics). Cells successfully transfected were identified by expression of cycle 3 GFP when viewed with a 40× objective on an inverted Olympus IX70 microscope fitted with a FITC filter set. GFP-positive cells were imaged digitally using both fluorescence and phase microscopy, at 24, 48 and 96 hours post-transfection, and the number of processes was evaluated by counting those that crossed a superimposed 0.25 inch grid. At each time point the number of processes associated with cells transfected with K6-GFP or GFP alone were compared using the Mann-Whitney rank sum test.

Expression and crystallization of K6 and data collection: Mature active human K6 (hK6) was expressed and purified from a baculovirus/insect cell line system essentially as described for the rat K6 homolog. Purified hK6 was concentrated to 20 mg/mL in 40 mM sodium acetate, 100 mM NaCl, and 20 mM benzamidine, pH 4.5. Crystallization conditions were identified using a hanging-drop sparse-matrix screen of precipitants, salts, and pH conditions (Hampton Research, Laguna Niguel, Calif.). Diffraction quality crystals grew from 30% (w/v) PEG 4000, 0.2 M magnesium chloride hexahydrate, and 0.1 M Tris hydrochloride, pH 8.5 after two weeks incubation at 4° C. X-ray intensity data were collected at 103 K from a single crystal (0.5×0.2×0.05 mm) with a Rigaku imaging plate area detector R-Axis IIc using Cu—Kα radiation. Data were processed and scaled using DENZO and SCALEPACK 27,28. This crystal diffracted to at least 1.75 Å. The space group was tentatively identified as orthorhombic P212121 with cell constants a=39.1 Å, b=62.1 Å, c=85.8 Å. Based upon a molecular mass of approximately 29 kDA for hK6, a Matthews coefficient Vm=1.80 Å3/Da suggested a single molecule in the asymmetric unit 29.

Molecular Replacement and Structure Refinement: Initial phases were calculated by molecular-replacement using Atlantic salmon trypsin (PDB code 1A0J) as a search model and the Crystallography & NMR System (CNS) software package 30. The rotational search resulted in a single peak 8σ above the noise level, and a subsequent translational search in the P212121 space group of the correctly rotated model resulted in a single peak 4σ above the noise level. The Rcryst was 47.3% after rigid body refinement of this initial solution. A 3 Å 2Fobs—Fcalc SIGMAA-weighted composite annealed omit map (5% of data omitted) was calculated and the structure was built and refined through alternating cycles using the graphic program O 31 and CNS. All refinements were performed by simulated annealing using a maximum likelihood target, and this cyclic procedure was repeated several times with gradual increase of the resolution to 1.75 Å. A random selection of 3% of the data was assigned for calculation of Rfree and was not included in the refinement. Solvent molecules were added at the last stage of refinement at stereochemically reasonable positions.

Generation of hK6 Specific Monoclonal Antibodies— Monoclonal antibodies recognizing K6 were generated using human recombinant K6 expressed in the baculovirus system. Enterokinase activated hK6 was emulsified in equal ratios of Complete Freund's Adjuvant (CFA) and 0.01M phosphate buffered saline (PBS), to a final concentration of 500 μg per ml. Balb/c mice (Jackson Laboratories, Bar Harbor, Me.), were immunized in at two sites subcutaneously, and at the base of the tail, with a total of 200 μl of the CFA emulsion. After 30 days, each mouse was given a subcutaneous boost of 50 μg hK6 dissolved in 100 μl PBS. Six days after the boost, splenic lymphocytes were fused with myeloma cells. The protocol used for generation of B cell hybridomas followed standard procedures (Faedas de St. Groth and Scheidegger, 1980). Briefly, spleens were removed from mice and single-cell suspensions were prepared with red blood cells lysed with ammonium chloride buffer. Splenic lymphocytes and F/O meyeloma cells (non-secreting myeloma derived from sp2/0 balb/c myeloma cells), were mixed at a 5:1 ratio and centrifuged to form a pellet. The cell pellet was resuspended in 1 ml of a 50% solution of polyethylene glycol 1540, then incubated at 37° C. for 90 seconds. Cells were washed and resuspended in fresh media, and 100 μl aliquots were added to the wells of microtiter plates. After 24 hrs, 100 μl culture medium supplemented with 1 M hypoxanthine (HT), 4 mM aminopterin, and 0.16 M thymidine (HAT), were added to each well. Every 3-4 days thereafter, 100 μl culture medium was replaced with 100 μl fresh medium containing HAT, HT, and complete medium without HAT, successively over a period of approximately 14 days. Upon reaching 75% confluency the culture supernatants were screened by ELISA for the presence K6-specific antibody, using recombinant hK6 coated plates Immunolon II plates or recombinant human kallikrein 3 (hK3) coated plates, as a negative control using standard techniques. K6-specific hybridomas were then cloned in limiting dilution cultures at 1 cell per microtiter well. Balb/c spleen cells served as feeder layer cells for fusion and cloning microtiter plates ($3 \times 10^5$ per well). Fused cells were grown in 96 well plates in Iscove's Modified Dulbeco's Medium, containing 10.0% Fetal Bovine Serum. The supernatants of these clones were screened for K6-reactivity by ELISA (as above), and K6-specific clones were subcloned at 0.3 cells per microtiter well. The supernatants of subclones were screened by ELISA for K6-reactivity and selected subclones expanded. K6-specific hybridomas were grown in roller bottles in serum free media and the IgG fraction purified using Protein G (Pharmacia). Purified antibodies were isotyped as IgG or IgM using a mouse monoclonal antibody isotyping kit (IsoStrip, Boehringer Mannheim, Indianapolis, Ind.). Two monoclonal generated in this fashion, K6-1 and K6-2, are IgG-$1_K$ specific and recognize both rodent and human recombinant K6. Unless otherwise specified all reagents were obtained from Sigma (St. Louis, Mo.).

Example 1

K6 is Abundantly and Differentially Expressed in the Adult Human CNS

The level of K6 mRNA in adult human brain and peripheral tissues was determined. Radiolabeled human K6 cDNAs were hybridized to a dot blot containing human RNA from 43 different regions, including the brain (rows A and B) and peripheral tissues (rows C to F). The highest levels of K6 mRNA were present in the spinal cord (B7) and medulla oblongata (A8) (see Table 1). In contrast, the level of K6 mRNA in samples of most peripheral tissues was low, with the exception of the kidney (E1), where the level of K6 mRNA detected was similar to that detected in the cord (B7). Low levels of K6 mRNA also were present in human thymus (E5), spleen (E4) and lymph node (E7).

TABLE 1

Quantification of K6 mRNA present in human brain regions and peripheral tissues.

| RNA Source | K6 |
| --- | --- |
| A1 - Whole Brain | 18* |
| A2 - Amygdala | 15 |
| A3 - Caudate Nucleus | 19 |
| A4 - Cerebellum | 8 |
| A5 - Cerebral Cortex | 20 |
| A6 - Frontal Lobe | 43 |
| A7 - Hippocanipus | 57 |
| A8 - Medulla Oblongata | 102 |
| B1 - Occipital Pole | 9 |
| B2 - Putamen | 21 |
| B3 - Substantia Nigra | 33 |
| B4 - Temporal Lobe | 13 |
| B5 - Thalamus | 29 |
| B6 - Sub-thalamic Nucleus | 34 |
| B7 - Spinal Cord | 100 |
| C1 - Heart | 7 |
| C2 - Aorta | 5 |
| C3 - Skeletal Muscle | 9 |
| C4 - Colon | 12 |
| C5 - Bladder | 12 |
| C6 - Uterus | 13 |
| C7 - Prostate | 13 |
| C8 - Stomach | 16 |
| D1 - Testis | 13 |
| D2 - Ovary | 9 |
| D3 - Pancreas | 9 |
| D4 - Pituitary Gland | 16 |
| D5 - Adrenal Gland | 16 |
| D6 - Thyroid Gland | 19 |
| D7 - Salivary Gland | 14 |
| D8 - Mammary Gland | 17 |
| E1 - Kidney | 87 |
| E2 - Liver | 23 |
| E3 - Small Intestine | 15 |
| E4 - Spleen | 9 |
| E5 - Thymus | 23 |
| E6 - Peripheral Leukocyte | 14 |
| E7 - Lymph Node | 17 |
| E8 - Bone Marrow | 15 |
| F1 - Appendix | 9 |
| F2 - Lung | 20 |
| F3 - Trachea | 9 |
| F4 - Placenta | 9 |

*The relative optical density produced by hybridization of a human K6 cDNA probe to each RNA sample was expressed as percent of the signal produced in the spinal cord.

Example 2

K6 is Robustly Expressed by Oligodendrocytes

Oligodendrocytes in all human brain regions were examined by immunohistochemistry as described in the Methods and Materials section, and were found to be densely K6-immunoreactive. The immunoreactive oligodendrocytes included those of the corpus callosum, the optic nerve, and the subcortical white matter. The localization of K6 to oligodendrocytes, but not to astrocytes, in white matter of the adult brain suggests this enzyme plays a role in normal oligodendrocyte homeostatic mechanisms.

Example 3

The Expression of K6 by Oliodendrocytes is Upregulated by Injury

Figure 1:
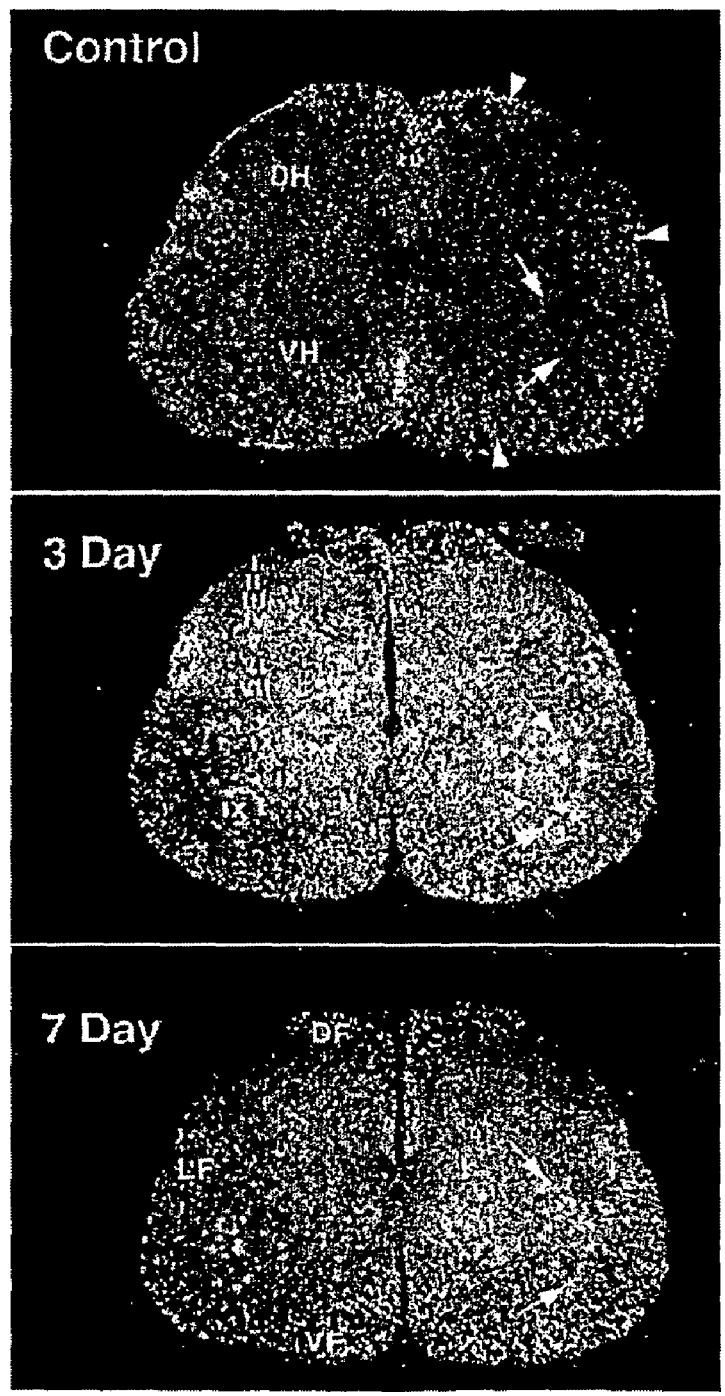
FIG. 1 contains dark-field photomicrographs showing the autoradiographic localization of K6 mRNA in a transverse section through the spinal cord of a control rat, and in parallel sections of paired experimental rats at 3 and 7 days after intraperitoneal injection of KA. DF, LF, and VF: Dorsal, Lateral and Ventral funiculi of the white matter.

Levels of K6 mRNA in adult rat spinal cord were increased in both white and gray matter following kainic acid (KA)-induced excitotoxic injury. Dark-field photomicrographs (FIG. 1) show the autoradiographic localization of K6 mRNA in a transverse section through the spinal cord of a control rat, and in parallel sections of paired experimental rats at 3 and 7 days after intraperitoneal injection of KA. By three days after KA treatment, K6 mRNA was 2-fold higher in the white matter and 1.5-fold higher in the dorsal horn (DH) and ventral horn (VH) of the spinal cord gray matter, compared to controls ($P<0.05$). A hemisection of spinal cord white matter from an adult rat revealed a 5-fold increase in K6 mRNA expression by oligodendrocytes by 72 hr-post lesion compared to controls. These findings support the hypothesis that K6 is involved in the response of oligodendrocytes to injury, and suggest that K6 may participate in myelin turnover.

Example 4

K6 is Elevated at Sites of Neuroinflammation and Demyelination

Figure 2:
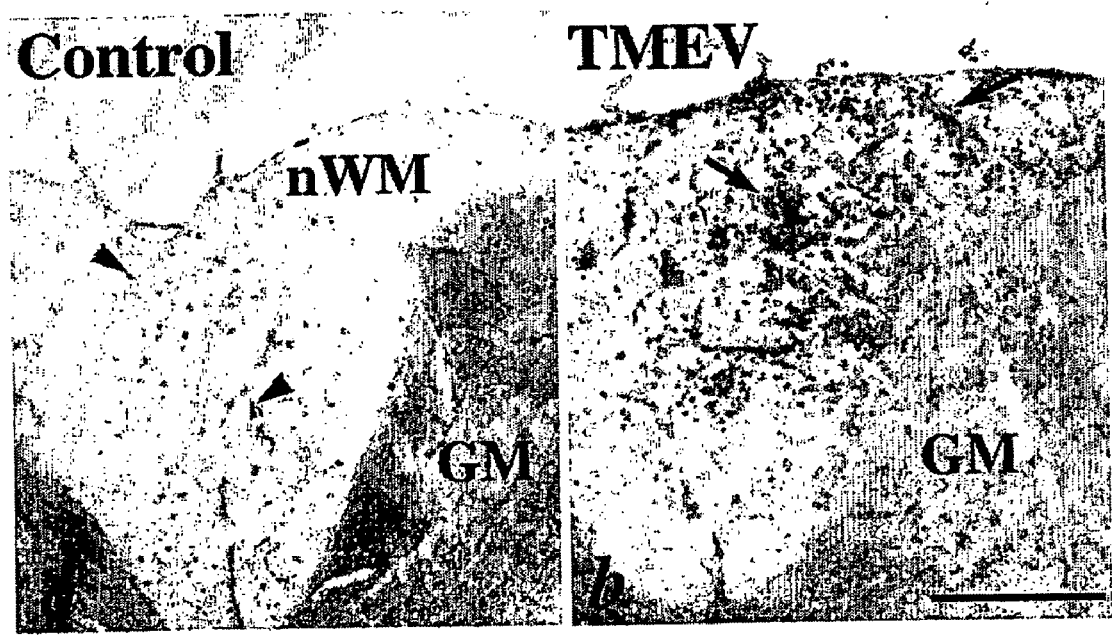
FIG. 2 contains photomicrographs of normal white (nWM and gray matter (GM) in the spinal cord of control animals (left panel) and in association with inflammatory cells at sites of active demyelination 180 days following TMEV infection (right panel). Oligodendrocytes are marked by arrows; bar=200 µm.

K6 immunoreactivity was dense in oligodendrocytes in areas of normal white and gray matter in the spinal cord of control animals (FIG. 2A), and in association with inflammatory cells at sites of active demyelination 180 days following TMEV infection (FIG. 2B).

A section of spinal cord from a marmoset with αMOG-induced EAE showed foci of inflammatory cells, seen as areas of hyper-cellularity in hematoxylin/eosin counter-stained sections. In an adjacent section, K6 immunoreactivity was associated with oligodendrocytes in normal white matter and with inflammatory cells at sites of active demyelination.

Figure 3:
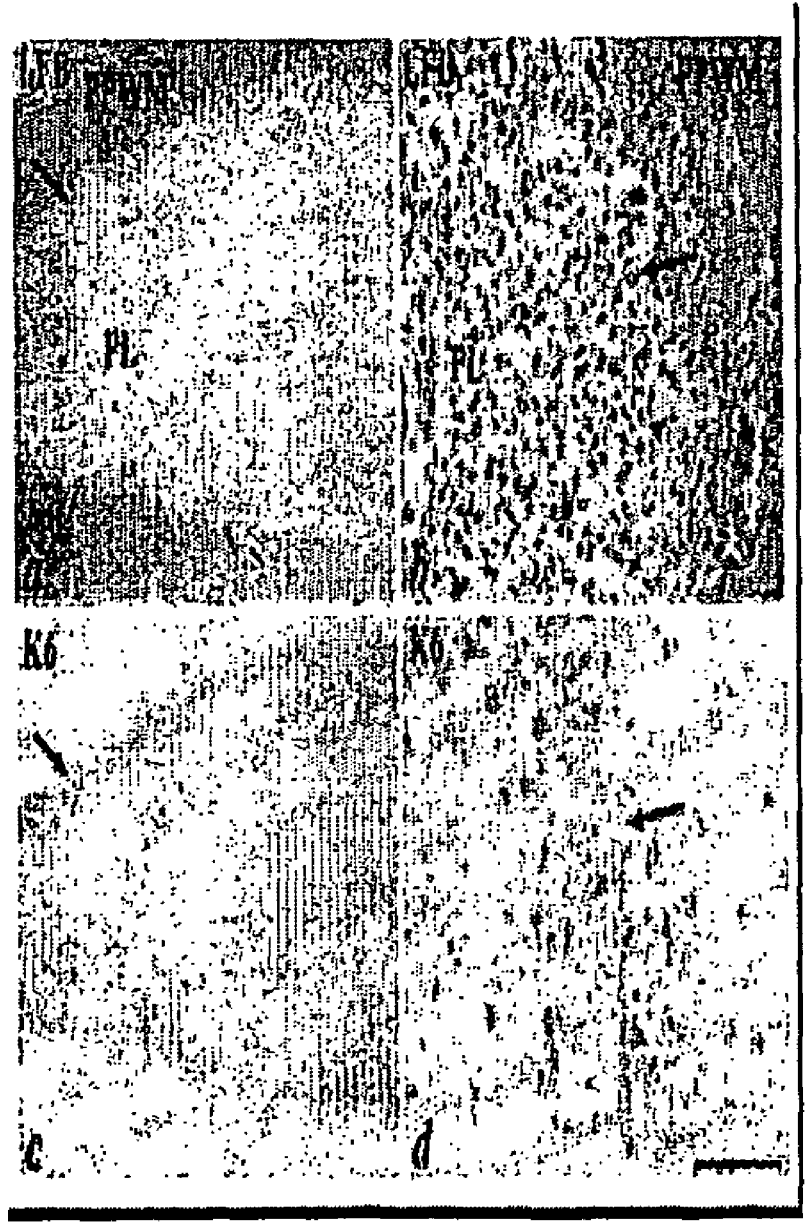
FIG. 3A is a photomicrograph of a well-demarcated chronic active MS lesion, (luxol fast blue/periodic acid Schiff's (LFB/PAS) myelin stain).
FIG. 3B is a higher magnification view of FIG. 3A.
FIG. 3C is a parallel section to 3A, stained for K6-IR, which is upregulated within inflammatory cells at the border between the plaque (PL) and periplaque white matter (PPWM), on the side of the lesion (arrow).
FIG. 3D is a higher magnification view of FIG. 3C. bar=200 µm.

Human brain sections from autopsies with clinically and pathologically confirmed MS were stained with LAF/PAS. These studies revealed a well-demarcated chronic active MS lesion (FIG. 3A, shown at a higher magnification in FIG. 3B). The plaque (PL) showed a complete loss of myelin compared to the periplaque white matter (PPWMK. Immunohistochemical analysis demonstrated that K6 was upregulated within inflammatory cells at the border between the PL and the PPWM, on the side of the lesion (FIG. 3C, shown at a higher magnification in FIG. 3D). The highest levels of K6 immunoreactivity were associated with inflammatory cells at the PL/PPWM border. K6 immunoreactivity also was upregulated within reactive astrocytes.

Example 5

K6 is Expressed by Macrophages, in Addition to Both CD4 and CD8 Inflammatory Cells at Sites of Demyelination in the TMEV-Infected Mouse Spinal Cord The earliest known event in the pathogenesis of MS lesions is transendothelial migration of lymphocytes into the CNS. As discussed above, K6 immunoreactivity in both TMEV and αMOG induced EAE, as well as in active human MS lesions, is dense in inflammatory cells at sites of demyelination. The potential role of K6 in demyelinating disease was therefore examined.

K6 was localized by immunofluorescence at sites of demyelination in mouse spinal cord white matter, 90 days post-infection with TMEV. The white matter sections also were stained with markers for inflammatory cells, including F480, CD4, and CD8. This double-labeling technique demonstrated high levels of K6 immunoreactivity associated with macrophages, as well as CD4 and CD8 T cells. K6 immunoreactivity was not upregulated in oligodendrocytes in areas of demyelination, at least relative to the high levels observed in inflammatory cells.

Example 6

K6 is Elevated in the Sera of TMEV Infected Mice

Figure 4:
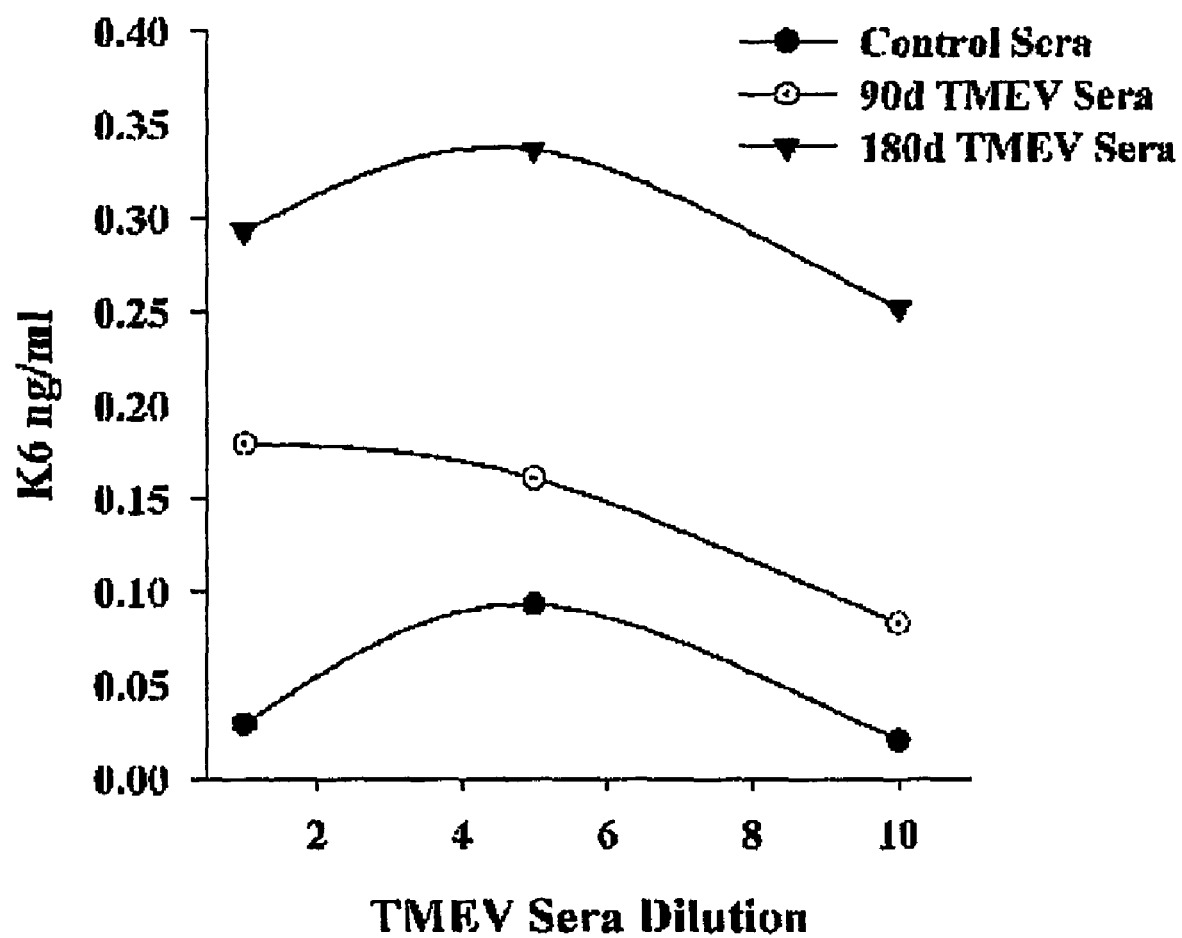
FIG. 4 is a graph of the amount of K6 detected in sera from uninfected mice (control, solid circle), or in mice at 90 and 180 days post-TMEV infection (open circles and solid triangles, respectively).

A quantitative capture enzyme-linked immunosorbent assay (ELISA) was used to determine the amount of K6 in sera from uninfected mice (control), or in mice at 90 and 180 days post-TMEV infection (FIG. 4). There was about a 3.5-fold increase in the amount of K6 in sera at 180 days following infection, compared with control sera.

Example 7

Recombinant K6 Degrades Components of the Blood Brain Barrier

Figure 5:
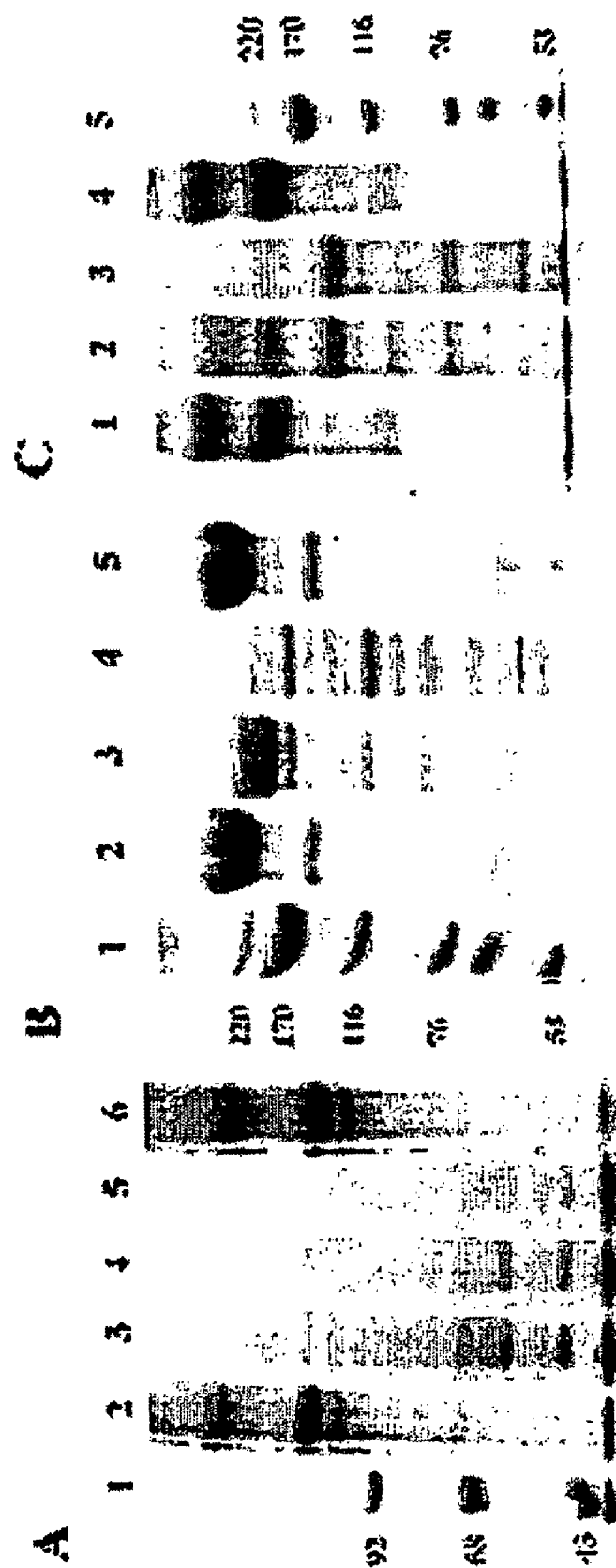
FIGS. 5A-5B are photographs of 7.5% SDS-PAGE (reducing) gels stained with Coomassie blue that depict degradation collagen type I (5A), fibronectin (5B), and laminin (5C).
In FIG. 5C, lanes 1-5 are laminin+K6 0 hr; 1 hr; 16 hr; laminin control 16 hr, molecular mass standards, respectively.

To determine whether K6 may participate in the migration of inflammatory cells into the CNS by degrading the BBB basal lamina, enzymatic studies of K6 with collagen, fibronectin, and laminin were conducted. K6 rapidly degraded all three BBB components. Collagen type I was degraded within 5 minutes of K6 addition (FIG. 5A, lane 3 compared to lane 2). Fibronectin was partially degraded within 1 hour of K6 addition and was completely degraded by 24 hours (FIG. 5B, lanes 3 and 4 compared to lane 2). Laminin was partially degraded by one hour after K6 addition, and was completely degraded by 16 hours (FIG. 5C, lanes 2 and 3 compared to lane 1). K6 therefore may play a role in the migration of inflammatory cells into the CNS.

Example 8

Recombinant K6 can Degrade Myelin Specific Proteins

Figure 6:
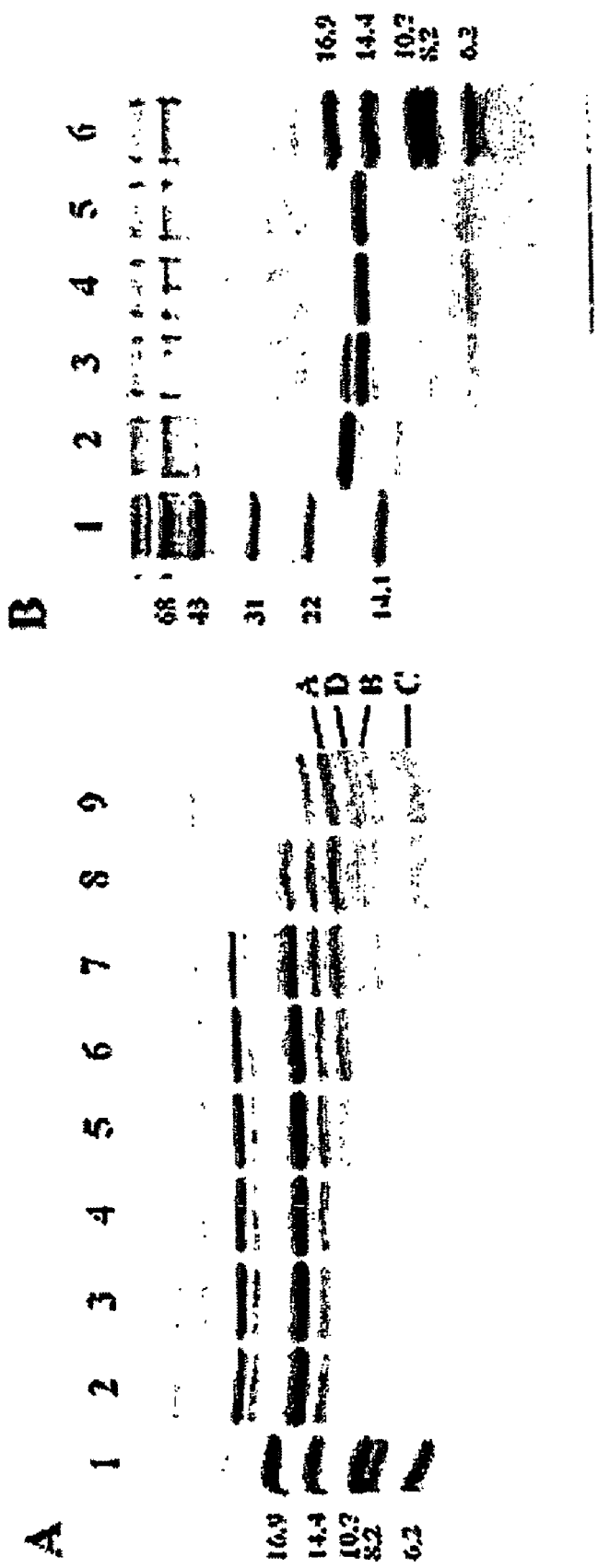
FIGS. 6A and 6B are photographs of 16.5% Tricine SDS PAGE gels showing degradation of rat myelin basic protein by K6 (11A) and rat αMOG external fragment (residues 1-125) by K6.

K6 is a trypsin-like serine protease that specifically hydrolyses proteins after Arginine residues. Given this broad substrate specificity, it is likely that increased levels of K6 at sites of CNS inflammation will have widespread degradative functions, including the breakdown of myelin specific proteins. This hypothesis was tested in vitro by examining the ability of K6 to degrade MBP and the 125 amino terminal fragment of αMOG. MBP was partially degraded by 10 minutes after addition of K6, and showed much greater levels of degradation at 30 minutes and 60 minutes (FIG. 6A, lanes 7-9). αMOG was partially degraded by 1 hour after addition of K6, and was completely degraded by 4 hours (FIG. 6B, lanes 3 and 4).

Example 9

Figure 7:
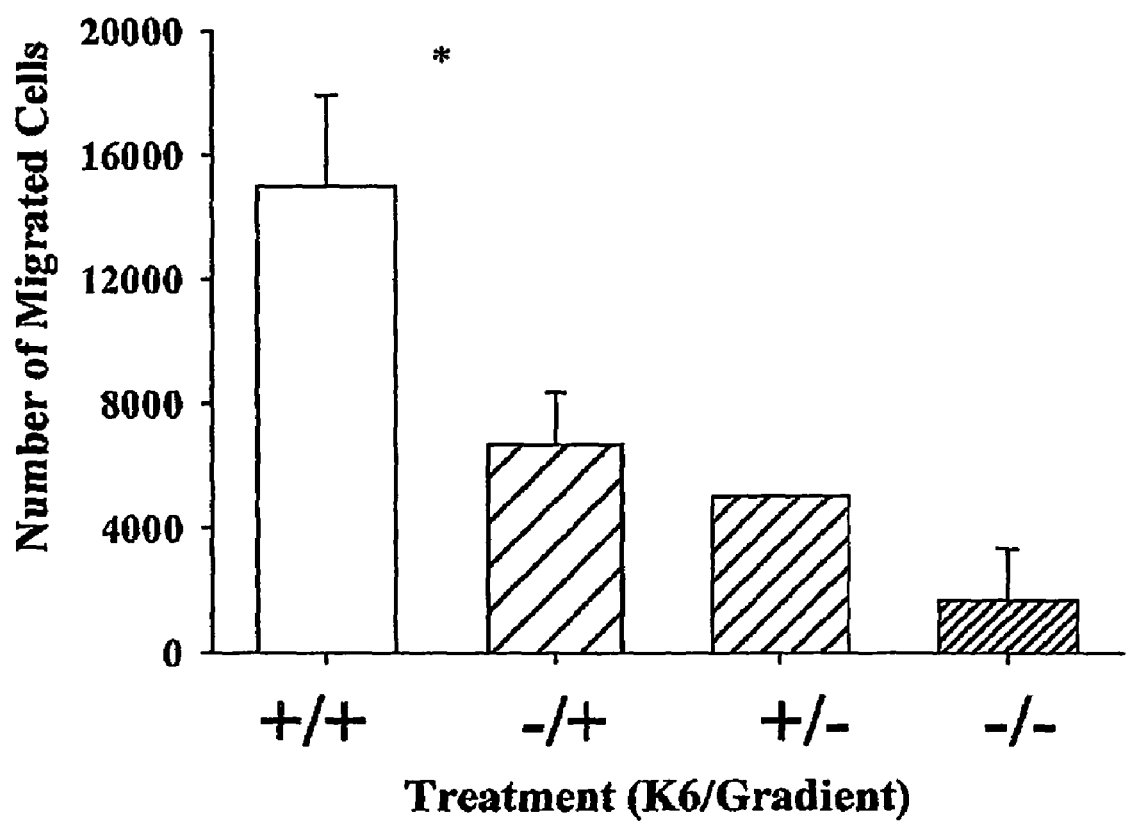
FIG. 7 is a graph of the number of migrated cells as a function of treatment. *$P<0.05$, SNK.

K6 is Capable of Enhancing the Migration of Inflammatory Cells Across Blood Brain Barrier ECM The migration of human peripheral blood mononuclear cells (PBMC) was assessed. Matrigel-coated 8 mm pore size membranes were pretreated with 10 µg/ml recombinant K6 (r-K6) for 24 hr prior to the addition of cells, using fetal calf serum (FCS) as the chemoattractant. An 8 hour incubation period in the presence of a FCS gradient revealed that pretreatment of a Matrigel membrane with r-K6 significantly enhanced PBMC migration (FIG. 7; $P<0.05$).

Example 10

K6 is Important in Normal Oligodendrocyte Development

Two oligodendrocyte culture systems, primary "shaken" oligodendrocytes (McCarthy and De Vellis, supra) and the CG4 oligodendrocyte cell line (Louis et al. (1992) *Glia* 6:30-38), in addition to sensitive immunohistochemical, immunoblot and ELISA assays, were used to show that K6 is expressed by oligodendrocyte progenitors (O2A) right through to maturation in vitro. While abundant at all stages of the lineage, the distribution of K6 was altered with maturation, becoming more abundant in association with distal processes. This dynamic expression pattern points to roles for K6 in the development and maintenance of the mature myelinating phenotype.

Using immunohistochemistry, K6 and oligodendrocyte lineage markers were shown to colocalize in purified cultures of oligodendrocyte progenitors isolated from the postnatal rat brain, and in the CG4 cell line at the O4 (sulfatide, pro-oligodendrocyte, and O1 (galactocerebroside, immature/mature; stages of differentiation. Both A2B5$^+$ (ganglioside) oligodendrocyte progenitors and A2B5$^-$ pre-progenitors were K6 immunoreactive. It is noted that microglia also were associated with high levels of K6 immunoreactivity. In CG4 cells at the O4 and O1 stages of maturity, K6 immunoreactivity was most abundant in the distal processes.

Figure 8:
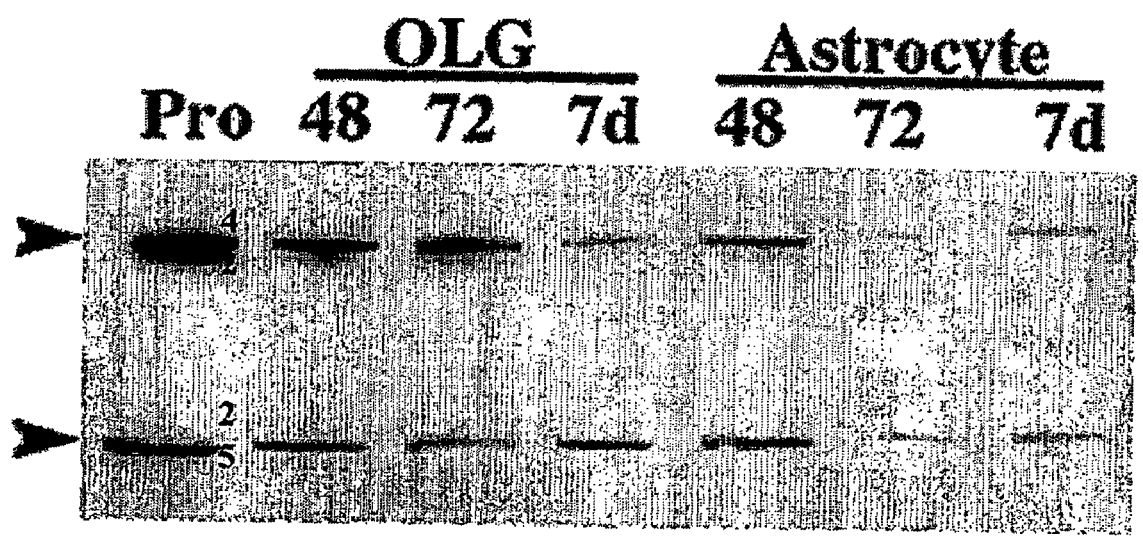
FIG. 8 is a Western blot of K6 (arrow at 25 kDa) in proliferating OLGs (Pro), and after 48 hr, 72 hr, and 7 days in culture.
Figure 10:
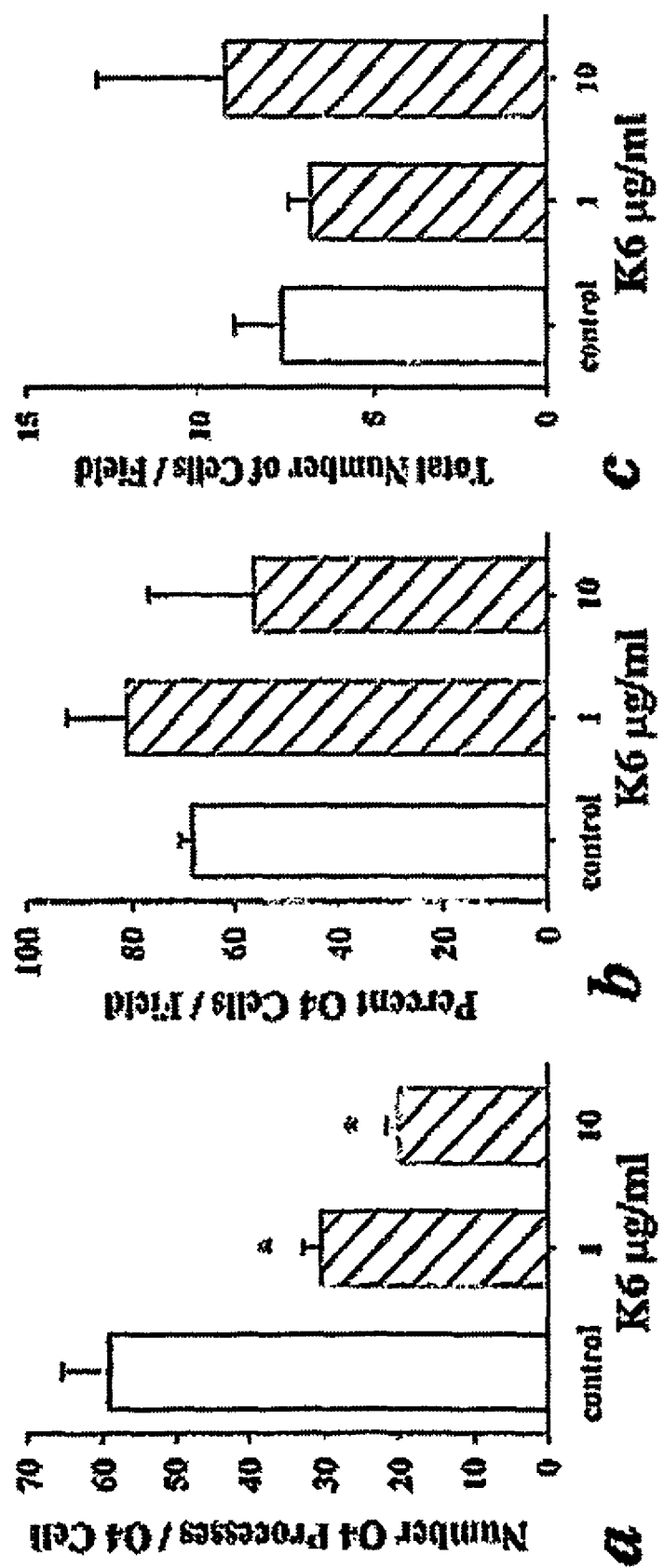
FIGS. 10A-10C are graphs of the number of differentiated oligodendroglia after exposure to different amounts of recombinant K6 in vitro. *$p<0.05$, SNK.

The developmentally regulated expression of K6 in cultured oligodendrocytes was confirmed by immunoblotting (FIG. 8). The highest levels of K6 (25 kDa) were observed in proliferating oligodendrocytes (Pro), with a progressive decrease as the cell matured in vitro (48 hours, 72 hours, and 7 days). Cultured astrocytes also produced K6, albeit at a lower level than oligodendrocytes, but showed a similar progressive loss of expression as the cells matured. A second band also was observed that cross-reacted with the K6 antisera, with a molecular weight of approximately 42 kDa. This band may represent K6 bound covalently to an endogenous regulator (e.g., an inhibitor).

Figure 9:
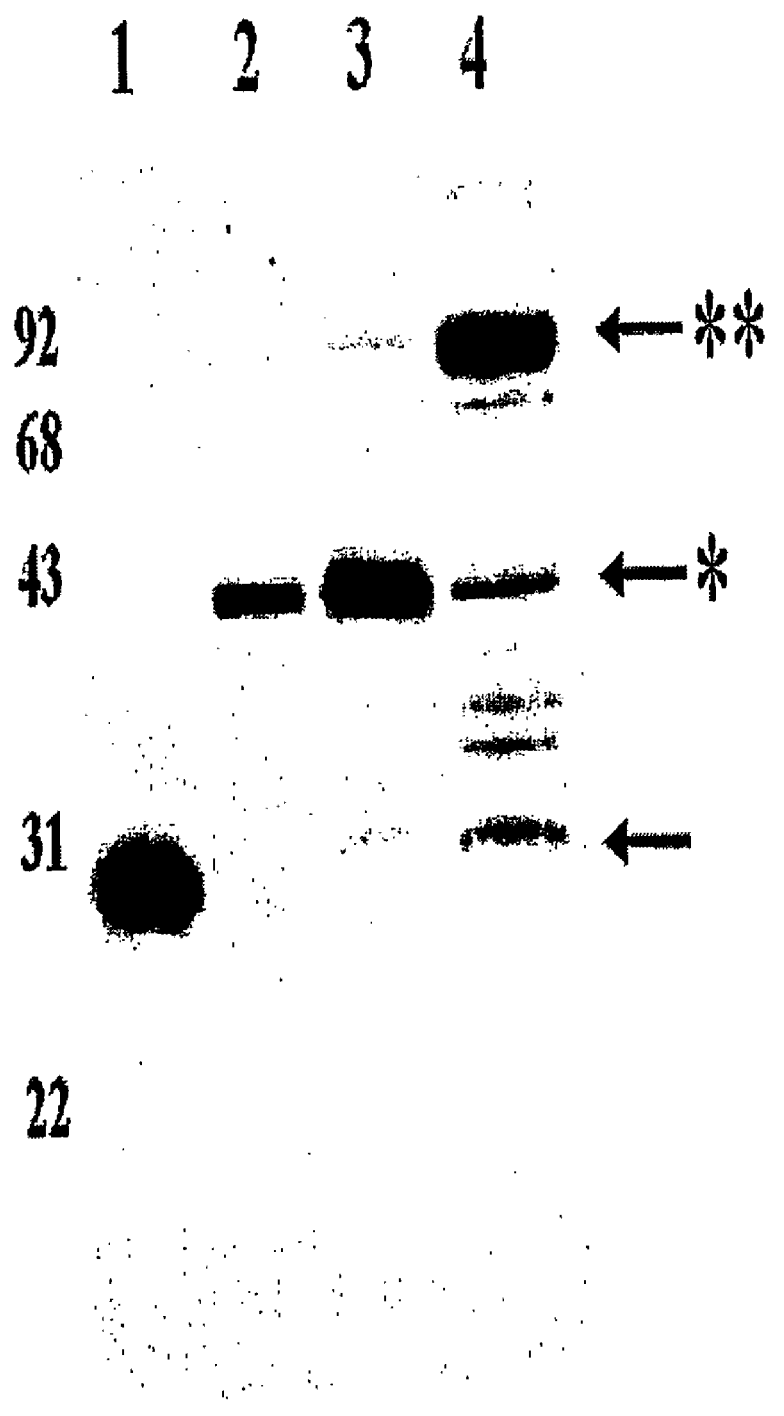

The putative endogenous inhibitor of K6 appeared to be unique to CNS tissues. Western blotting of rat tissue homogenates with rabbit polyclonal antibodies against r-K6 revealed the presence of both mature K6 and higher molecular weight complexes (FIG. 9). The higher molecular weight complexes, with masses of approximately 42 and 91 kDa, may represent the formation of K6/inhibitor complexes. The larger 91 kDa complex was observed primarily in the kidney (lane 4), whereas the 42 kDa complex was found predominantly in the brain and spinal cord (lanes 2 and 3, respectively). A complex of 42 kDa also has been identified in purified populations of nervous system cells (FIG. 8). These data support the presence of unique endogenous K6-inhibitors in neural compared with non neural tissues.

Example 11

Excess K6 Results in a Dying Back of Oligodendrocyte Processes

Figure 16:
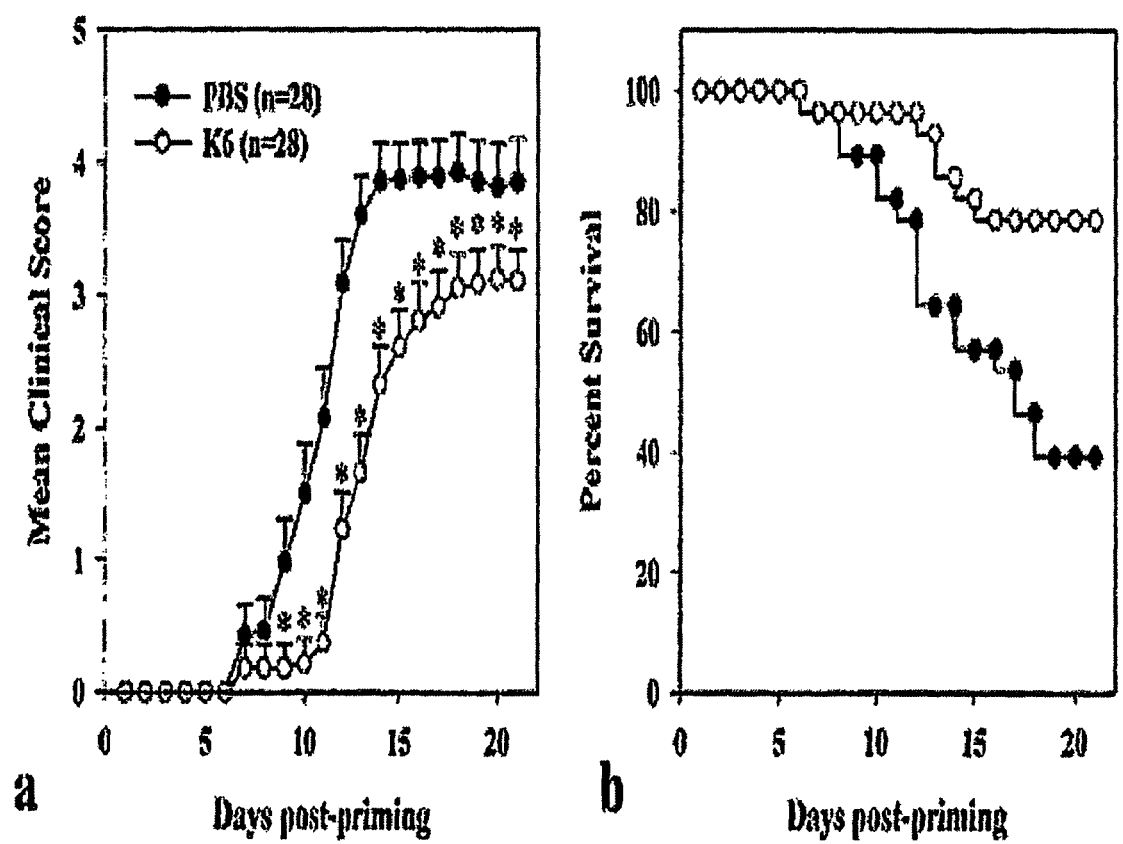
FIGS. 16A and 16B are graphs indicating that K6-immunization at the time of EAE induction delays the onset and attenuates the severity of PLP139-151 EAE. Mice were immunized with PBS or K6 at the time of priming with 100 µg of PLP139-151 in CFA. (A) Data represent mean clinical score of each group plotted against time. The clinical scores of mice immunized with K6 were significantly below those of control PBS immunized mice from D9 throughout the remainder of the disease course examined; * $P<0.05$, Mann-Whitney U test. (B) K6-immunization at the time of priming was also associated with a significant increase in survival (10/28 compared to 22/28, $P=0.003$ $\chi2$ using Fisher's exact test).

While regulated expression of K6 appears to be important to normal oligodendrocyte development, it is hypothesized that an excess of K6, as is present at sites of CNS inflammation, may contribute to oligodendrogliopathy. To address the potential effect of K6 on the stability of oligodendrocyte processes, oligodendrocyte progenitors were plated and allowed to differentiate for 72 hours. At this point the wells contained a mixture of O4$^+$ and O1$^+$ cells. Active r-K6 was added to triplicate wells at a concentration of 1 or 10 µg/ml, and cells were incubated for an additional 72 hours before staining for sulfatide with an O4 monoclonal antibody. Exposure of mature oligodendrocytes to r-K6 resulted in a 2- to 3-fold decrease in the number of O4$^+$ processes (FIG. 16A), but had no effect on the number of O4$^+$ cells (FIG. 16B), or the total number of cells (FIG. 16C). Excess K6 thus had a dramatic effect on the stability of oligodendrocyte processes, but did not affect cell survival or differentiation toward the O4$^+$ lineage ($P<0.05$).

Over-expression of K6 in oligodendrocyte progenitors also decreased process outgrowth. The full-length K6 clone was inserted into a vector encoding green fluorescent protein (GFP) to allow production of a K6-GFP fusion protein. CG4 oligodendrocyte progenitors were transfected with either the K6-GFP construct or the vector encoding GFP alone, and the number of processes in cells expressing GFP was determined at 12, 48, or 96 hours post-transfection. While neither construct affected oligodendrocyte survival, cells that over-expressed K6 had significantly fewer processes from the 48 hour time point onwards, relative to the GFP control ($P<0.05$). Over-expression of K6 within the cell therefore had the same effect as applying K6 exogenously.

Example 12

Inhibition of K6 Attenuates CNS Demyelinating Disease

K6-Immunization and TMEV Infection: Eight-week old female SJL/J mice (Jackson Laboratories) were each immunized with 100 µg of recombinant K6 (r-K6) in 200 µl of complete Freund's Adjuvant (CFA, Difco) containing 200 µg of heat-killed mycobacterium. K6 was expressed in the baculovirus system, purified and activated as described in the Methods and Materials Section. Control animals were immunized similarly, receiving the non-self antigen ovalbumin (OVA, Sigma), CFA alone, or PBS only. Emulsion was injected subcutaneously in each flank, and at the base of the tail.

K6 and OVA antibody titers were determined by ELISA, and animals boosted with an intraperitoneal (or subcutaneous) injection of 25 µg of r-K6, or OVA in PBS, or with PBS alone. One week after the boost, animals were injected intracerebrally with 2×10$^6$ plaque-forming units (PFU) of the Daniel's strain of TMEV, in a 10 µl volume. Forty days post-TMEV infection, sections through the spinal cord of each animal were evaluated histologically, and K6 or OVA antibody titers determined from sera. Mice were anesthetized with an overdose of sodium pentobarbital (150 mg/kg), and following sera collection, perfused transcardially with 4% formaldehyde, 1% glutaraldehyde in PBS (pH 7.4), or 4% paraformaldehyde. Spinal cords were sectioned transversely into 1 mm blocks, and every third block embedded in glycol methacrylate. For assessment of demyelination, 1 µm thin sections were cut from the plastic embedded blocks, and stained with a modified erichrome stain, with a cresyl violet counterstain. This methodology reproducibly allows the visualization of inflammatory cells and the extent of demyelination within the spinal cord.

TMEV DTH: TMEV-specific delayed-type hypersensitivity responses (DTH, a measure of Th1 immune responses) were determined 48 hr prior to the end of each experiment. Ultraviolet-irradiated purified TMEV (2.5 µg) or PLP139-151 peptide (10 µg) in a 10 µl volume were injected intradermally into opposite ears, using a 500 µl Hamilton syringe (Hamilton Co., Reno, Nev.) fitted with a 30-gauge needle. Ear swelling was measured at 24 and 48 hr after injection, with a dial gauge micrometer. The mean difference compared with the pre-injection measurements in each group was compared between K6-immunized mice and control groups.

Quantitative Histology: Quantitative morphologic analysis was performed on 10-15 sections, corresponding to 10-15 different spinal cord segments, per mouse. Two methods were used to determine the extent of white matter pathology. First, the total white matter area and the total lesion area (in mm$^2$) were calculated using a Zeiss interactive digital analysis system (ZIDAS), and camera lucida attached to a Zeiss photomicroscope. Data were expressed as the percent of total lesion area per total white matter area. Second, a pathologic score reflecting the frequency of pathology was assigned to each animal based on meningeal inflammation and demyelination. The score is expressed as a percentage of the total number of spinal cord quadrants positive for each pathologic measurement, divided by the total number of spinal cord quadrants examined. A maximum score of 100 reflects the presence of pathology in all 4 quadrants of every spinal cord segment examined from an individual spinal cord. The significance of differences in the percent of quadrants with each pathological feature, or in percent lesional area, was determined by One Way Analysis of Variance (ANOVA) and the Student-Newman-Kuel's (SNK) post-hoc test.

Figure 11:
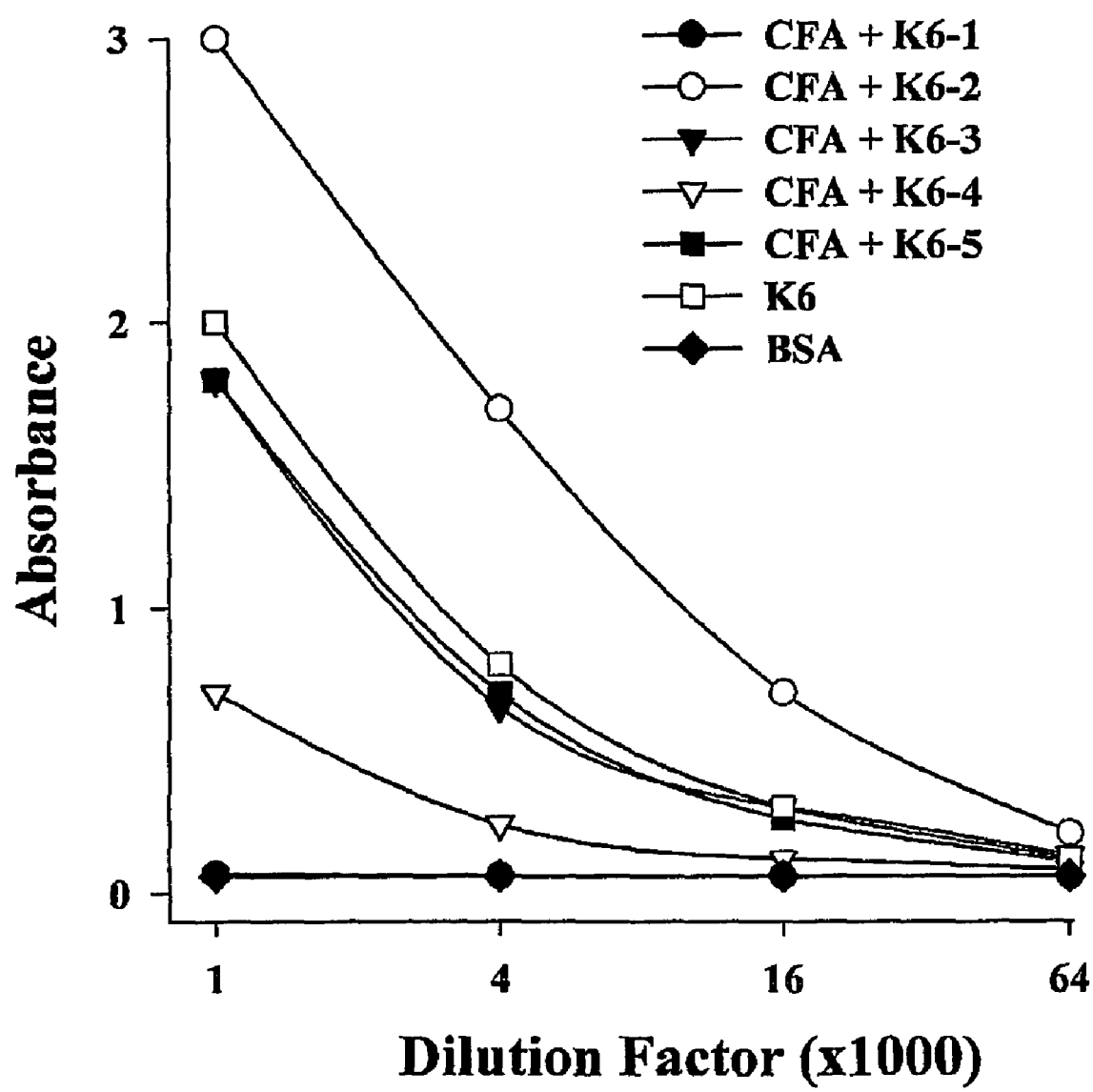
FIG. 11 is a graph depicting the K6 antibody response.

The immunization strategy revealed that both inflammation and demyelination were decreased in the TMEV model of MS. High K6 antibody titers were observed in the sera of mice 4 weeks after immunization with r-K6 (FIG. 11). The sera of animals immunized with CFA alone did not have significant K6 antibody titers. Similar results were observed in all immunized mice. Bovine serum albumin (BSA) was substituted for sera as a negative control in this assay.

Figure 12:
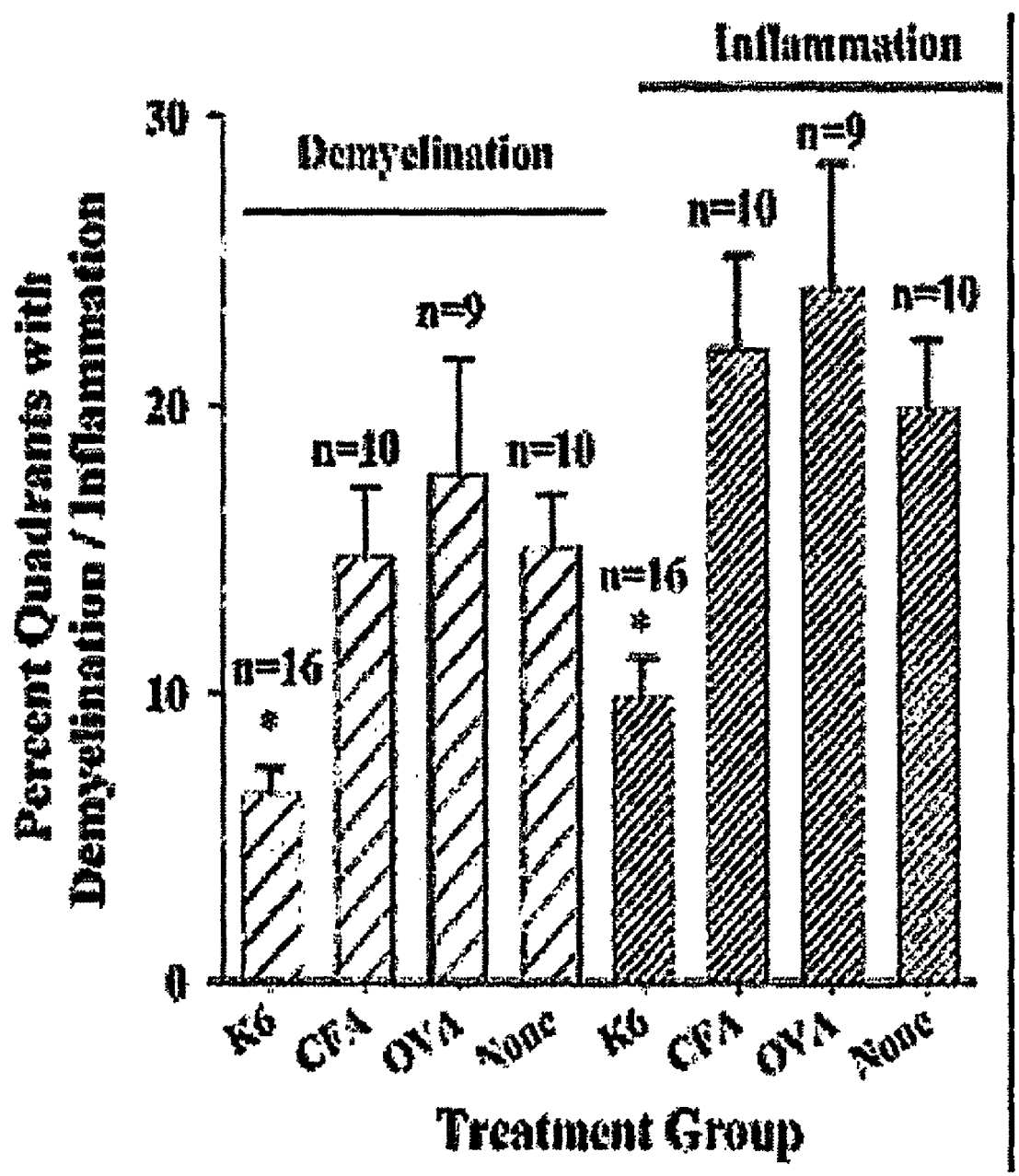
FIG. 12 is a graph depicting high K6-antibody titers, decreased spinal cord demyelination and inflammation in the TMEV model of MS. Quantification of the percent spinal cord quadrants with demyelination, or inflammation in animals 40 days post-TMEV infection, which had been previously immunized with K6 or OVA in CFA, with CFA alone, or without any prior immunization (none). Immunization of mice with K6 (5 weeks prior to TMEV infection), significantly decreased the number of spinal cord quadrants associated with demyelination or inflammation, relative to all immunization control groups (ANOVA, $P<0.002$, *SNK, $P<0.05$).
Figure 13:
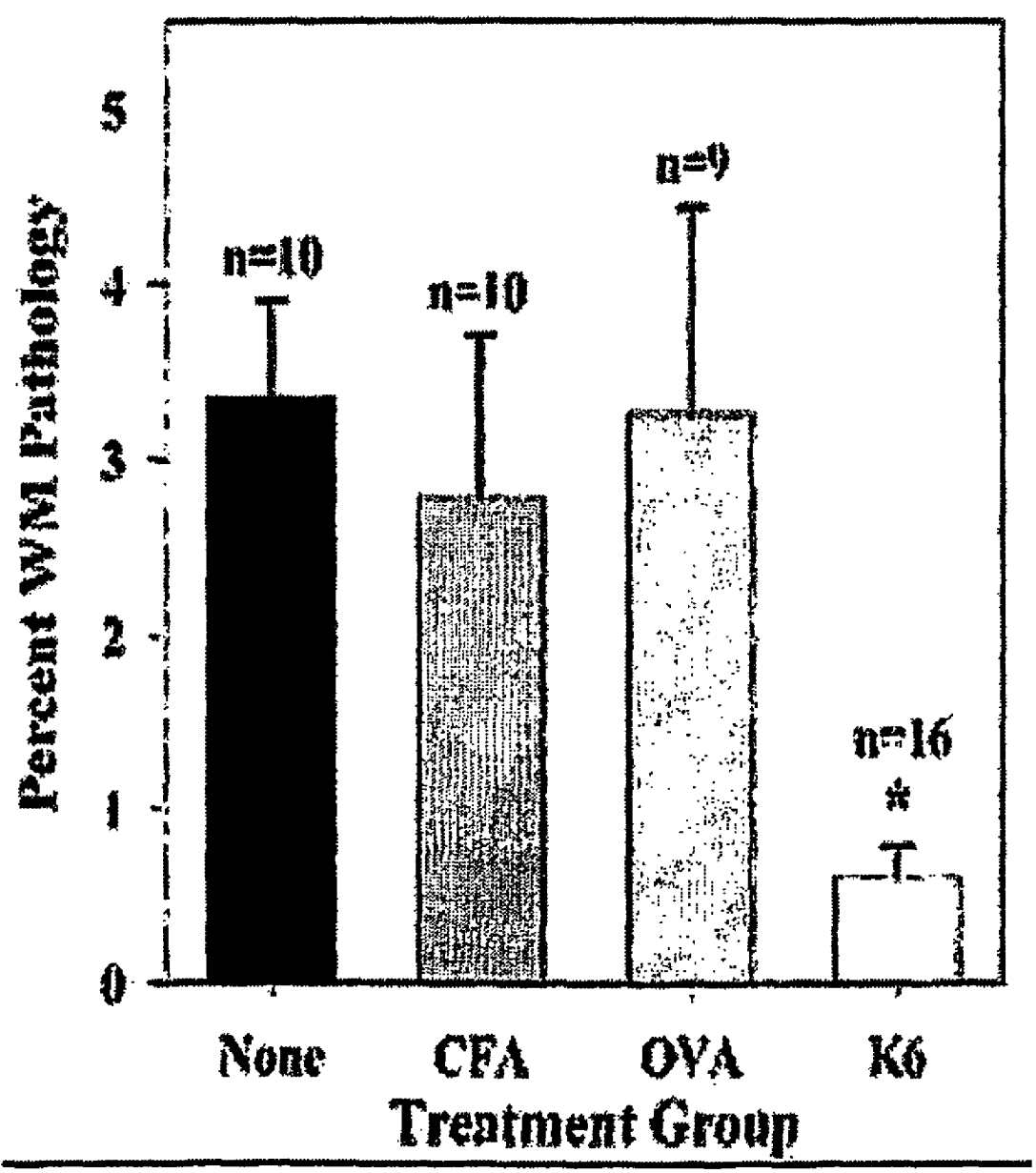
FIG. 13 is a graph indicating that K6-immunization results in significantly less white matter pathology following TMEV infection. Quantification of the area of white matter pathology along the length of the spinal cord 40 days post-TMEV infection in K6-immunized mice relative to control mice immunized with OVA, CFA alone, or without any prior immunization (none). K6-immunization was associated with a greater than 3-fold reduction in the percent of the spinal cord white matter associated with pathology (ANOVA, $P<0.002$, *SNK, $P<0.05$).

The percentage of spinal cord quadrants showing demyelination (DM) or inflammation (Infl) was quantified for animals immunized (I) with K6 or CFA alone. Immunization of mice with r-K6 (n=9) 5 weeks prior to TMEV infection resulted in significantly less DM and Infl in the spinal cord when examined at 40 days post-infection, as compared to mice immunized with CFA alone (n=10) ($P<0.05$, FIG. 12). K6-immunization was associated with a greater than 3-fold reduction in the percent of the spinal cord white matter associated with pathology (ANOVA, $P \leq 0.0023$, *SNK, $P<0.05$). These results were confirmed in two independent experiments.

In CFA-immunized mice, well-formed demyelinated lesions with extensive perivascular and parenchymal cell infiltrates formed in response to TMEV infection, but such lesions were significantly less prominent in K6-immunized mice. The amount of demyelination and inflammation was determined in 10 to 15 sections per mouse, by assessing the number of spinal cord quadrants containing each pathological feature. Spinal cords were embedded in glycol methacrylate plastic and stained with a modified erichrome/cresyl violet stain.

Figure 14:
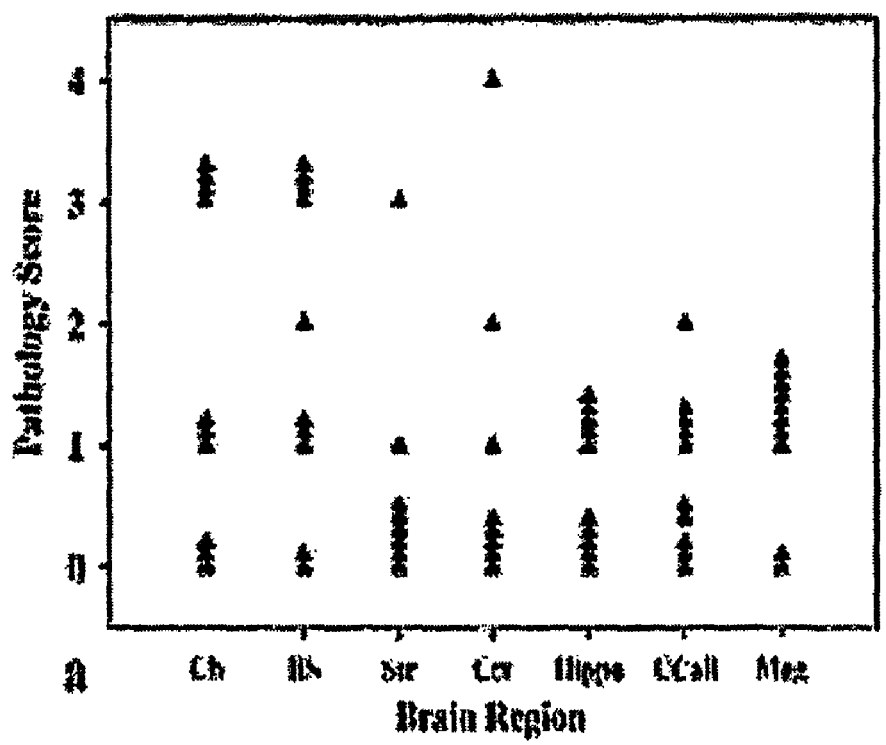
FIGS. 14A and B are histograms quantitating the brain pathology in control animals immunized with CFA alone (A) or with K6 (B). Each symbol represents an individual mouse graded on a scale of 0 to 4. Cb, cerebellum; BS, brain stem; Str, striatum; Ctx, cortex; Hippo, hippocampus; CCall, corpus callosum; Mng, Meningeal Inflammation.
Figure 14:
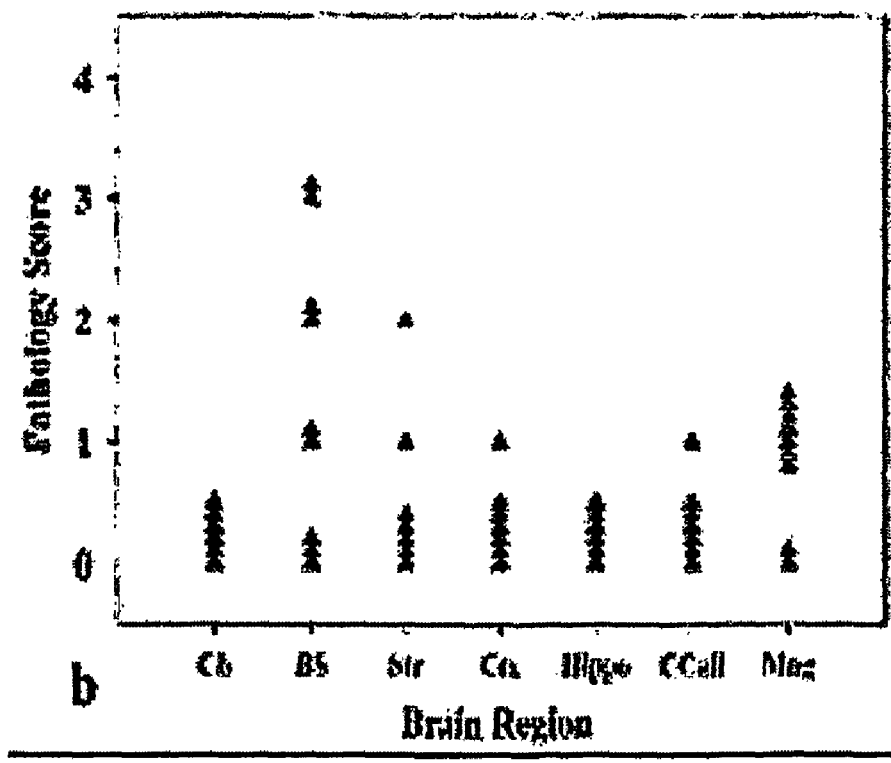

Levels of brain pathology were quantified for control animals immunized with CFA alone (FIG. 14A) and for animals immunized with K6 (FIG. 14B). A score of 0 reflected the absence of pathology; a 1, no tissue destruction and minimal inflammation; a 2, early tissue destruction (loss of architecture) and moderate inflammation; a 3, definite tissue destruction (demyelination, parencymal damage); and a 4 frank parenchymal necrosis. K6 immunized mice had significantly less disease in all brain regions examined, which included the cerebellum, brain stem, striatum, cortex, hippocampus, corpus callosum, and meningea).

Figure 15:
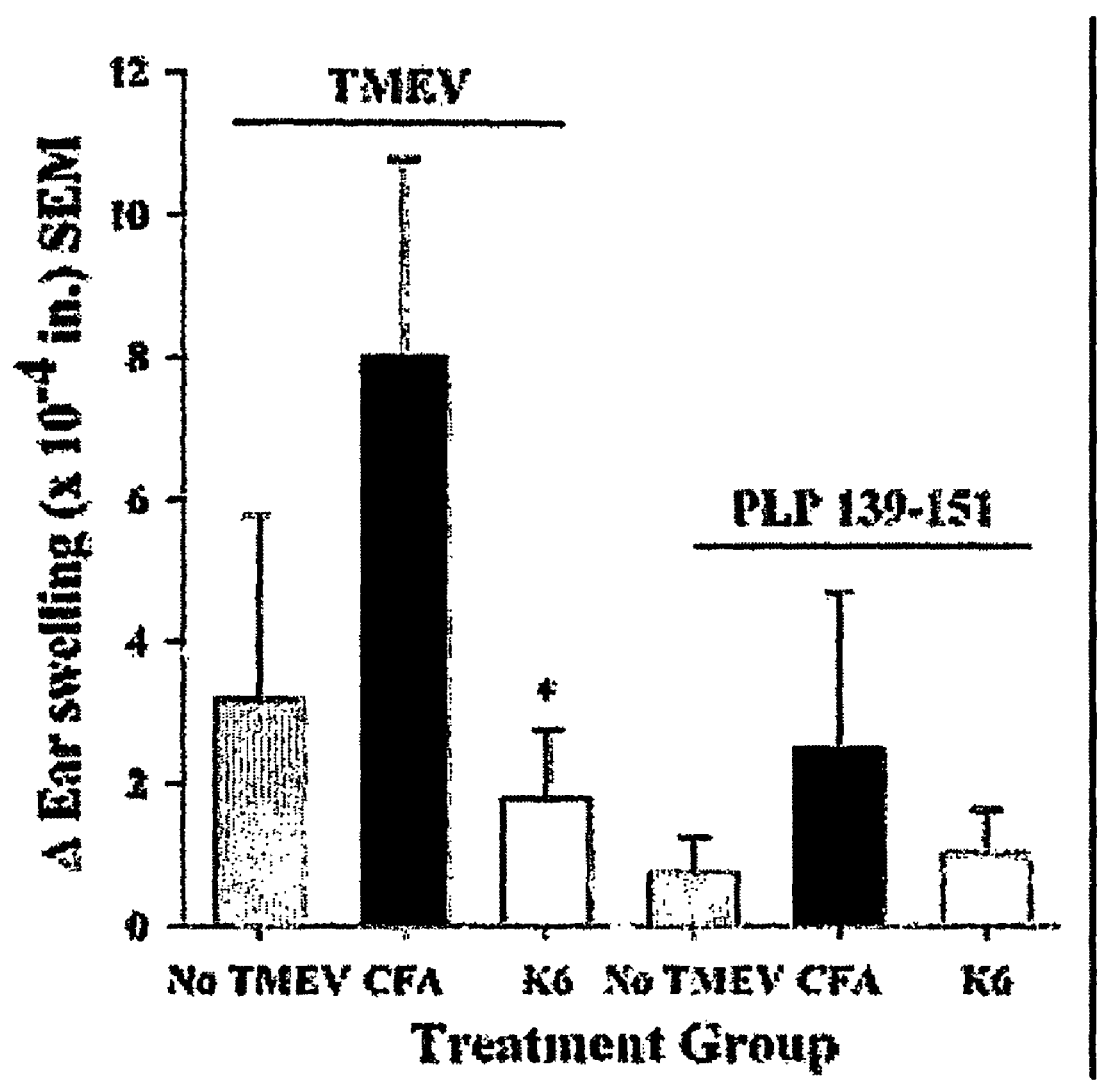
FIG. 15 is a graph depicting DTH responses to the disease-inducing TMEV. Data shown represent the mean 48 hr change in ear thickness±SEM, in response to challenge with 2.5 µg of UV-irradiated, purified TMEV. DTH responses were significantly reduced in the K6-immunized mice at the 48 hr time point (*$P<0.05$, unpaired Students t-test), compared to mice immunized with CFA-containing PBS alone.

High K6-antibody titers attenuated viral-induced Th-1 response in vivo. DTH responses to the disease-inducing TMEV were evaluated in mice at day 38 after infection (n=8 per group). Data shown in FIG. 15 represent the mean 48 hr change in ear thickness±SEM, in response to challenge with 2.5 μg of UV-irradiated, purified TMEV. DTH responses were significantly reduced in the K6-immunized mice at the 48 hr time point (*P<0.05, unpaired Students t-test) compared to mice immunized with CFA-containing PBS alone. No significant DTH responses were observed in response to TMEV in mice that were uninfected. No significant DTH responses were observed in these mice in response to the self-peptide PLP-139-151 at 38 days post-TMEV infection.

Example 13

The Presence of High K6 Antibody Titers, Generated Using an Active Immunization Approach, Decreased Both Spinal Cord Demyelination and Inflammation, as Well In Vivo and In Vitro Th1 Immune Responses, in an Autoimmune Model of Multiple Sclerosis Generation of K6 antibody titers and EAE Induction: Function blocking K6-antibodies were generated by active immunization of mice with recombinant K6 (K6), resulting in the generation of K6-specific antibodies in a self-autonomous fashion. Mice were immunized for K6 antibody generation either at the time of EAE induction, using Complete Freund's Adjuvant, or prior to or EAE induction, using Ribi Adjuvant (Corixa) to avoid repeated CFA administration.

EAE was induced in 12-week old female SJL (H-2$^S$) mice (Jackson Laboratories, Bar Harbor, Mass.) by immunization with 100 μg of the highly encephalitogenic peptide PLP139-151 (HSLGKWLGHPDKF), dissolved in PBS and emulsified with Incomplete Freund's adjuvant (IFA), containing 400 μg of *Mycobacterium Tuberculosis*, strain H37Ra (Difco, Detroit Mich.). In this first series of experiments, mice were immunized with K6 at the time of EAE induction, by adding 75 μg per mouse of K6 in PBS, or PBS alone, at the time of emulsification. Groups of 14 mice were injected subcutaneously (s.c.) with 0.2 ml of the peptide emulsions, and on the same day, and 48 hr later, injected intraperitoneally (i.p.) with 400 ng of *Bordetella Pertussis* toxin in 0.1 ml of PBS. This high dose PLP139-151 priming protocol produced severe disease with substantial mortality before the 21-day endpoint, precluding meaningful analysis of pathology. In a second series of experiments therefore, in which the effects of MSP-pre-immunization were examined, a milder form of EAE was chosen in which consistent clinical disease was induced, but in which mortality was reduced. High levels of K6 antibody titers were established in these mice prior to the induction of EAE, by immunizing mice with 70 μg of K6 in 100 μl of PBS, mixed with 100 μl of Ribi adjuvant, resuspended in PBS, or Ribi-PBS alone. As a second negative control, other groups of mice received no immunization prior to the induction of EAE. Two-hundred μl of the Ribi-K6 suspension or Ribi alone, were injected s.c. at two sites on the flanks of mice following the manufacturers instructions. Sera obtained by tail bleed were examined by ELISA to confirm the production of K6 antibodies prior to EAE induction. The lower dose PLP139-151 priming was induced in these mice by administering 50 μg of PLP 139-151, in IFA containing 200 μg of *M. Tuberculosis*, supplemented with 20 μg of K6. Mice were given 100 ng of *B. Pertussis* toxin on the day of immunization and 48 hr later. All peptides were synthesized by the protein core facility at the Mayo Clinic, with amino acid composition verified by mass spectrometry, and purity (>98%) confirmed by mass spectroscopy.

Assessment of Clinical Disease: Mice were housed under barrier conditions, and paralyzed mice were afforded easier access to food and water. The primary end point in these experiments was clinical outcome and animals were observed daily and graded in a blinded fashion according to their clinical severity as follows: grade 0, no clinical disease; grade 1, loss of tail tonis; grade 1.5, impairment of righting reflex; grade 2, paresis or paralysis of one hind limb; grade 3, complete paralysis of both lower extremities; grade 4, non-ambulatory and moribund; grade 5, death. Sera were collected at the time of sacrifice to examine K6 and PLP antibody titers.

Statistical Analysis: Where data were non-linear, as in the case of behavior scores, the significance of differences between K6-immunized mice and controls, was determined by non-parametric Mann-Whitney U-test. Parametric unpaired Student's t-test was used for evaluation of differences in histological scores, DTH, T-cell proliferation, cytokine production and serum antibody responses, except when data was not normally distributed in which case the Mann-Whitney U-test was used. Comparison of percent survival between groups was made using $X^2$ employing Fisher's exact test. Statistical significance was set at $P \leq 0.05$.

Results: K6-immunization at the time of, or prior to PLP-139-151 priming, inhibits the development of clinical signs of EAE. The role of K6 in the development of clinical and histological manifestations of EAE was investigated by inhibiting K6 enzymatic activity using an active immunization approach. The presence of K6-antibodies generated prior to, or at the time of EAE induction, each delayed the onset of disease, and reduced clinical disease scores, in the PLP139-151 EAE model in SJL/J mice (FIGS. 16 to 19 and Tables 2 and 3).

K6 immunization at the time of PLP139-151 priming was shown to delay the mean day of disease onset (day 12.7±0.1 vs. control 10.1±0.4, P=0.006), in addition to the mean time to peak disease (day 14.7±0.5 vs. control 13.1±0.54, P<0.04) (FIG. 16A, Table 2).

TABLE 2

Clinical Disease in PLP-EAE in Mice Co-immunized with K6

| | Incidence | Survival | Day of Onset | MCS | Day of Peak Disease |
|---|---|---|---|---|---|
| EAE Control (n = 28) | 28/28 | 11/28 | 10.1 ± 0.4 | 2.9 ± 0.2 | 13.1 ± 0.5 |
| EAE with K6- Co-immunization (n = 28) | 28/28 | 22/28 | 12.7 ± 0.5 | 1.8 ± 0.2 | 14.7 ± 0.5 |
| | | P = 0.003$^a$ | P = 0.006$^b$ | P < 0.002$^c$ | P = 0.036$^b$ |

Clinical Scores in mice immunized with K6 at the time of PLP139-151-EAE induction. While the incidence of disease did not differ between the two groups, K6 immunization at the time of PLP139-151 priming was shown to delay the mean day of disease onset, in addition to the day of peak disease. The mean daily clinical score (MCS) was also significantly reduced in K6-immunized mice compared with the control group. Additionally, K6-immunization was associated with significantly improved survival to the 21 day end point compared with control mice ([a]$X^2$; [b]unpaired Student's t-test; [c]Mann-Whitney U test).

The mean daily clinical score after the onset of symptoms was also significantly reduced in K6-immunized mice (1.8±0.3) compared with the control group (2.8±0.4, P<0.01), as was the mean maximal clinical disease observed (3.3±0.2 vs. control 4.3±0.2, P=0.003). Over the 21-day period examined, the K6 immunized mice also exhibited significantly more symptom free days (11.7±0.45 vs. control 9.1±0.38, P≦0.001). SJL mice with high dose PLP139-151-EAE used in these initial experiments, experienced severe clinical disease, with significant mortality. Notably, in this regard, K6-immunization was associated with significantly improved survival to the 21-day end point (22/28, 78.6%), compared with (10/28, 35.7%) in the control group (P=0.003, $X^2$ Analysis) (FIG. 16B, Table 2). The results of two independent experiments were similar and the data were combined for statistical analysis (n=28 per group). Given the high incidence of mortality in the high dose PLP experiments, histological examination of CNS tissue was not performed in detail.

Figure 17:
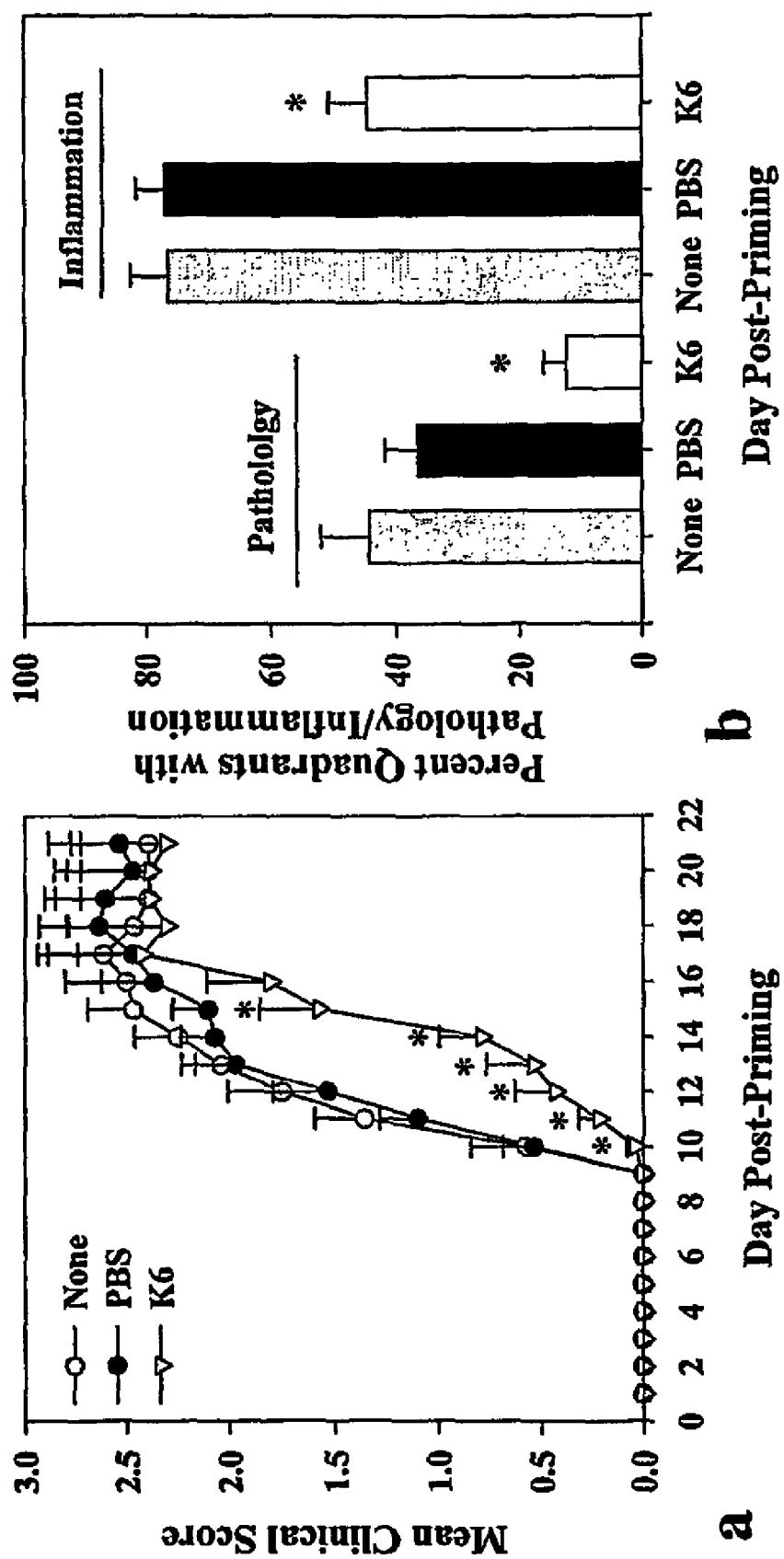
FIGS. 17A and 17B are graphs indicating that pre-immunization with K6 delays the onset and development of clinical and histological disease in PLP139-151 primed mice. (A) The mean day of onset and the time to peak disease were both delayed by 3 to 4 days in the K6 immunized mice, compared to non-immunized, and PBS-immunized controls ($P<0.02$). K6 immunized mice also exhibited significantly reduced mean daily clinical scores up to day 15 post-PLP priming (*$P<0.001$ Mann-Whitney U test). (B) Detailed histological evaluation of the spinal cord of mice in each group at the 21 day time point, indicated that K6-preimmunization reduced both of the extent of parenchymal pathology and meningeal inflammation, compared to each of the control groups examined (*Mann Whitney U, $P<0.05$).
Figure 18:
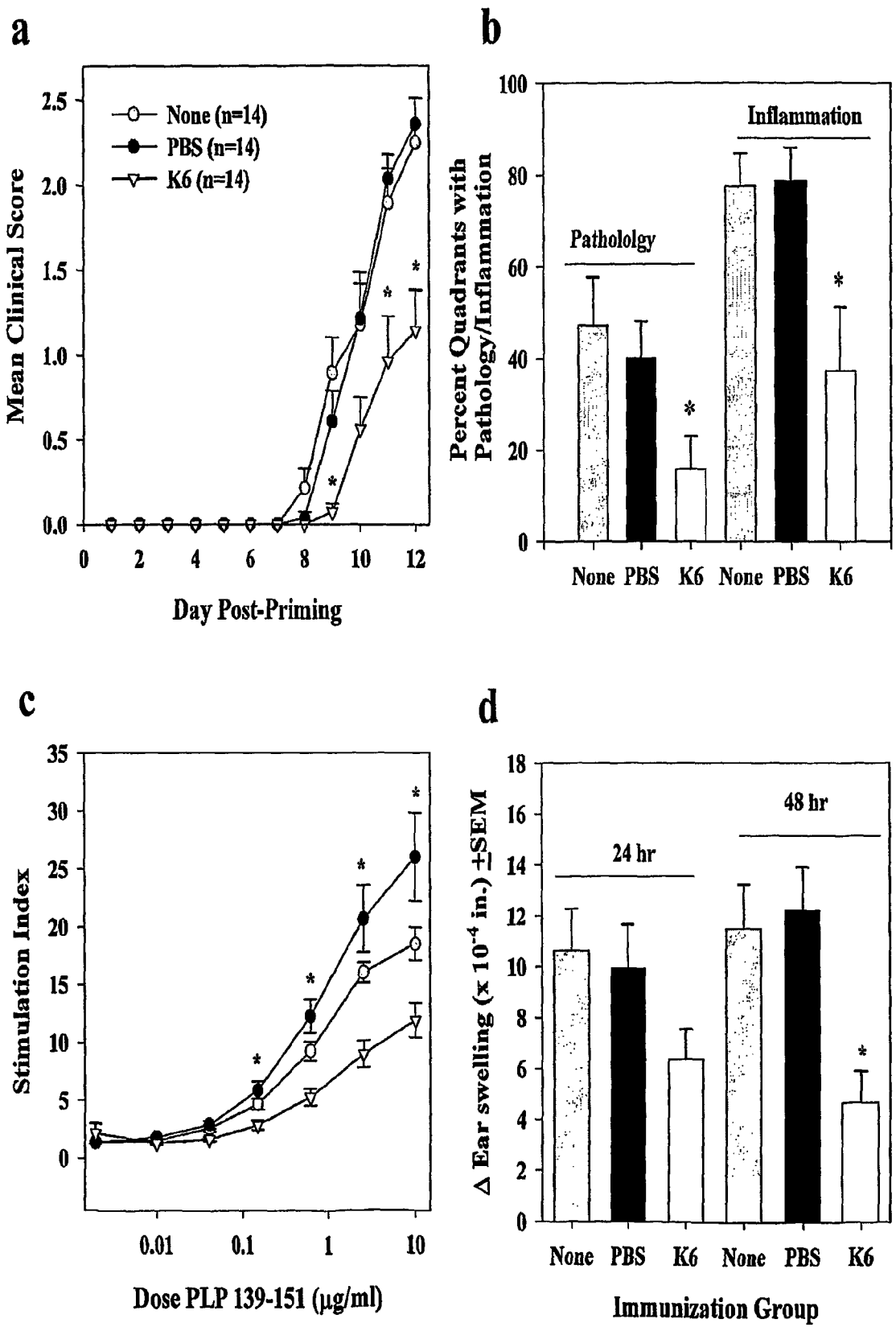
FIGS. 18A-D are graphs depicting that pre-immunization with K6 attenuates clinical disease, the development of CNS pathology, and the development of Th1 responses in vivo and in vitro when examined during the acute phase of the disease.

K6 pre-immunization, prior to the time of PLP139-151 priming, similarly attenuated the mean time to disease onset and the severity of clinical disease achieved (FIG. 17, Table 3). K6 pre-immunization delayed the mean onset of clinical disease by approximately 4 days relative to control mice (day 14.3±0.8, n=13 vs. PBS-immunized 10.5±0.1, n=15 vs. no prior immunization 10.8±0.2 P<0.001, n=14), as well as the mean time to peak disease (day 16.9±0.6 vs. PBS-immunized 14.7±0.7 vs. no prior immunization 13.7±0.6 P<0.02). K6-pre-immunization was also associated with a significant reduction in the mean daily clinical score after the onset of symptoms (1.4±0.3 vs. PBS-immunized 2.1±0.2 vs. no prior immunization 2.1±0.2 P<0.001). As was the case for K6 immunization at the time of EAE induction, K6-pre-immunized mice exhibited significantly more disease free days over the period examined (13±0.8 vs. PBS-immunized 9.5±0.2 vs. no prior immunization 9.6±0.1 P≦0.001). No significant differences in the timing or severity of clinical disease were observed between non-immunized and PBS immunized mice. The incidence of disease and survival in the lower dose PLP-EAE did not differ significantly between the groups examined. Notably, despite the lower dose PLP used in the pre-immunization experiment, and the establishment of high K6 antibody titers prior to priming, the overall ability of the two treatment paradigms to delay the onset of disease and to attenuate its severity, was similar. Collectively, these results indicate that K6-immunization is effective in delaying and attenuating clinical signs of PLP139-151-induced EAE and suggest that other methods of inhibiting K6 activity would similarly attenuate disease.

TABLE 3

Clinical Disease in PLP-EAE in Mice Pre-immunized with K6

|  | Incidence | Survival | Day of Onset | MCS | Day of Peak Disease |
|---|---|---|---|---|---|
| EAE Control (n = 14) | 14/14 | 12/14 | 10.8 ± 0.2 | 2.1 ± 0.2 | 13.7 ± 0.2 |
| EAE Ribi-PBS-Pre-immunization (n = 15) | 15/15 | 13/15 | 10.5 ± 0.1 | 2.1 ± 0.2 | 14.7 ± 0.2 |
| EAE with Ribi-K6-Pre-immunization (n = 15) | 12/13 | 11/13 | 14.3 ± 0.8 | 1.2 ± 0.2 | 16.9 ± 0.2 |
|  |  |  | P < 0.001[a] | P <0.005[a] | P <0.001[a] |

Clinical Scores associated with pre-immunization of mice with K6 prior to PLP139-151-EAE induction. K6-pre-immunization prior to PLP-139-151 priming reduced the mean clinical score and the day of disease onset relative to control mice receiving no prior immunization or pre-immunized with PBS alone ([a]*Mann Whitney U, P<0.05).

Example 14

K6-Immunization Reduces Clinical and Histological Disease, in Addition to Th1 Immune Responses in Acute PLP139-151 Induced EAE To further understand the mechanisms by which anti-K6 antibodies ameliorate PLP139-151-induced disease, the effects of K6-immunization on T cell function were examined using in vivo and in vitro approaches, during the acute phase of the disease. The following approaches were used.

T Cell Proliferation: Spleens were removed at 12 days post-EAE priming, and proliferation assays were carried out in flat-bottomed 96-well microculture plates (Falcon Labware, Oxnared, Calif.), in a total volume of 200 µl complete Click's medium, using 5×10$^5$ spleen cells. Antigen-specific proliferation was assessed in triplicate by the incorporation of [$^{3}H$]TdR (1 µCi/well) during the final 18 hrs of a 96 hr culture period, using a PLP139-151 peptide dilutions starting at 10 µg/ml. Parallel concentrations of a non-specific antigen, OVA 323-339 peptide (ISQAVHAAHAEINEAGR, SEQ ID NO:3) were used as negative controls. As a positive control, Concanavalin A (Sigma) was used at dilutions starting at 10 µg/ml. [$^{3}H$]TdR uptake was detected using a Topcount microplate scintillation counter (Packard Instrument, Meriden, Conn.). Results were expressed as stimulation index=mean cpm of Ag containing cultures/mean cpm of control cultures without added antigen.

DTH: DTH responses were quantified using a 24 to 48 hr ear-swelling assay, at 9 days post-PLP139-151 priming. Pre-challenge ear thickness was determined using a dial gauge micrometer. DTH responses were elicited by injecting 10 µg of the priming peptide PLP139-151 in 10 µl saline, into the ventral surface of the right ear and OVA 323-339 peptide at the same concentration into the left ear, as outlined in the TMEV section. At 24 and 48 hrs after ear challenge, the increase in ear thickness over pre-challenge measurements was determined. Results were expressed in units of 10$^{-4}$ inches+SEM. Ear swelling responses were the result of mononuclear cell infiltration and showed typical DTH kinetics (i.e. minimal swelling at 4 hr, maximal swelling at 24-48 hr).

Th1 Cytokine Production: For cytokine analysis, $2.5 \times 10^6$ spleen cells were cultured in a total volume of 1 ml complete Click's media, supplemented with 10 µg/ml of PLP139-151, or with Click's media alone. Supernatants were harvested at 72 hr and analyzed for IFN-γ and IL-2 production by capture ELISA, using capture and detection antibodies, in addition to cytokine standards, from Pharmingen following the manufacturer's recommendations.

Results: To examine the potential effects of K6-immunization on Th1 expansion and/or differentiation, the level of PLP139-151-specific T-cell proliferation and cytokine production were assessed in treated mice. Recall responses of splenocytes isolated from PLP139-151-primed mice were measured by in vitro proliferation assay at the end of each experiment, that is, on day 12 post-priming, upon restimulation in vitro. Splenocytes from all PLP139-151 primed mice (FIG. 18A), proliferated in response to PLP139-151 peptide in a dose dependent fashion. The proliferative response to PLP139-151, but not the irrelevant antigen, OVA peptide, was significantly decreased in splenocytes isolated from mice immunized with K6 (n=14), compared with PBS immunized mice (n=14), or mice receiving no prior immunization (n=14), when examined on day 12 after PLP139-151-priming (FIG. 18C). More than 10-fold more PLP-peptide was required to produce equivalent proliferation by splenocytes isolated from K6-immunized mice, compared to each of the control groups (P≦0.005). These results suggest that anti-K6 antibodies alter the responsiveness of myelin specific T cells to disease producing antigen.

PLP-139-151-specific DTH responses in K6-immunized mice: In vivo, PLP139-151-induced ear swelling (DTH), was suppressed in K6-immunized mice when initiated on Day 9 post-PLP priming, in the mice described in FIG. 18A. The development of DTH to the priming epitope was reduced by approximately 2.6-fold in K6-immunized, relative to their non-immunized, or adjuvant control immunized littermates, at the 48 hr time point (P≦0.003), (FIG. 18D). A significant DTH response was not observed following the injection of OVA peptide in any of the groups, indicating the specificity of the assay. This suggests that anti-K6 antibodies act, at least in part, by inhibiting the effector function of myelin-specific Th1 responses.

K6-immunization blocks the differentiation of PLP139-151-specific Th1 cells: To determine the effects of anti-K6 treatment on Th1 differentiation, we assessed the ability of PLP-responsive T cells to produce Th1 cytokines, IFN-γ and IL-2. Secondary in vitro stimulation of PLP139-151-specific T cells, derived from the spleens of mice pre-immunized with K6, or PBS, or from those receiving no prior immunization, revealed that production of the Th1 cytokine IFN-γ0 was suppressed by approximately 3-fold in the K6 pre-immunized mice (P<0.05 unpaired Student's t-test) relative to control groups (FIG. 19, n=6 per group). The levels of IFN-γ production by unstimulated cells, was not significantly affected, suggesting recovery of similar numbers of activated Th1 cells, and arguing against global immuno-suppression by K6 immunization. Moreover, despite reduced levels of IFN-γ, IL-2 secretion was comparable between the different groups. PLP139-151-induced secretion of IL-4, IL5 and IL10 were also assessed, but only minimal levels of secretion of these cytokines were observed in all cultures and this likely reflects the fact that SJL mice are poor Th2 responders. These results are consistent with the ability of anti-K6 antibodies to inhibit Th1 differentiation.

K6-pre-immunization reduces the development of histological EAE: Detailed histological examination of inflammation and pathological changes in the spinal cord were made in the K6 pre-immunized, and control groups of mice, to determine whether reduced clinical disease scores seen with K6-immunization, correlated with reduced CNS inflammation and/or pathology. Quantitative evaluation of spinal cord sections showed that reduced clinical deficits were associated with reduced meningeal inflammation and pathology when examined either at day 12 (FIG. 18B), or at day 21 (FIG. 17B), following PLP-139-151 priming. A comparison of the percent of spinal cord quadrants with meningeal inflammation, or frank parenchymal pathology, is shown in FIGS. 17B and 18B. The mean percent of spinal cord quadrants with meningeal inflammation/white matter pathology, at 12 days post-EAE induction, was significantly reduced in the K6-immunized mice (37.3%±13.9/15.9%±7.1, n=6), compared to those mice immunized with PBS alone (78.8%±7.3%/40.1±19.9, n=6), and to those receiving no prior immunization (77.6%±17.5/47.5%±10.4, n=6) (unpaired Student's t-test, P≦0.05). A similar reduction in the percent of spinal cord quadrants with meningeal inflammation/pathology was also apparent between K6-pre-immunized mice on day 21 post-EAE induction (44.6%±6.3/12.5%±3.7, n=11), compared to those mice immunized with PBS alone (77.1%±4.4/36.6%±5.2, n=13), and to those receiving no prior immunization (76.5%±6.2/47.5%±10.4) (unpaired Student's t-test, P≦0.007, n=12). This was the case, even though clinical deficits were not statistically different between the different groups of mice at the 21-day time point. No significant differences were observed between mice pre-immunized with PBS, compared to those receiving no immunization, prior to the induction of EAE, at any of the time points examined.

Example 15

Immunoglobulin from K6-Immunized Mice Blocks the Enzymatic Activity of K6 In Vitro To determine the efficacy of K6-antibodies generated by direct K6-immunization of mice to block K6 activity, immunoglobulins were isolated from pooled sera of mice immunized with K6 in CFA or with CFA containing PBS alone, collected prior to EAE induction, by protein G purification (Pharmacia). Immunoglobulin isolated from K6-immunized mice was also compared to commercially available normal mouse IgG (ChromPure mouse IgG, whole molecule, Jackson ImmunoResearch), as an alternative negative control. Additionally, monoclonal antibodies raised against whole recombinant K6 were generated, and their ability to block K6 activity in vitro was examined. The following methods were used.

MBP Hydrolysis: The function blocking capacity of K6-antibodies was examined in vitro by determining their ability to inhibit cleavage of rat myelin basic protein (MBP), isolated from whole rat spinal cord, as well as an Arginine-specific fluorogenic substrate, Ac-Ala-Thr-Arg-pNa (Bachem, King of Prussia, Pa.). For analysis of MBP digestion, 10 ng of active-K6 was mixed with 2 µg of IgG isolated from mice immunized with K6 or PBS alone, in 50 mM Tris and 100 mM NaCl buffer (pH 8.0). The reaction mix was incubated for 15 min at RT. IgG negative controls were substituted with an equal volume of suspension buffer alone, in place of K6. MBP (5 µg) was then added to each reaction tube, or Tris buffer alone, as a control, and the reactions allowed to proceed for 3 hrs at 37° C. The reaction was stopped by adding SDS-PAGE sample buffer with β-mercaptoethanol and analyzed by 20% Tricine SDS-PAGE.

To examine the effect of IgG isolated from the sera of K6-immunized mice to block hydrolysis of the fluorogenic substrate AcATRpNA, 20 ng of active K6 was pre-incubated with 4 μg of IgG (1:35 molar ratio) at RT for 15 min, in 50 mM Tris., 1 mM EDTA, pH 8.5. The kinetic conditions of the assay were 1 nM of activated K6 with 400 μM AcATRpNA, incubated at 37° C. Absorbances were read at 405 nm at 15 min intervals over a period of 2 hr, with a final reading at the 3 hr time point, on a Beckman coulter DU640 spectrophotometer interfaced with temperature controller. A similar experimental design was used to test the ability of two K6-monoclonal antibodies (K6-2 and K6-3, $IgG_{1K}$) to block K6-mediated substrate hydrolysis.

Figure 20:
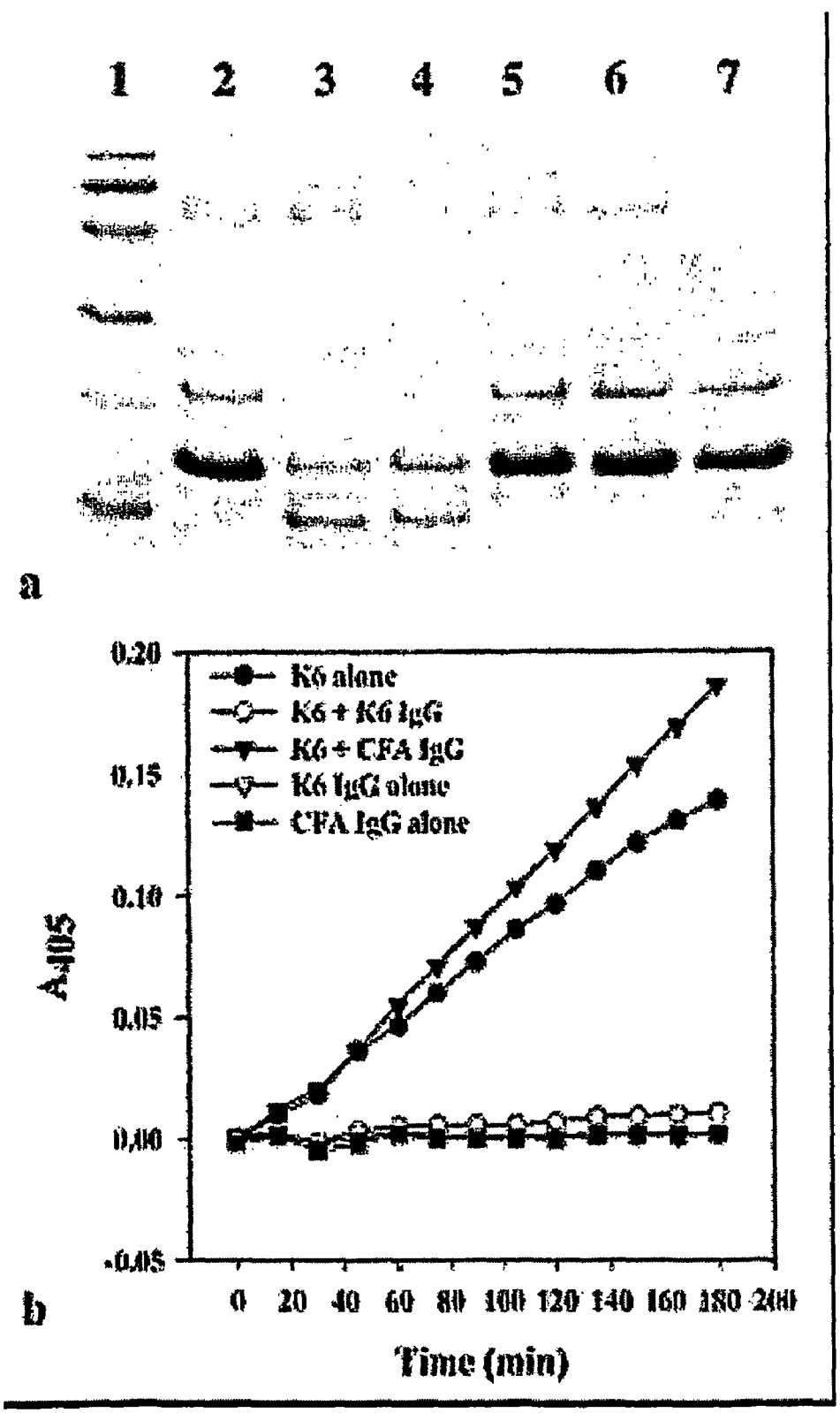

Results: The sera from K6 immunized mice were analyzed by ELISA for levels of K6 antibody production at the conclusion of each experiment, and high levels were determined in each case. The ability of antisera from K6-immunized mice to block K6-specific enzymatic activity was evaluated in vitro (FIG. 20, Table 3). The IgG fraction was isolated from sera of mice immunized with K6, or with adjuvant alone, prior to EAE induction. Pre-incubation of K6 with IgG isolated from K6 immunized mice effectively blocked K6-mediated hydrolysis of MBP (lane 2), while IgG isolated from animals immunized with CFA containing only PBS (lane 3) did not. Addition of IgG isolated from the different experimental groups alone, had no effect on MBP, in the absence of added K6 (lanes 5 and 6). The IgG fraction from K6-immunized mice, but not that from control mice, or that obtained commercially (data not shown), blocked K6-mediated degradation of MBP in vitro (92.3% decrease), (FIG. 20A), and significantly reduced the rate of K6-AcATRpNA substrate hydrolysis (75-87% decrease), (FIG. 20B, Table 4).

TABLE 4

| Sample | Reaction Rate (A405/min) | Normalized against K6 (%) | Change (%) |
| --- | --- | --- | --- |
| K6 alone | 0.000804 | 100 | 0 |
| K6 + anti-K6 IgG | 0.0000619 | 7.7 | −92.3 decrease |
| K6 + anti-CFA IgG | 0.00106 | 131.8 | 31.8 increase |
| anti-K6 IgG control | 0.0000458 | 5.7 | −94.3 decrease |
| anti-CFA IgG control | 0.0000194 | 2.4 | −97.6 decrease |

Percent change in the rate of K6-mediated AcATRpNA-substrate hydrolysis in the presence of added IgG isolated from K6 immunized mice or from mice immunized with PBS alone (CFA control). There was a 92.3% decrease in substrate hydrolysis with the addition of IgG isolated from K6-immunized mice, compared to the rate of substrate hydrolysis seen in the presence of K6 alone. The addition of isolated IgG alone, without added K6, did not result in any significant substrate hydrolysis over time. The addition of anti-CFA resulted in a slight increase in the rate of substrate hydrolysis over that seen with K6 alone, an effect possibly mediated by the ability of IgG to block the rate of K6 self-autolysis.

Parallel to the ability of IgG isolated from K6-immunized mice to block the activity of K6 in vitro, K6-specific monoclonal antibodies blocked K6 mediated substrate hydrolysis (FIG. 21). Pre-incubation of active K6 with K6-specific monoclonal antibodies (hK6-2 or hK6-3) for a period 15 min at RT (molar ratio of 1:1 or 1:10), each effectively, dramatically, and in a dose dependent fashion, blocked K6-mediated hydrolysis of the fluorogenic AcATRpNA substrate (see Table 5). Readings were taken every min, over a period of 88 min. K6-specific monoclonal antibodies resulted in greater than a 75% decrease in the rate of substrate hydrolysis. By contrast normal mouse IgG (control), did not produce similar decreases, and in fact, resulted in a slight increase in K6-mediated substrate hydrolysis by likely decreasing the rate of K6-autolysis.

TABLE 5

| Sample | Reaction Rate (A405/min) | Normalized against K6 (%) | Change (%) |
| --- | --- | --- | --- |
| K6 alone | 6.685E−05 | 100 | 0 |
| Control IgG + K6 (1:1) | 7.675E−05 | 115 | 15% |
| Control IgG + K6 (1:10) | 8.55E−05 | 128 | increase |
| K6-2 IgG + K6 (1:1) | 1.67E−05 | 25 | 28 increase |
| K6-2 IgG + K6 (1:10) | 8.835E−0 | 13 | −75 decrease |
| K6-3 IgG + K6 (1:1) | 1.58E−05 | 24 | −87 decrease |
| K6-3 IgG + K6 (1:10) | 8.135E−06 | 12 | −76 decrease −88 decrease |

These results indicate that the mechanism of action of direct K6-immunization in attenuating disease in the inflammatory animal models examined herein, was likely due to the ability of antibodies generated by this approach to directly block K6-enzymatic activity, which is likely to play key effector functions in mediating inflammatory disease. Therefore, other methods of inhibiting the functional activity of K6, such as K6-specific protease inhibitors, or antisense strategies, also can be used to block inflammatory disease.

Example 16

Immunoglobulins Isolated from K6-Immunized Mice Decrease the Migration of Immune Cells In Vitro The possibility that K6-specific antibodies generated by direct immunization of mice with K6 block the migration of immune cells, was examined by determining the effect of IgG isolated from the sera of K6-immunized mice on the migration of splenocytes in vitro, using a modified Boyden Chamber assay. Splenocytes were isolated from normal mice and grown in complete Click's media containing 10 μg/ml concanavilin A (ConA, Sigma). After 48 hr in culture, cells were harvested and grown for an additional 3 hr in serum starvation media (phenol red free RPMI, 1% bovine serum albumin, 1 mM Hepes Buffer, 50 U/ml penicillin-streptoycin and 2 mM glutamine). Cells were labeled with Calcein AM according to the manufacturers recommendations (Molecular Probes). $1 \times 10^6$ Calcein AM labeled cells were applied in 250 μl of serum starvation media to each of the upper wells of a Matrigel coated Fluoroblock 24 well plate (BD Pharmigen), with or without the addition of 25 μg/ml of IgG from K6 immunized mice, and 750 μl of the same media was added to the lower chamber with SDF-1α (50 ng/ml), added as a chemoattractant. IgG isolated from CFA immunized mice, or commercially available purified mouse IgG (Jackson Laboratories), served as immunoglobulin controls. The fluorescence of cells, which had migrated into the lower chamber, was read after a 24 hr culture period on a Cytoflour 4000 bottom reading plate reader at A530 (BioRad).

Results: A key initiating event in the development of immune-mediated CNS demyelination, is the extravasation and migration of immune cells from the vascular system into the CNS. As described herein, mice with high K6 antibody titers have significantly less spinal cord meningeal and parenchymal inflammation in both TMEV and PLP139-151 induced CNS inflammatory disease. In this example, it is demonstrated in vitro that IgG isolated from K6-immunized mice (FIG. 22), or K6-specific monoclonal antibodies (not shown), inhibit the migration of activated splenocytes in a Boyden Chamber invasion assay. Compared with normal mouse IgG (control) and to the addition of no antibody, the addition of K6-IgG inhibited migration by 25% (*unpaired Student's t-test). These findings indicate the efficacy of K6-specific antibodies generated in an autonomous fashion, in attenuating clinical disease and spinal cord pathology may, at least in part, be due to a decrease in the ability of inflammatory cells to migrate into and within the CNS. These results additionally support the idea that other methods of inhibiting the enzymatic activity of K6, would also abrogate inflammatory cell migration.

Example 17

K6 is Upregulated in Activated Immune Cells

To approach the question of whether K6-production by infiltrating CNS inflammatory cells, represents constitutive expression, or an upregulation in activated cells, the levels of K6 production and secretion were examined in resting and activated splenocytes, using both flow cytometry and ELISA techniques.

Splenocytes were isolated from normal SJL mice and grown in the presence or absence of 10 µg/ml ConA for T cell activation. Cell were harvested after 72 hr and examined for intracellular K6-production by flow cytometry, using a K6-specific IgG$_{1K}$ monoclonal antibody (K6-2), and an anti-mouse FITC-labeled secondary. Purified mouse IgG$_{1K}$ was used as an isotype control. Cells were co-labeled with PE-labeled T cell markers, CD4 and CD8 (Pharmingen).

Incubation of cells in the presence of ConA (10 µg/ml) for 72 hr (unfilled areas) resulted in an increase in the number and intensity of K6 staining, in CD4+ (FIG. 23A) and CD8+ T cells (FIG. 23B), over that seen in splenocytes cultured in PBS alone.

For examination of K6 production in splenocytes and secretion into the cell culture media, splenocytes isolated from normal SJL mice and cultured in the presence of 10 µg/ml ConA, 5 µg/mL lipolysaccharide (LPS), 20 µg/mL CD3-antibody (CD3-Ab), or PBS alone. Cells and cell culture supernatants, were harvested after a period of 72 hr, and examined for levels of K6 protein by ELISA. Plates were coated with 100 µl of proteins at 250 µg/ml diluted in 0.1 M carbonate buffer, or with 200 µl of cell culture supernatant, and incubated overnight at 4° C. After blocking non-specific binding with 1% BSA, K6 was detected with the K6-specific IgG$_{1K}$ monoclonal antibody (K6-2) and AP-conjugated anti-mouse IgG (Jackson Laboratories). Plates were read at 405 nm.

As shown in FIG. 24 (left panel), specific activation of T cells (Con A and CD3 Ab), or non-specific activation of all splenocytes, produced a significant increase in K6 production, and secretion into the media, compared to those cells grown in PBS alone (FIG. 24 (right panel)). LPS stimulation caused a 2-fold or greater increase in K6 production, while selective T cell activation resulted in approximately a 1.5-fold increase in K6. These results indicate that activated immune cells, such as those seen in CNS-inflammatory lesions, express higher levels of K6 than resting immune cells, which we propose contributes to pathogenesis.

Example 18

X-Ray Structure Refinement and Model

A total of 140 solvent molecules were added to the refined hK6 structure. One tentatively assigned solvent molecule exhibited octahedral coordination geometry with adjacent solvent molecules and short (~2.0 Å) contact distances with these groups. This solvent was therefore assigned as a $Mg^{2+}$ ion 33. Unambiguous density also was visible within the active site region, indicating the presence of a bound benzamidine inhibitor. In the final refined structure, 227 of the 229 amino acid residues were defined in the electron density map. The observed electron density is in full agreement with the amino acid sequence deduced from the cDNA sequence. The peptide backbone of hK6 could be traced unambiguously from its amino-terminal Ile16 to Gln243 (using the chymotrypsinogen numbering scheme). Carboxy-terminal residues Ala244 and Lys245 lacked adequate electron density and were not built into the model. The side chain residues of Lys24, Arg110, Gln239, and Gln243 were undefined in the electron density map and were therefore modeled as alanine residues. Asp150 was modeled in multiple rotamer conformations. Some of the loop regions, in particular the region from Trp215 to Pro225, required extensive rebuilding due to large differences from that of the search model. The model refined to acceptable values for stereochemistry and crystallographic residual (Table 6).

TABLE 6

Crystal, data collection, and refinement statistics

| A. Crystal data | |
|---|---|
| Space group | P212121 |
| Cell dimensions (Å) | a = 39.1 b = 62.1 c = 85.8 |
| Molecules/asymmetric unit | 1 |
| Matthews' constant (Vm) (Å3/Da) | 1.80 |
| Maximum resolution (Å) | 1.75 |
| B. Data Collection and Processing | |
| Total/unique reflections | 495,027/21,777 |
| Completion (43 – 1.75 Å)/(X – 1.75 Å) (%) | 96.0/82.7 |
| I/σ (43 – 1.75 Å)/(1.79X – 1.75 Å) | 43.0/4.9 |
| Rmerge (43 – 1.75Å)/ (1.79X – 1.75 Å) (%) | 5.7/38.2 |
| Wilson temperature factor (Å2) | 26.6 |
| C. Refinement | |
| Rcrystal (43 – 1.75 Å) (%) | 20.9 |
| Rfree (43 – 1.75 Å) (%) | 24.1 |
| rms bond length deviation (Å) | 0.005 |
| rms bond angle deviation (°) | 1.35 |
| rms B-factor deviation (σ) | 2.83 |
| Ramachandran plot (%) | |
| Most favored region | 87.6 |
| Additional allowed region | 12.4 |
| Generously allowed region | 0 |
| Disallowed region | 0 |
| Number of atoms/molecule | |
| Non-H protein | 1,685 |
| Water/ion | 139/1 |

Example 19

Evaluation of Recombinant hK6 Protein

The homogeneity of purified hK6 was evaluated using amino-terminal sequencing and MALDI-TOF mass spectrometry. Mass spectrometry revealed that the hK6 samples used for crystallization contained intact, glycosylated enzyme. The major peak had a mass of 25,866 Da, which is a difference of 1366 Da from the mass calculated from the protein sequence. This extra mass corresponds to approximately six N-acetylglucosamine molecules. Furthermore, peaks corresponding to six glycosylated forms were visible in the mass spectrum, with the average difference in mass between each form being ≈184 Da, which corresponds to the mass of one hexose unit. Amino-terminal sequencing analysis yielded a single sequence of Leu-Val-His-Gly, representing the correct amino terminal sequence for mature hK6.

Example 20

Autolytic Inactivation of hK6

Determination of the x-ray structure of hK6 provides an opportunity to further characterize the autolytic regulation of K6/hK6. Unlike the mouse kallikreins, and similar to trypsin, autolysis of hK6 leads to inactivation. Thus, autolysis represents a potential regulatory mechanism in controlling the activity of hK6. Arg 76, a site of autolysis in hK6, is the most solvent accessible arginine residue in the structure. Both trypsin and hK6 are inactivated by autolysis, and although the sites of autolysis are not identical, both proteases autolyze within the carboxyl terminal domain. The two canonical sites of autolysis in the mouse kallikreins, which are not associated with inactivation are located within the amino terminal domain (at positions 95 and 148). Cleavages within the carboxyl terminal domain may result in destabilization of the structure, and inactivation by autolysis may represent a stability-based mechanism of inactivation. Alternatively, cleavages close to the active site histidine (at position 57) may promote flexibility at this position that is incompatible with the catalytic mechanism.

Example 21

Structural Relationship of hK6 with Other Serine Proteases

The secondary structure of hK6 is composed of thirteen β-strands, two α-helices, two 310-helices, and eight identifiable loop regions. These loop regions have varying functions that, based upon the structures of related serine proteases, include defining substrate specificity and autolytic regulation. In addition, these loops can provide sites for N-glycosylation that may serve to regulate activity in this class of enzymes. When comparing the x-ray structure of hK6 with either bovine trypsin or a mouse kallikrein (pro-renin converting enzyme, mK13) there are three immediately identifiable loop regions adjacent to the active site that exhibit structural heterogeneity. These include residue positions 92-102 (kallikrein loop), 141-152 and 172-178. The kallikrein loop of hK6 is indistinguishable in length in comparison to the degradative proteases trypsin and chymotrypsin, and shorter than that seen in mouse kallikreins or other regulatory type proteases. Although the amino acid sequence within this region differs between hK6 and trypsin, the structures are essentially identical.

The short surface loop comprising residue positions 172-178 is identical in length for hK6, rK6, trypsin, chymotrypsin, mK13, neuropsin, ppKa). The amino acid sequence for hK6 within this region is identical to that of bovine trypsin with the exception of position 178, and adopts an essentially identical structure as bovine trypsin. This short loop is oriented away from the active site, and contrasts with the homologous region in mK13 (which is oriented towards the active site).

The loop region 141-152 in hK6 is shorter than that in trypsin, and leads to a conformation that orients this loop away from the active site in comparison to trypsin. In the comparison with other proteases, the broad-specificity degradative proteases generally have a shorter length loop in this region, whereas the regulatory proteases have longer loops that afford greater contributions to the substrate binding site.

In general, the structural data for the variable surface loop regions that border the active site describe loops that are both short and generally oriented away from the substrate binding site. Thus, their contribution to formation of the S2 and S3 sites within the protease are limited. This is a characteristic feature of the degradative type proteases, exemplified by the digestive enzymes trypsin and chymotrypsin.

Kinetic results indicate that hK6 has a 133-fold greater catalytic efficiency for cleavage after arginine compared to cleavage after lysine in a tripeptide substrate. Thus, the specificity of hK6 for an arginine versus lysine at the P1 position is more similar to proteases such as porcine kallikrein, and thrombin which have similar preferences for arginine over lysine at the P1 position, and unlike trypsin which has a much smaller preference of only 2- to 10-fold. The S1 binding pocket is defined by residues 189-195, 214-220, and 224-228 and the catalytic triad. Regions 189-195 and 224-228 are identical between hK6 and trypsin, however, region 214-220 is heterogenous with regard to both length and sequence, and is therefore the likely structural determinant of the P1 specificity.

It has been reported that N-linked oligosaccharides within the kallikrein loop of neuropsin affect the size of the S2 pocket and that mutations in this region result in a significant decrease in both kcat and Km (while maintaining the overall kcat/Km). As previously mentioned, hK6 lacks the equivalent kallikrein loop characteristic of the regulatory proteases, including the N-linked asparagine residue at position 95. However mass spectrometry data suggests there is a potential N-linked glycosylation site at position Asn132 that is not present in any of the other known kallikrein structures. In contrast to the N-glycosylation site found on the kallikrein loop in other kallikreins, this site is quite distant from the active site and lies at the "rear" of the enzyme. There is electron density present in this region that is indicative of possible sugar residues. The function of this site of glycosylation has yet to be determined, but due to its distal location from the active site, it is hypothesized not to affect enzyme specificity or function.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating multiple sclerosis in a mammal, said method comprising administering to said mammal an amount of an antibody having specific binding affinity for kallikrein 6 (K6) effective to treat said multiple sclerosis, wherein said antibody inhibits the enzyme activity of K6.

2. The method of claim 1, wherein said method further comprises monitoring said multiple sclerosis in said mammal.

3. The method of claim 1, wherein said antibody is polyclonal.

4. The method of claim 1, wherein said antibody is monoclonal.

* * * * *

SEQUENCE LISTING

<160> NUMBER OF SEQ ID NOS: 3

<210> SEQ ID NO 1
<211> LENGTH: 4
<212> TYPE: PRT
<213> ORGANISM: Homo sapiens

<400> SEQUENCE: 1

Val Val His Gly
 1

<210> SEQ ID NO 2
<211> LENGTH: 1413
<212> TYPE: DNA
<213> ORGANISM: Homo sapiens

<400> SEQUENCE: 2

```
gtcgacccac gcgtccggct ggctggctcg ctctctcctg gggacacaga ggtcggcagg      60
cagcacacag agggacctac gggcagctgt tccttccccc gactcaagaa tccccggagg     120
cccggaggcc tgcagcagga gcggccatga agaagctgat ggtggtgctg agtctgattg     180
ctgcagcctg ggcagaggag cagaataagt tggtgcatgg cggaccctgc gacaagacat     240
ctcaccccta ccaagctgcc ctctacacct cgggccactt gctctgtggt ggggtcctta     300
tccatccact gtgggtcctc acagctgccc actgcaaaaa accgaatctt caggtcttcc     360
tggggaagca taaccttcgg caaagggaga gttcccagga gcagagttct gttgtccggg     420
ctgtgatcca ccctgactat gatgccgcca gccatgacca ggacatcatg ctgttgcgcc     480
tggcacgccc agccaaactc tctgaactca tccagcccct tccccctggag agggactgct     540 cagccaacac caccagctgc cacatcctgg gctgggcaa gacagcagat ggtgatttcc     600
ctgacaccat ccagtgtgca tacatccacc tggtgtcccg tgaggagtgt gagcatgcct     660
accctggcca gatcacccag aacatgttgt gtgctgggga tgagaagtac gggaaggatt     720
cctgccaggg tgattctggg ggtccgctgg tatgtggaga ccacctccga ggccttgtgt     780
catggggtaa catcccctgt ggatcaaagg agaagccagg agtctacacc aacgtctgca     840
gatacacgaa ctggatccaa aaaccattc aggccaagtg accctgacat gtgacatcta     900
cctcccgacc taccaccca ctggctggtt ccagaacgtc tctcacctag accttgcctc     960
ccctcctctc ctgcccagct ctgaccctga tgcttaataa acgcagcgac gtgagggtcc    1020
tgattctccc tggttttacc ccagctccat ccttgcatca ctggggagga cgtgatgagt    1080
gaggacttgg gtcctcggtc ttaccccac cactaagaga atacaggaaa tcccttcta    1140 ggcatctcct ctccccaacc cttccacacg tttgatttct tcctgcagag gcccagccac    1200
gtgtctggaa tccagctcc gctgcttact gtcggtgtcc ccttgggatg taccttctt    1260 cactgcagat ttctcacctg taagatgaag ataaggatga tacagtctcc ataaggcagt    1320
ggctgttgga aagatttaag gtttcacacc tatgacatac atggaatagc acctgggcca    1380
ccatgcactc aataaagaat gaattttatt atg                                1413
```

<210> SEQ ID NO 3
<211> LENGTH: 17
<212> TYPE: PRT
<213> ORGANISM: Artificial Sequence
<220> FEATURE:
<223> OTHER INFORMATION: Non-specific antigen peptide -continued

```
<400> SEQUENCE: 3

Ile Ser Gln Ala Val His Ala Ala His Ala Glu Ile Asn Glu Ala Gly
1               5                   10                  15
Arg
```